[12] United States Patent
Cramer et al.

(10) Patent No.: US 11,962,892 B2
(45) Date of Patent: Apr. 16, 2024

(54) IMAGE BASED DENTITION TRACKING

(71) Applicant: ALIGN TECHNOLOGY, INC., San Jose, CA (US)

(72) Inventors: Christopher E. Cramer, Durham, NC (US); Rajiv Venkata, San Jose, CA (US); Leela Parvathaneni, San Jose, CA (US); Phillip Thomas Harris, Cary, NC (US); Sravani Gurijala, Apex, NC (US); Svetozar Hubenov, Luzen (CH); Sebastien Hareng, San Jose, CA (US); Guotu Li, Apex, NC (US); Yun Gao, Cary, NC (US); Chad Clayton Brown, Cary, NC (US)

(73) Assignee: ALIGN TECHNOLOGY, INC., San Jose, CA (US)

(*) Notice: Subject to any disclaimer, the term of this patent is extended or adjusted under 35 U.S.C. 154(b) by 9 days.

(21) Appl. No.: 17/443,243

(22) Filed: Jul. 22, 2021

(65) Prior Publication Data
US 2022/0023003 A1 Jan. 27, 2022

Related U.S. Application Data

(60) Provisional application No. 63/200,432, filed on Mar. 5, 2021, provisional application No. 62/705,954, filed on Jul. 23, 2020.

(51) Int. Cl.
H04N 23/60 (2023.01)
A61B 1/24 (2006.01)
(Continued)

(52) U.S. Cl.
CPC .............. *H04N 23/64* (2023.01); *A61B 1/24* (2013.01); *A61B 5/0088* (2013.01); *A61C 7/002* (2013.01);
(Continued)

(58) Field of Classification Search
CPC .... G06Q 50/22; G06Q 10/02; G06Q 10/1095; G06Q 30/0282; G06Q 30/0621;
(Continued)

(56) References Cited

U.S. PATENT DOCUMENTS 5,975,893 A 11/1999 Chishti et al.
6,227,850 B1 5/2001 Chishti et al.
(Continued)

OTHER PUBLICATIONS

U.S. Appl. No. 17/443,242, filed Jul. 22, 2021.
(Continued)

Primary Examiner — Ming Wu
(74) Attorney, Agent, or Firm — FISHERBROYLES, LLP

(57) ABSTRACT

A method of dental treatment may include receiving photos of a person's dentition, identifying a stage of a treatment plan administered to the person's dentition, gathering a three-dimensional (3D) model of the person's dentition corresponding to the stage of the treatment plan, projecting attributes of the 3D model of the person's dentition onto an image plane to get a projected representation of the person's dentition at the stage of the treatment plan, comparing the photos to the projected representation to derive an error image representing the comparison, and analyzing the error image for discrepancies, wherein the discrepancies represent one or more deviations of the person's dentition from the stage of the treatment plan.

24 Claims, 27 Drawing Sheets

(51) Int. Cl.
| | |
|---|---|
| *A61B 5/00* | (2006.01) |
| *A61C 7/00* | (2006.01) |
| *A61C 7/08* | (2006.01) |
| *A61C 7/14* | (2006.01) |
| *A61C 9/00* | (2006.01) |
| *G06F 18/21* | (2023.01) |
| *G06F 18/2415* | (2023.01) |
| *G06F 18/2431* | (2023.01) |
| *G06N 3/04* | (2023.01) |
| *G06N 3/042* | (2023.01) |
| *G06N 3/08* | (2023.01) |
| *G06T 7/00* | (2017.01) |
| *G06T 7/246* | (2017.01) |
| *G06T 7/30* | (2017.01) |
| *G06T 7/60* | (2017.01) |
| *G06T 7/70* | (2017.01) |
| *G06T 7/73* | (2017.01) |
| *G06T 7/80* | (2017.01) |
| *G06T 17/00* | (2006.01) |
| *G06T 17/20* | (2006.01) |
| *G06T 19/00* | (2011.01) |
| *G06V 10/44* | (2022.01) |
| *G06V 10/56* | (2022.01) |
| *G06V 10/98* | (2022.01) |
| *G16H 10/60* | (2018.01) |
| *G16H 20/40* | (2018.01) |
| *G16H 30/40* | (2018.01) |
| *G16H 40/20* | (2018.01) |
| *G16H 50/20* | (2018.01) |
| *G16H 50/50* | (2018.01) |
| *G16H 70/20* | (2018.01) |
| *G16H 80/00* | (2018.01) |

(52) U.S. Cl.
CPC ............... *A61C 7/08* (2013.01); *A61C 7/146* (2013.01); *A61C 9/0053* (2013.01); *G06F 18/217* (2023.01); *G06F 18/2415* (2023.01); *G06F 18/2431* (2023.01); *G06N 3/04* (2013.01); *G06N 3/042* (2023.01); *G06N 3/08* (2013.01); *G06T 7/0012* (2013.01); *G06T 7/0014* (2013.01); *G06T 7/251* (2017.01); *G06T 7/30* (2017.01); *G06T 7/60* (2013.01); *G06T 7/70* (2017.01); *G06T 7/74* (2017.01); *G06T 7/80* (2017.01); *G06T 17/00* (2013.01); *G06T 17/20* (2013.01); *G06T 19/00* (2013.01); *G06V 10/443* (2022.01); *G06V 10/56* (2022.01); *G06V 10/98* (2022.01); *G16H 10/60* (2018.01); *G16H 20/40* (2018.01); *G16H 30/40* (2018.01); *G16H 40/20* (2018.01); *G16H 50/20* (2018.01); *G16H 50/50* (2018.01); *G16H 70/20* (2018.01); *G16H 80/00* (2018.01); *G06T 2200/24* (2013.01); *G06T 2207/20081* (2013.01); *G06T 2207/20084* (2013.01); *G06T 2207/30036* (2013.01); *G06T 2207/30244* (2013.01); *G06T 2210/41* (2013.01); *G06V 2201/03* (2022.01)

(58) Field of Classification Search
CPC ............ G06Q 30/0631; G06Q 30/0643; G06T 2207/30036; G06T 7/0012; G06T 2207/10081; G06T 17/00; G06T 19/20; G06T 11/008; G06T 2207/10088; G06T 7/0014; G06T 2210/41; G06T 2219/2004; G06T 2219/2021; G06T 2207/20084; G06T 7/11; G06T 15/005; G06T 17/10; G06T 2207/20081; G06T 7/136; G06T 7/62; G06T 17/20; G06T 19/00; G06T 2207/10; G06T 2207/10004; G06T 2207/10012; G06T 2207/10028; G06T 2207/20076; G06T 2207/20101; G06T 2207/30204; G06T 2210/56; G06T 7/0004; G06T 7/001; G06T 7/10; G06T 7/521; G06T 7/593; G06T 7/70; G06T 7/73

See application file for complete search history.

(56) References Cited

U.S. PATENT DOCUMENTS

| | | | |
|---|---|---|---|
| 6,227,851 | B1 | 5/2001 | Chishti et al. |
| 6,299,440 | B1 | 10/2001 | Phan et al. |
| 6,318,994 | B1 | 11/2001 | Chishti et al. |
| 6,371,761 | B1 | 4/2002 | Cheang et al. |
| 6,386,878 | B1 | 5/2002 | Pavlovskaia et al. |
| 6,406,292 | B1 | 6/2002 | Chishti et al. |
| 6,409,504 | B1 | 6/2002 | Jones et al. |
| 6,457,972 | B1 | 10/2002 | Chishti et al. |
| 6,488,499 | B1 | 12/2002 | Miller |
| 6,514,074 | B1 | 2/2003 | Chishti et al. |
| 6,554,611 | B2 | 4/2003 | Chishti et al. |
| 6,582,229 | B1 | 6/2003 | Miller et al. |
| 6,602,070 | B2 | 8/2003 | Miller et al. |
| 6,621,491 | B1 | 9/2003 | Baumrind et al. |
| 6,688,886 | B2 | 2/2004 | Hughes et al. |
| 6,726,478 | B1 | 4/2004 | Isiderio et al. |
| 6,729,876 | B2 | 5/2004 | Chishti et al. |
| 6,739,869 | B1 | 5/2004 | Taub et al. |
| 6,767,208 | B2 | 7/2004 | Kaza |
| 6,783,360 | B2 | 8/2004 | Chishti |
| 7,040,896 | B2 | 5/2006 | Pavlovskaia et al. |
| 7,063,532 | B1 | 6/2006 | Jones et al. |
| 7,074,038 | B1 | 7/2006 | Miller |
| 7,074,039 | B2 | 7/2006 | Kopelman et al. |
| 7,077,647 | B2 | 7/2006 | Choi et al. |
| 7,108,508 | B2 | 9/2006 | Hedge et al. |
| 7,134,874 | B2 | 11/2006 | Chishti et al. |
| 7,156,661 | B2 | 1/2007 | Choi et al. |
| 7,160,107 | B2 | 1/2007 | Kopelman et al. |
| 7,241,142 | B2 | 7/2007 | Abolfathi et al. |
| 7,293,988 | B2 | 11/2007 | Wen |
| 7,309,230 | B2 | 12/2007 | Wen |
| 7,357,634 | B2 | 4/2008 | Knopp |
| 7,555,403 | B2 | 6/2009 | Kopelman et al. |
| 7,637,740 | B2 | 12/2009 | Knopp |
| 7,689,398 | B2 | 3/2010 | Cheng et al. |
| 7,736,147 | B2 | 6/2010 | Kaza et al. |
| 7,746,339 | B2 | 6/2010 | Matov et al. |
| 7,844,356 | B2 | 11/2010 | Matov et al. |
| 7,844,429 | B2 | 11/2010 | Matov et al. |
| 7,865,259 | B2 | 1/2011 | Kuo et al. |
| 7,878,804 | B2 | 2/2011 | Korytov et al. |
| 7,880,751 | B2 | 2/2011 | Kuo et al. |
| 7,904,308 | B2 | 3/2011 | Arnone et al. |
| 7,930,189 | B2 | 4/2011 | Kuo |
| 7,942,672 | B2 | 5/2011 | Kuo |
| 7,970,627 | B2 | 6/2011 | Kuo et al. |
| 7,970,628 | B2 | 6/2011 | Kuo et al. |
| 8,038,444 | B2 | 10/2011 | Kitching et al. |
| 8,044,954 | B2 | 10/2011 | Kitching et al. |
| 8,075,306 | B2 | 12/2011 | Kitching et al. |
| 8,092,215 | B2 | 1/2012 | Stone-Collonge et al. |
| 8,099,268 | B2 | 1/2012 | Kitching et al. |
| 8,108,189 | B2 | 1/2012 | Chelnokov et al. |
| 8,126,726 | B2 | 2/2012 | Matov et al. |
| 8,260,591 | B2 | 9/2012 | Kass et al. |
| 8,275,180 | B2 | 9/2012 | Kuo |
| 8,401,826 | B2 | 3/2013 | Cheng et al. |
| 8,439,672 | B2 | 5/2013 | Matov et al. |
| 8,562,338 | B2 | 10/2013 | Kitching et al. |
| 8,591,225 | B2 | 11/2013 | Wu et al. |
| 8,788,285 | B2 | 7/2014 | Kuo |
| 8,843,381 | B2 | 9/2014 | Kuo et al. |

(56) References Cited

U.S. PATENT DOCUMENTS

| | | |
|---|---|---|
| 8,874,452 B2 | 10/2014 | Kuo |
| 8,896,592 B2 | 11/2014 | Boltunov et al. |
| 8,930,219 B2 | 1/2015 | Trosien et al. |
| 9,037,439 B2 | 5/2015 | Kuo et al. |
| 9,060,829 B2 | 6/2015 | Sterental et al. |
| 9,125,709 B2 | 9/2015 | Matty |
| 9,211,166 B2 | 12/2015 | Kuo et al. |
| 9,220,580 B2 | 12/2015 | Borovinskih et al. |
| 9,364,296 B2 | 6/2016 | Kuo |
| 9,375,300 B2 | 6/2016 | Matov et al. |
| 9,414,897 B2 | 8/2016 | Wu et al. |
| 9,492,245 B2 | 11/2016 | Sherwood et al. |
| 9,642,678 B2 | 5/2017 | Kuo |
| 10,248,883 B2 | 4/2019 | Borovinskih et al. |
| 10,342,638 B2 | 7/2019 | Kitching et al. |
| 10,463,452 B2 | 11/2019 | Matov et al. |
| 10,595,966 B2 | 3/2020 | Carrier, Jr. et al. |
| 10,617,489 B2 | 4/2020 | Grove et al. |
| 10,722,328 B2 | 7/2020 | Velazquez et al. |
| 10,758,322 B2 | 9/2020 | Pokotilov et al. |
| 10,779,718 B2 | 9/2020 | Meyer et al. |
| 10,792,127 B2 | 10/2020 | Kopelman et al. |
| 10,828,130 B2 | 11/2020 | Pokotilov et al. |
| 10,835,349 B2 | 11/2020 | Cramer et al. |
| 10,973,611 B2 | 4/2021 | Pokotilov et al. |
| 10,996,813 B2 | 5/2021 | Makarenkova et al. |
| 10,997,727 B2 | 5/2021 | Xue et al. |
| 11,020,205 B2 | 6/2021 | Li et al. |
| 11,020,206 B2 | 6/2021 | Shi et al. |
| 11,026,766 B2 | 6/2021 | Chekh et al. |
| 11,033,359 B2 | 6/2021 | Velazquez et al. |
| 11,071,608 B2 | 7/2021 | Derakhshan et al. |
| 11,096,763 B2 | 8/2021 | Akopov et al. |
| 11,116,605 B2 | 9/2021 | Nyukhtikov et al. |
| 2003/0008259 A1 | 1/2003 | Kuo et al. |
| 2003/0143509 A1 | 7/2003 | Kopelman et al. |
| 2003/0207227 A1 | 11/2003 | Abolfathi |
| 2004/0137400 A1 | 7/2004 | Chishti et al. |
| 2004/0152036 A1 | 8/2004 | Abolfathi |
| 2004/0197728 A1 | 10/2004 | Abolfathi et al. |
| 2004/0209221 A1 | 10/2004 | Hansen et al. |
| 2004/0259049 A1 | 12/2004 | Kopelman et al. |
| 2005/0182654 A1 | 8/2005 | Abolfathi et al. |
| 2005/0244791 A1 | 11/2005 | Davis et al. |
| 2006/0127836 A1 | 6/2006 | Wen |
| 2006/0127852 A1 | 6/2006 | Wen |
| 2006/0127854 A1 | 6/2006 | Wen |
| 2006/0275731 A1 | 12/2006 | Wen et al. |
| 2006/0275736 A1 | 12/2006 | Wen et al. |
| 2008/0306724 A1 | 12/2008 | Kitching et al. |
| 2010/0009308 A1 | 1/2010 | Wen et al. |
| 2010/0068672 A1 | 3/2010 | Arjomand et al. |
| 2010/0068676 A1 | 3/2010 | Mason et al. |
| 2010/0092907 A1 | 4/2010 | Knopp |
| 2010/0167243 A1 | 7/2010 | Spiridonov et al. |
| 2013/0204599 A1 | 8/2013 | Matov et al. |
| 2014/0120493 A1* | 5/2014 | Levin .................. A61C 9/0066 433/29 |
| 2016/0008116 A1 | 1/2016 | Glinec et al. |
| 2016/0135925 A1 | 5/2016 | Mason et al. |
| 2016/0242870 A1 | 8/2016 | Matov et al. |
| 2016/0310235 A1 | 10/2016 | Derakhshan et al. |
| 2017/0049311 A1* | 2/2017 | Borovinskih ......... G06T 7/0016 |
| 2017/0100207 A1* | 4/2017 | Wen ..................... A61C 7/002 |
| 2017/0273760 A1 | 9/2017 | Morton et al. |
| 2017/0281313 A1 | 10/2017 | Kim |
| 2018/0125610 A1* | 5/2018 | Carrier, Jr. .............. A61B 1/24 |
| 2018/0280118 A1 | 10/2018 | Cramer |
| 2018/0353263 A1 | 12/2018 | Salah et al. |
| 2019/0029784 A1 | 1/2019 | Moalem et al. |
| 2019/0053876 A1 | 2/2019 | Sterental et al. |
| 2019/0125493 A1 | 5/2019 | Salah et al. |
| 2019/0192259 A1 | 6/2019 | Kopelman et al. |
| 2019/0328487 A1 | 10/2019 | Levin et al. |
| 2019/0328488 A1 | 10/2019 | Levin et al. |
| 2019/0333622 A1 | 10/2019 | Levin et al. |
| 2019/0343601 A1 | 11/2019 | Roschin et al. |
| 2020/0000552 A1 | 1/2020 | Mednikov et al. |
| 2020/0000554 A1 | 1/2020 | Makarenkova et al. |
| 2020/0000555 A1 | 1/2020 | Yuryev et al. |
| 2020/0005764 A1 | 1/2020 | Chae |
| 2020/0085546 A1 | 3/2020 | Li et al. |
| 2020/0105028 A1 | 4/2020 | Gao et al. |
| 2020/0107915 A1 | 4/2020 | Roschin et al. |
| 2020/0117903 A1 | 4/2020 | Goel et al. |
| 2020/0132437 A1* | 4/2020 | Stavis .................... H01L 22/20 |
| 2020/0155274 A1 | 5/2020 | Pimenov et al. |
| 2020/0160612 A1 | 5/2020 | Bowen |
| 2020/0214800 A1 | 7/2020 | Matov et al. |
| 2020/0293174 A1 | 9/2020 | Diaz et al. |
| 2020/0294677 A1 | 9/2020 | Godinho et al. |
| 2020/0297458 A1 | 9/2020 | Roschin et al. |
| 2020/0306011 A1 | 10/2020 | Chekhonin et al. |
| 2020/0306012 A1 | 10/2020 | Roschin et al. |
| 2020/0315744 A1 | 10/2020 | Cramer |
| 2020/0360109 A1 | 11/2020 | Gao et al. |
| 2021/0073998 A1 | 3/2021 | Brown et al. |
| 2021/0134436 A1 | 5/2021 | Meyer et al. |
| 2021/0174477 A1 | 6/2021 | Shi et al. |
| 2021/0186659 A1 | 6/2021 | Li et al. |
| 2023/0024672 A1 | 1/2023 | Bonutti et al. |

OTHER PUBLICATIONS

U.S. Appl. No. 17/443,244, filed Jul. 22, 2021.
U.S. Appl. No. 17/443,245, filed Jul. 22, 2021.
U.S. Appl. No. 17/443,247, filed Jul. 22, 2021.
U.S. Appl. No. 17/443,248, filed Jul. 22, 2021.

* cited by examiner

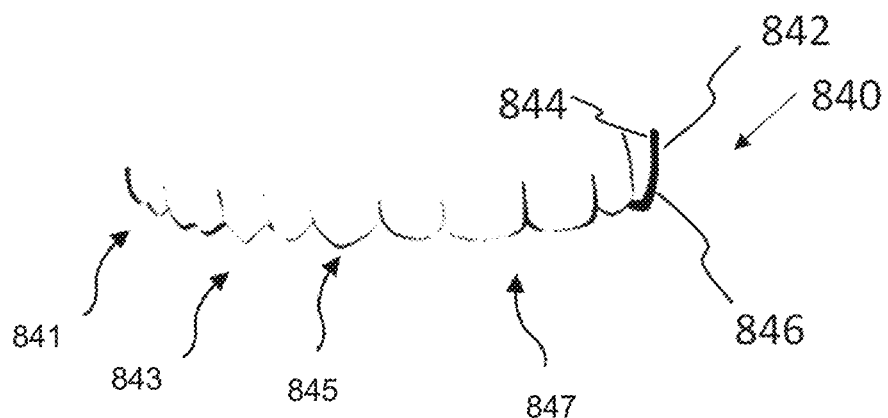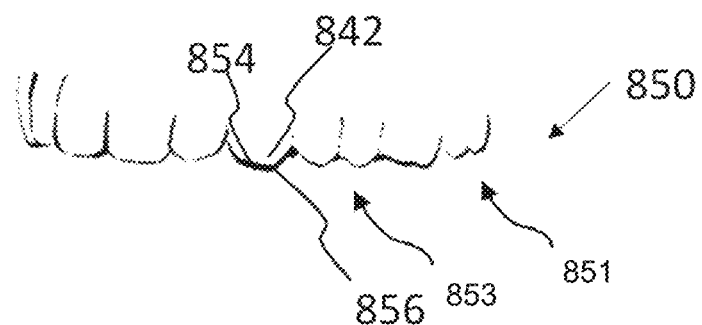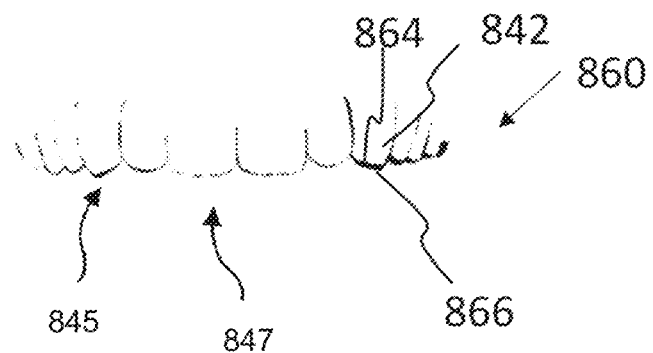
FIG. 8

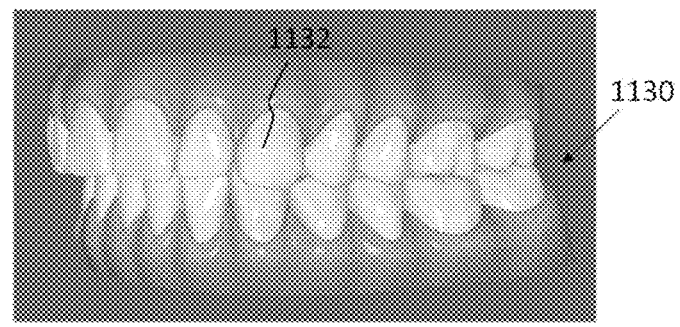
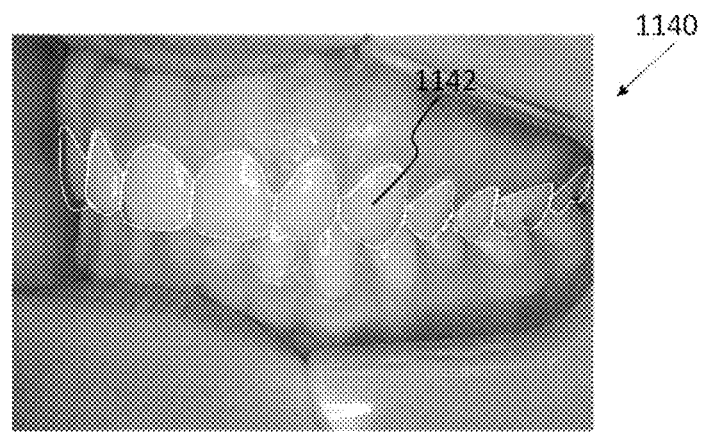
FIG. 11

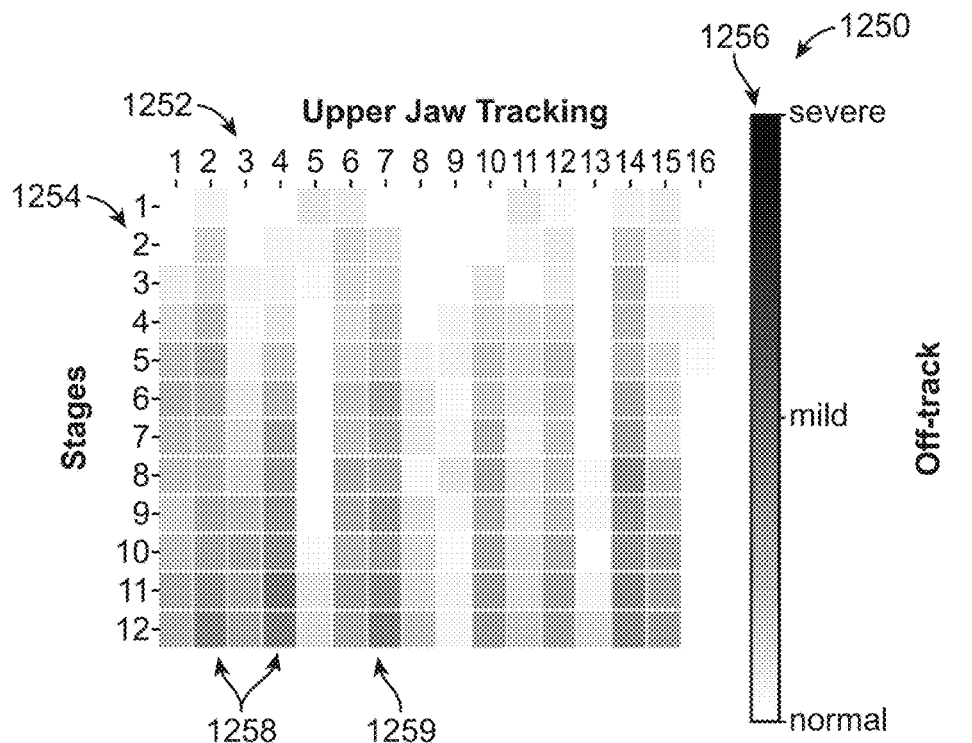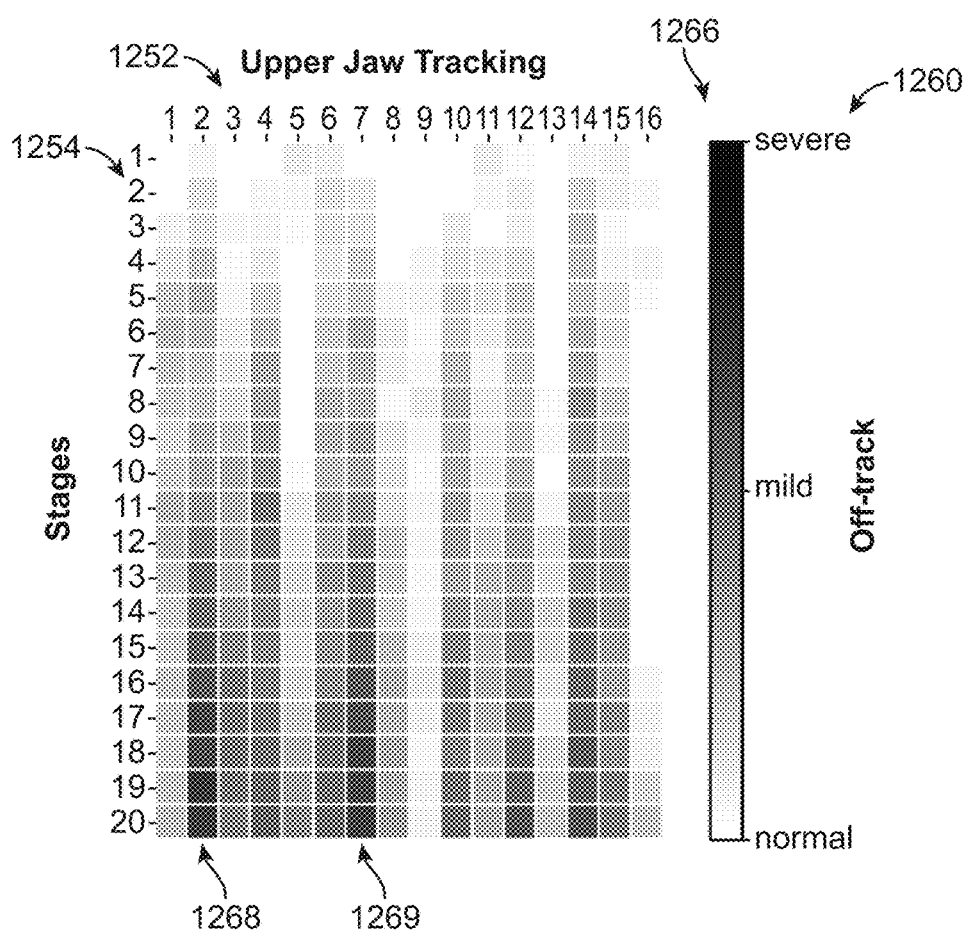
FIG. 12

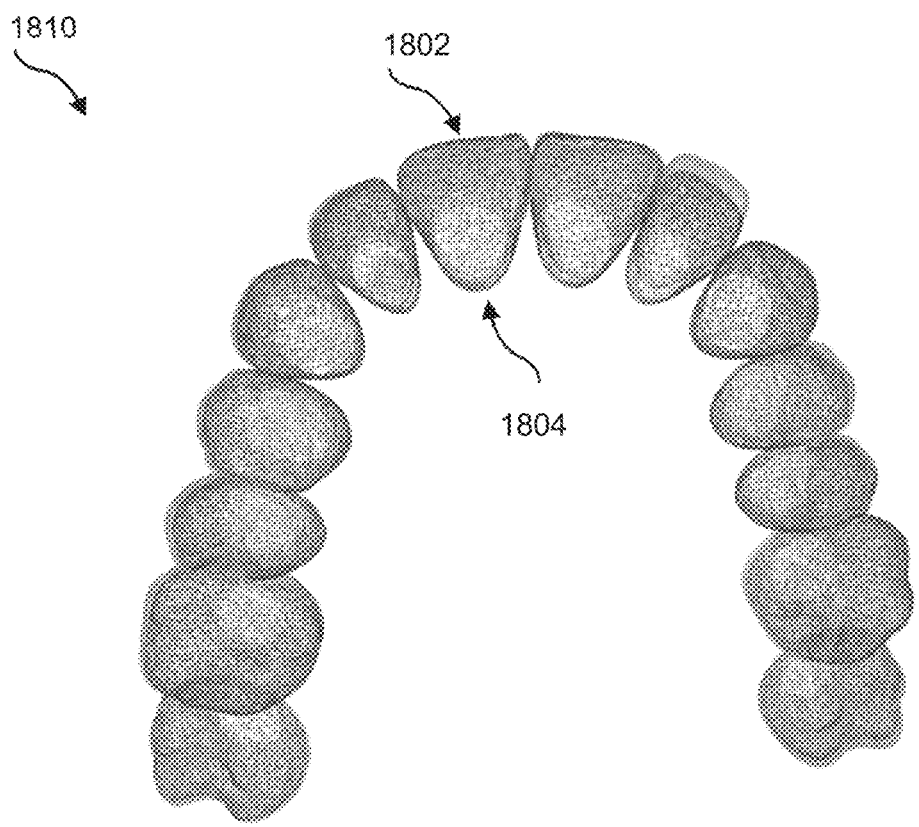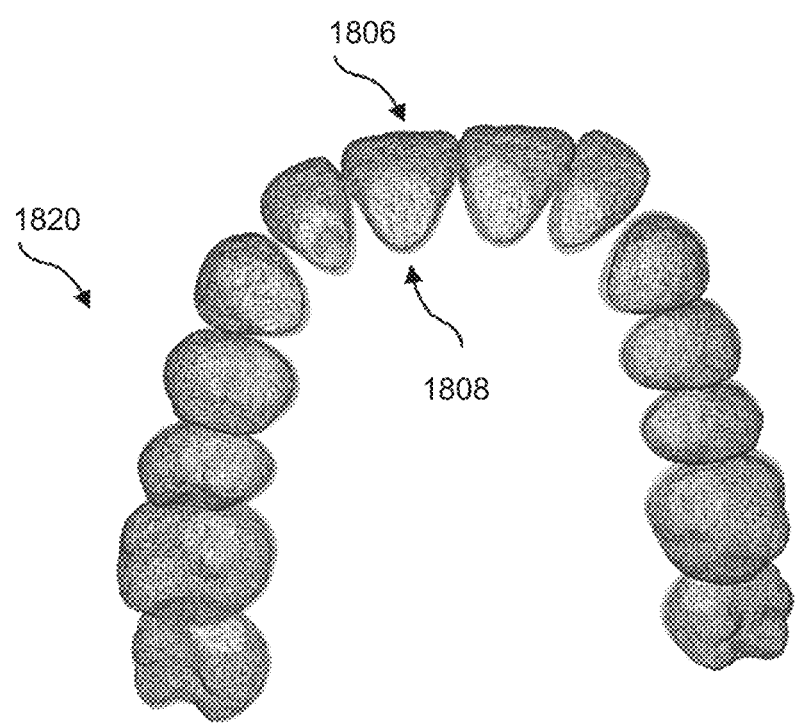
FIG. 18

IMAGE BASED DENTITION TRACKING

RELATED APPLICATIONS

This application claims the benefit under 35 U.S.C. § 119(e) of U.S. Provisional Patent Application No. 63/200,432, filed Mar. 5, 2021, and of U.S. Provisional Patent Application No. 62/705,954, filed Jul. 23, 2021, both titled "VIRTUAL DENTAL CARE," which applications are incorporated herein, in their entirety, by this reference.

BACKGROUND

The practice of medicine is evolving toward tele-medicine—the remote treatment of patients. Telemedicine allows doctors to assess the patient's needs, in some instances provide treatment suggestions for the patients without the hassle and risks involved in person treatments. However, current systems and methods related to dental care are less than desirable in many ways. For example, many dental care contexts require a patient to physically consult with a dentist for various purposes, such as initial assessments, obtaining diagnoses for various conditions, obtaining treatment plans and/or appliances prescribed by treatment plans, and tracking progress of a treatment. Existing dental care solutions reliant on live consultations and/or diagnoses are particularly problematic during times when dental offices are inaccessible due to emergencies, pandemics, physical inaccessibility, and/or impracticality.

SUMMARY

As will be described in greater detail below, the present disclosure describes various systems and methods for virtual dental care to remote patients.

In addition, the systems and methods described herein may improve the functioning of a computing device by reducing computing resources and overhead for acquiring and storing updated patient data, thereby improving processing efficiency of the computing device over conventional approaches. These systems and methods may also improve the field of orthodontic treatment by analyzing data to efficiently target treatment areas and providing patients with access to more practitioners than conventionally available.

INCORPORATION BY REFERENCE

All patents, applications, and publications referred to and identified herein are hereby incorporated by reference in their entirety, and shall be considered fully incorporated by reference even though referred to elsewhere in the application.

BRIEF DESCRIPTION OF THE DRAWINGS

A better understanding of the features, advantages and principles of the present disclosure will be obtained by reference to the following detailed description that sets forth illustrative embodiments, and the accompanying drawings of which:

FIG. 8 shows a differential error image of teeth of a patient for a stage of treatment, according to embodiments herein.

FIG. 11 shows a side-by-side of a rendered teeth image and actual teeth image of a patient for a stage of treatment.

FIG. 12 shows charts of differential error for teeth of a patient for each stage of treatment, according to embodiments herein.

FIG. 18 shows segmented mesh teeth arches generated from existing scans of a patient's teeth and 2D images for a patent's teeth, according to embodiments herein.

DETAILED DESCRIPTION

The following detailed description and provides a better understanding of the features and advantages of the inventions described in the present disclosure in accordance with the embodiments disclosed herein. Although the detailed description includes many specific embodiments, these are provided by way of example only and should not be construed as limiting the scope of the inventions disclosed herein.

Virtual Care System

Figure 1A:
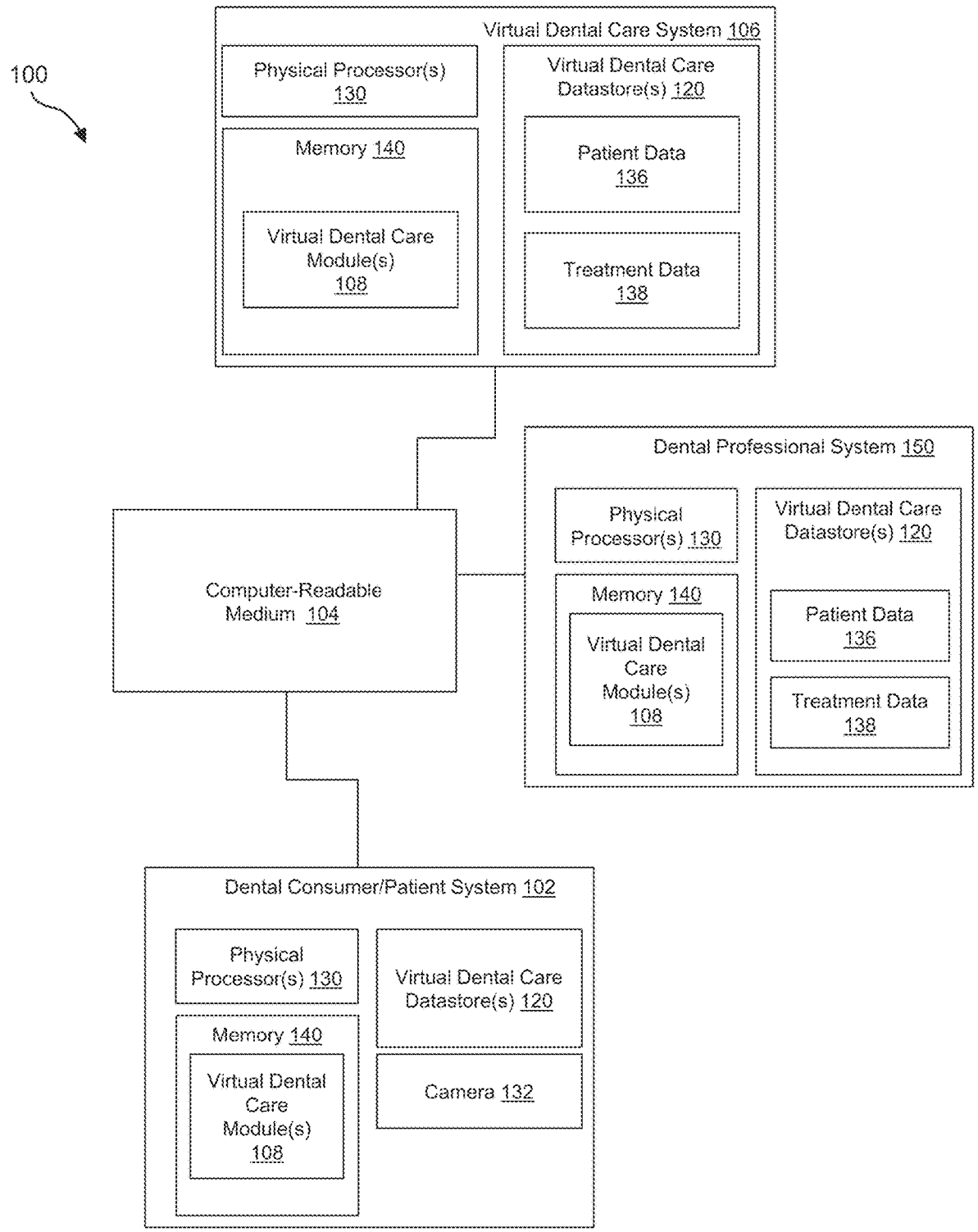
FIG. 1A shows a block diagram of an example system for virtual dental care, in accordance with some embodiments.

FIG. 1A shows a block diagram of an example system for virtual dental care, in accordance with some embodiments. As shown in FIG. 1A, system 100 may include a dental consumer/patient system 102, a dental professional system 150, a virtual dental care system 106, and a computer-readable medium 104. The dental consumer/patient system 102, dental professional system 150, and virtual dental care system 106 may communicate to one another over the computer-readable medium 104.

Dental consumer/patient system 102 generally represents any type or form of computing device capable of reading computer-executable instructions. Dental consumer/patient system 102 may be, for example, a desktop computer, a tablet computing device, a laptop, a smartphone, an augmented reality device, or other consumer device. Additional examples of dental consumer/patient system 102 include, without limitation, laptops, tablets, desktops, servers, cellular phones, Personal Digital Assistants (PDAs), multimedia players, embedded systems, wearable devices (e.g., smart watches, smart glasses, etc.), smart vehicles, smart packaging (e.g., active or intelligent packaging), gaming consoles, Internet-of-Things devices (e.g., smart appliances, etc.), variations or combinations of one or more of the same, and/or any other suitable computing device. The dental consumer/patient system 102 need not be a clinical scanner (e.g., an intraoral scanner), though it is contemplated that in some implementations, the functionalities described herein in relation to the dental consumer/patient system 102 may be incorporated into a clinical scanner. As an example of various implementations, the camera 132 of the dental consumer/patient system 102 may comprise an ordinary camera that captures 2D images of the patient's dentition and does not capture height-map and/or other data that is used to stitch a mesh of a 3D surface.

In some implementations, the dental consumer/patient system 102 is configured to interface with a dental consumer and/or dental patient. A "dental consumer," as used herein, may include a person seeking assessment, diagnosis, and/or treatment for a dental condition (general dental condition, orthodontic condition, endodontic condition, condition requiring restorative dentistry, etc.). A dental consumer may, but need not, have agreed to and/or started treatment for a dental condition. A "dental patient," as used herein, may include a person who has agreed to diagnosis and/or treatment for a dental condition. A dental consumer and/or a dental patient, may, for instance, be interested in and/or have started orthodontic treatment, such as treatment using one or more (e.g., a sequence of) aligners (e.g., polymeric appliances having a plurality of tooth-receiving cavities shaped to successively reposition a person's teeth from an initial arrangement toward a target arrangement). In various implementations, the dental consumer/patient system 102 provides a dental consumer/dental patient with software (e.g., one or more webpages, standalone applications, mobile applications, etc.) that allows the dental consumer/patient to capture images of their dentition, interact with dental professionals (e.g., users of the dental professional system 150), manage treatment plans (e.g., those from the virtual dental care system 106 and/or the dental professional system 150), and/or communicate with dental professionals (e.g., users of the dental professional system 150).

Dental professional system 150 generally represents any type or form of computing device capable of reading computer-executable instructions. Dental professional system 150 may be, for example, a desktop computer, a tablet computing device, a laptop, a smartphone, an augmented reality device, or other consumer device. Additional examples of dental professional system 150 include, without limitation, laptops, tablets, desktops, servers, cellular phones, Personal Digital Assistants (PDAs), multimedia players, embedded systems, wearable devices (e.g., smart watches, smart glasses, etc.), smart vehicles, smart packaging (e.g., active or intelligent packaging), gaming consoles, Internet-of-Things devices (e.g., smart appliances, etc.), variations or combinations of one or more of the same, and/or any other suitable computing device.

In various implementations, the dental professional system 150 is configured to interface with a dental professional. A "dental professional" (used interchangeably with dentist, orthodontist, and doctor herein) as used herein, may include any person with specialized training in the field of dentistry, and may include, without limitation, general practice dentists, orthodontists, dental technicians, dental hygienists, etc. A dental professional may include a person who can assess, diagnose, and/or treat a dental condition. "Assessment" of a dental condition, as used herein, may include an estimation of the existence of a dental condition. An assessment of a dental condition need not be a clinical diagnosis of the dental condition. In some embodiments, an "assessment" of a dental condition may include an "image based assessment," that is an assessment of a dental condition based in part or on whole on photos and/or images (e.g., images that are not used to stitch a mesh or form the basis of a clinical scan) taken of the dental condition. A "diagnosis" of a dental condition, as used herein, may include a clinical identification of the nature of an illness or other problem by examination of the symptoms. "Treatment" of a dental condition, as used herein, may include prescription and/or administration of care to address the dental conditions. Examples of treatments to dental conditions include prescription and/or administration of brackets/wires, clear aligners, and/or other appliances to address orthodontic conditions, prescription and/or administration of restorative elements to address bring dentition to functional and/or aesthetic requirements, etc. The dental professional system 150 may provide to a user software (e.g., one or more webpages, standalone applications (e.g., dedicated treatment planning and/or treatment visualization applications), mobile applications, etc.) that allows the user to interact with users (e.g., users of the dental consumer/patient system 102, other dental professionals, etc.), create/modify/manage treatment plans (e.g., those from the virtual dental care system 106 and/or those generated at the dental professional system 150), etc.

Virtual dental care system 106 generally represents any type or form of computing device that is capable of storing and analyzing data. Virtual dental care system 106 may include a backend database server for storing patient data and treatment data. Additional examples of virtual dental care system 106 include, without limitation, security servers, application servers, web servers, storage servers, and/or database servers configured to run certain software applications and/or provide various security, web, storage, and/or database services. Although illustrated as a single entity in FIG. 1A, virtual dental care system 106 may include and/or represent a plurality of servers that work and/or operate in conjunction with one another.

As illustrated in FIG. 1A, dental consumer/patient system 102, virtual dental care system, 106, and/or dental professional system 150 may include one or more memory devices, such as memory 140. Memory 140 generally represents any type or form of volatile or non-volatile storage device or medium capable of storing data and/or computer-readable instructions. In one example, memory 140 may store, load, execute in conjunction with physical processor(s) 130, and/or maintain one or more of virtual dental care modules 108. Examples of memory 140 include, without limitation, Random Access Memory (RAM), Read Only Memory (ROM), flash memory, Hard Disk Drives (HDDs), Solid-State Drives (SSDs), optical disk drives, caches, variations or combinations of one or more of the same, and/or any other suitable storage memory.

As illustrated in FIG. 1A, dental consumer/patient system 102, dental professional system 150, and/or server 106 may also include one or more physical processors, such as physical processor(s) 130. Physical processor(s) 130 generally represents any type or form of hardware-implemented processing unit capable of interpreting and/or executing computer-readable instructions. In one example, physical processor(s) 130 may access and/or modify one or more of virtual dental care modules 108 stored in memory 140. Additionally or alternatively, physical processor 130 may execute one or more of virtual dental care modules 108 to facilitate preamble phrase. Examples of physical processor(s) 130 include, without limitation, microprocessors, microcontrollers, Central Processing Units (CPUs), Field-Programmable Gate Arrays (FPGAs) that implement softcore processors, Application-Specific Integrated Circuits (ASICs), portions of one or more of the same, variations or combinations of one or more of the same, and/or any other suitable physical processor.

In some embodiments, dental consumer/patient system 102 may include a camera 132. Camera 132 may comprise a camera, scanner, or other optical sensor. Camera 132 may include one or more lenses or may, one or more camera devices, and/or one or more other optical sensors. In some examples, camera 132 may include other sensors and/or devices which may aid in capturing optical data, such as one or more lights, depth sensors, etc. In various implementations, the camera 132 is not a clinical scanner.

Computer-readable medium 104 generally represents any transitory or non-transitory computer-readable medium or architecture capable of facilitating communication or data transfer. In one example, computer-readable medium 104 may facilitate communication between dental consumer/patient system 102, dental professional system 150, and/or virtual dental care system 106. In some implementations, computer-readable medium 104 comprises a computer network that facilitates communication or data transfer using wireless and/or wired connections. Examples of computer-readable medium 104 include, without limitation, an intranet, a Wide Area Network (WAN), a Local Area Network (LAN), a Personal Area Network (PAN), the Internet, Power Line Communications (PLC), a cellular network (e.g., a Global System for Mobile Communications (GSM) network), portions of one or more of the same, variations or combinations of one or more of the same, and/or any other suitable network. Computer-readable medium 104 may also comprise a connection between elements inside a single device (e.g., a bus, any communications infrastructure (e.g., communications infrastructure 1912 shown in FIG. 19, etc.).

Virtual dental care datastore(s) 120 include one or more datastore configured to store any type or form of data that may be used for virtual dental care. In some embodiments, the virtual dental care datastore(s) 120 include, without limitation, patient data 136 and treatment data 138. Patient data 136 may include data collected from patients, such as patient dentition information, patient historical data, patient scans, patient information, etc. Treatment data 138 may include data used for treating patients, such as treatment plans, state of treatment, success of treatment, changes to treatment, notes regarding treatment, etc.

Example system 100 in FIG. 1A may be implemented in a variety of ways. For example, all or a portion of example system 100 may represent portions of example system 200 in FIG. 2, system 600 in FIG. 6, system 1300 in FIG. 13, or system 1600 in FIG. 16.

As will be described in greater detail below, one or more of virtual dental care modules 108 and/or the virtual dental care datastore(s) 120 in FIG. 1A may, (when executed by at least one processor of dental consumer/patient system 102, virtual dental care system 106, and/or dental professional system 150) enable dental consumer/patient system 102, virtual dental care system 106, and/or dental professional system 150 to facilitate providing virtual dental care between a doctor and a patient. "Virtual dental care," as used herein, may include computer-program instructions and/or software operative to provide remote dental services by a health professional (dentist, orthodontist, dental technician, etc.) to a patient, a potential consumer of dental services, and/or other individual. Virtual dental care may comprise computer-program instructions and/or software operative to provide dental services without a physical meeting and/or with only a limited physical meeting. As an example, virtual dental care may include software operative to providing dental care from the dental professional system 150 and/or the virtual dental care system 106 to the computing device 102 over the network 104 through e.g., written instructions, interactive applications that allow the health professional and patient/consumer to interact with one another, telephone, chat etc. "Remote dental care," as used herein, may comprise computer-program instructions and/or software operative to provide a remote service in which a health professional provides a patient with dental health care solutions and/or services. In some embodiments, the virtual dental care facilitated by the elements of the system 100 may include non-clinical dental services, such as dental administration services, dental training services, dental education services, etc.

Figure 1B:
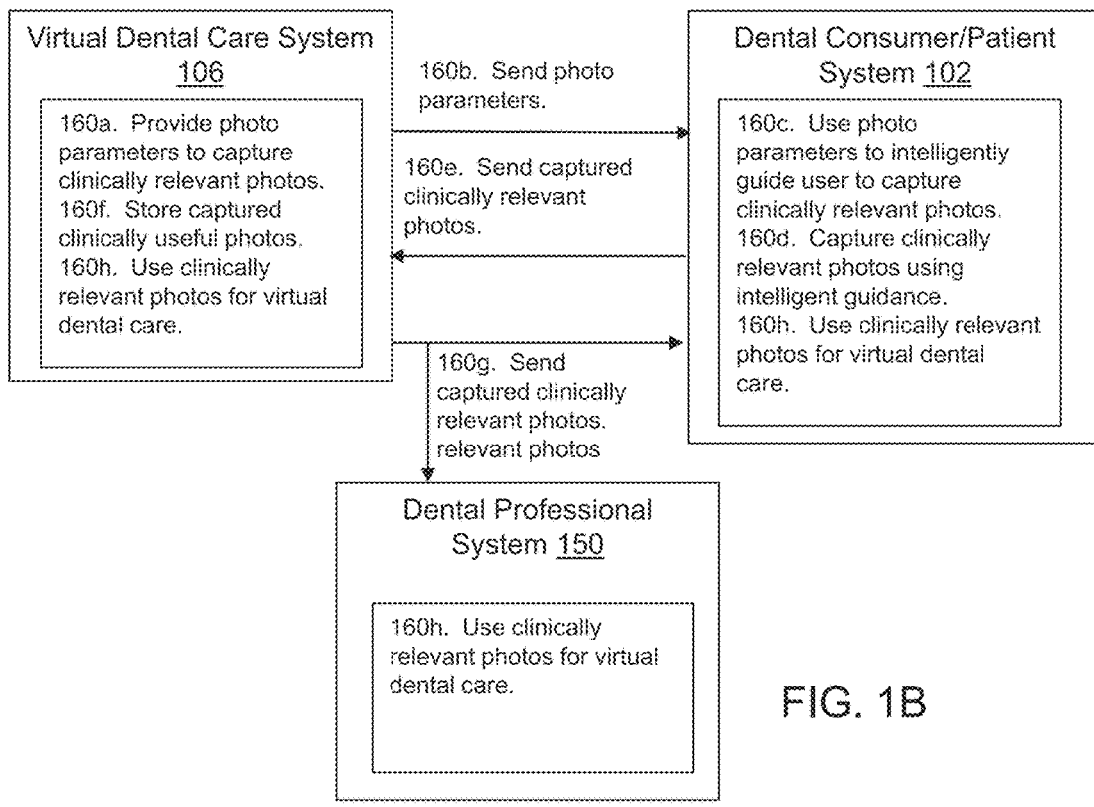
FIG. 1B shows a block diagram of an example system for intelligent photo guidance, in accordance with some embodiments.

In some embodiments, the elements of the system 100 (e.g., the virtual dental care modules 108 and/or the virtual dental care datastore(s) 120) may be operative to provide intelligent photo guidance to a patient to take images relevant to virtual dental care using the camera 132 on the computing device 102. An example of how the elements of the system 100 may operate to provide intelligent photo guidance is shown in FIG. 1B.

At an operation 160*a*, the virtual dental care system 106 may provide one or more photo parameters to capture clinically relevant photos of a user. "Clinically relevant" photos, as used herein, may include images that represent the state of dental conditions in a consumer/patient's dentition. Clinically relevant photos may include photos that are sufficient to provide current position(s) and/or orientation(s) of the teeth in a consumer/patient's mouth. Examples of clinically relevant photos include photos that show all the teeth in a consumer/patient's arch; photos that show the shape of a consumer/patient's arch; photos that show locations of teeth that are missing, supernumerary, ectopic, etc.; photos that show malocclusions in a consumer/patient's arch (e.g., from front, left buccal, right buccal, and/or other various perspectives); etc. "Photo parameters," as used this context, may include parameters to define clinically acceptable criteria (e.g., clinically acceptable position(s) and/or clinically acceptable orientation(s) of teeth) in one or more photos. Photo parameters can include a distance parameters, e.g., one that parametrizes a distance that a camera is relative to a consumer/patient's dentition; orientation parameters (e.g., those that parametrize orientations of photos taken of teeth); openness parameters of a photo of a consumer/patient's bite (e.g., whether a bite is open, closed, and/or a degree of openness of a bite); a dental appliance wear parameter of a photo of a consumer/patient's bite (e.g., whether a photo shows dental appliances, such as cheek retractors, aligners, etc. in a consumer/patient's mouth); camera parameters (brightness parameters of photos; contrast parameters of photos; exposure parameters of photos; etc.); tooth identifier parameters, e.g., those that parametrize the specific teeth in a photo, those taken from a treatment plan; etc. At an operation 160*b*, the virtual care dental system 106 may send the one or more photo parameters to the dental consumer/patient system 102. This operation can occur as a file and/or data transfer over the computer-readable medium 104.

At an operation 160*c*, the dental consumer/patient system 102 may use the one or more photo parameters to intelligently guide the consumer/patient to capture clinically relevant photos of their dentition. The dental consumer/patient system 102 may gather image-capture rules that guide capturing the clinically relevant photos based on the photo parameters. The dental consumer/patient system 102 may provide a consumer/patient with software (e.g., one or more webpages, standalone applications, mobile applications, etc.) that uses the one or more photo parameters to help the consumer/patient capture clinically relevant photos of their teeth. As an example, distance parameters may be used to guide a consumer/patient to position and/or orient the dental consumer/patient system 102 a specific distance away from their teeth to capture a photo with appropriate details of their teeth. The distance parameters may guide whether the position of a camera is too close or too far or just right. Orientation parameters may be used to guide a photo to clinically relevant orientations. As an example, orientation parameters may be used to guide a consumer/patient to take photos of anterior views, left buccal views, right buccal views, etc. As additional examples, openness parameters may be used to guide a consumer/patient to take photos of various bite states, e.g., an open bite, closed bite, and/or a bite that is partially open in order to be clinically relevant; dental appliance wear parameters may be used to detect cheek retractors and/or guide a consumer/patient to position cheek retractors appropriately and/or locate/orient photos to be clinically relevant; dental appliance wear parameters may be used to detect various dental appliances (aligners, retainers, etc.) and guide a consumer to remove, move, etc. the dental appliances for photos that are clinically relevant; etc. Additionally, tooth identifier parameters (e.g., those gathered from a treatment plan) can be used to guide a consumer/patient to take photos of a sufficient number of teeth so that the photos are clinically relevant. Camera parameters, e.g., contrast, brightness, exposure, etc. parameters may be used to guide consumers/patients to take photos that have properties such that the photos are clinically relevant. In some implementations, the dental consumer/patient system 102 uses camera parameters to modify one or more photo settings (add/disable flash, adjust zoom, adjust brightness, adjust contrast, adjust shadows, adjust silhouettes, etc. so that clinically relevant photos are captured under various conditions. As noted herein, the operation 160*c* may be performed by automated agents and without human intervention.

At an operation 160*d*, the dental consumer/patient system 102 may operate to capture clinically relevant photos using the intelligent guidance. In some implementations, a consumer/patient may follow instructions to capture photos of their dentition using the intelligent guidance provided on the dental consumer/patient system 102. In various implementations, at least a part of operation 160*d* is performed by automated agents that configure a camera to take photos without human intervention. At an operation 160*e*, the dental consumer/patient system 102 may send captured clinically relevant images to the virtual dental care system 106. This operation may occur as a file and/or data transfer over the computer-readable medium 104.

At an operation 160*f*, the virtual dental care system 106 may store the captured clinically relevant photos. In various implementations, the virtual dental care system 106 may store the captured clinically relevant photos in a treatment database associated with a consumer/patient, a clinical data file associated with a consumer/patient, and/or in any relevant datastore. At an operation 160*g*, the virtual dental care system 106 may send captured clinically relevant photos to the dental consumer/patient system 102 and/or the dental professional system 150. This operation may occur over a file and/or data transfer over the computer-readable medium 104.

At an operation 160*h*, the dental consumer/patient system 102, the virtual dental care system 106 and/or the dental professional system 150 may use clinically relevant photos for virtual dental care. As an example, the dental professional system 150 may display to the consumer/patient instructions in the form of an overlay over an image of the consumer/patient's teeth. As an other example, the dental professional system 150 may display to the consumer/patient verbal and/or interactive instructions on how to modify and/or improve capture of a clinically relevant photo. In some implementations, the dental consumer/patient system 102, the virtual dental care system 106 and/or the dental professional system 150 may, e.g., use clinically relevant photos for image-based assessments, intelligent patient guidance, and/or photo-based refinements.

Figure 1C:
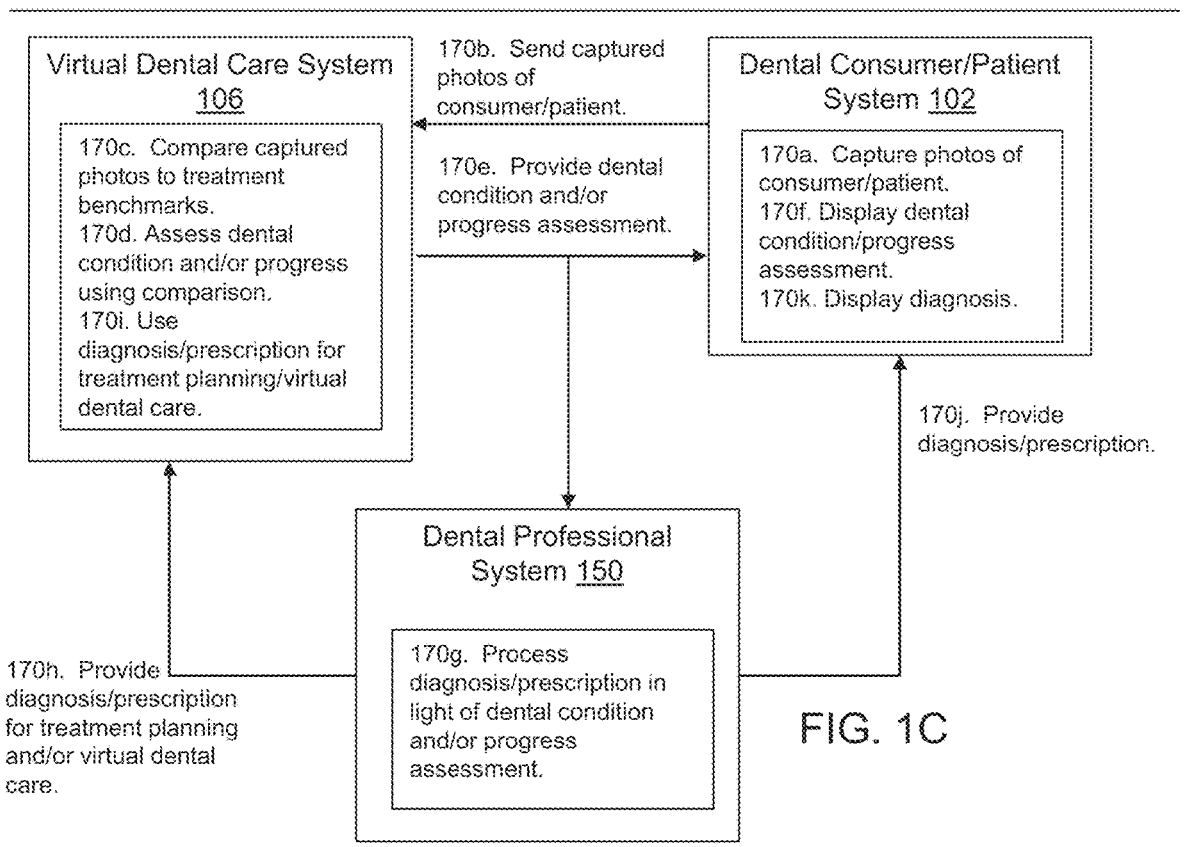
FIG. 1C shows a block diagram of an example system for image-based assessment, in accordance with some embodiments.

In some embodiments, the elements of the system 100 (e.g., the virtual dental care modules 108 and/or the virtual dental care datastore(s) 120) may be operative to provide one or more image-based assessment tools to the users of the dental professional system 150. "Image based assessment tools," as used herein, may include digital tools that operate to provide image-based assessments of a dental condition. In some embodiments, image-based assessments may comprise visualizations that allow a user of the dental professional system 150 to make a decision about a clinical condition. For instance, the elements of the system 100 may provide visualizations that assist a user of the dental professional system 150 with one or more diagnoses of a dental condition. As noted herein, visualizations may include, e.g., visualizations of assessments of a current stage of a treatment plan; visualizations of assessments may, but need not, be based on images and knowledge of a treatment plan that is underway. As another example, the elements of the system 100 may provide visualizations to a user of the dental professional system 150 that provide a view of a patient's assessment over time. An example of how the elements of the system 100 may operate to provide image-based assessment tools is shown in FIG. 1C.

At an operation 170a, the dental consumer/patient system 102 may capture one or more images of a consumer/patient. The one or more images may comprise photos taken by the camera of the dental consumer/patient system 102. The one or more photos may be captured by intelligent photo guidance techniques described further herein. The one or more images may include various perspectives and/or views of the dentition of the consumer/patient. The one or more photos captured at operation 170a need not include scan data, height map information, and/or data a clinical scanner uses to stitch together a mesh representation of consumer/patient's dentition. The dental consumer/patient system 102 may store images captured locally, in a networked folder, etc. At an operation 170b, the dental consumer/patient system 102 may send captured photos of the consumer/patient to the virtual dental care system 106. This operation may include a file and/or other data transfer over the computer-readable medium 104.

At an operation 170c, the virtual dental care system 106 may compare the captured photos to one or more treatment benchmarks. "Treatment benchmarks," as used herein, may include one or more standards or reference points of at least part of a treatment plan. Treatment benchmarks may include intended positions of teeth, jaws, palatal regions, etc. of dentition at a specific stage of a treatment plan. In some implementations, treatment benchmarks are represented as intended positions of a specific stage of a treatment plan on a 3D model of a patient's dentition. In various implementations, treatment benchmarks correspond to representations of a patient's dentition from which to assess a dental condition. As examples, treatment benchmarks may represent a variety of malocclusions for which the consumer/patient is to be assessed. At an operation 170d, the virtual care dental system 106 may assess a dental condition and/or progress of a treatment plan using the comparison of the captured photos and the treatment benchmarks. As noted herein, the assessment need not comprise a diagnosis of the dental condition and/or the progress through the treatment plan.

At an operation 170e, the virtual dental care system 106 may provide the dental consumer/patient system 102 and/or the dental professional system 150 the assessed dental condition and/or the progress assessment. This operation may occur as a file and/or data transfer over the computer-readable medium 104. The dental consumer/patient system 102 and/or the dental professional system 150 may perform additional operations with the assessed dental condition and/or the progress assessment. As one example, the dental consumer/patient system 102 may, at an operation 170f, display the dental condition and/or the progress assessment. For instance, the dental consumer/patient system 102 may display, e.g., in an application and/or in webpages, user interface elements (annotated 3D models, annotated images, informative and/or interactive user interface elements, etc.) that show an assessment to a consumer/patient.

As another example, the dental professional system 150 may, in an operation 170g, process a diagnosis and/or prescription for a consumer/patient using the dental condition and/or progress assessment. In the operation 170g, the diagnosis may also be based on one or more clinical images (intraoral scans, x-rays, CBCT scans, etc.) of the consumer/patient's dentition. In some implementations, a doctor may use software on the dental professional system 150 to perform a diagnosis of a dental condition and/or of progress of a treatment plan. As an example, a doctor may use treatment planning software on the dental professional system 150 to diagnose malocclusions and/or other dental conditions reflected in the photos from the consumer/patient. Instructions corresponding to the diagnosis may be processed by the dental professional system 150. In various implementations, a dental professional may provide a prescription to treat one or more dental conditions. As an example, a dental professional may prescribe through the dental professional system 150 one or more dental appliances (clear aligners, orthodontic appliances, restorative appliances, etc.) to treat dental conditions that are associated with the dental condition and/or progress assessment. For an initial assessment, the prescription may comprise an initial prescription for dental appliances. For a progress assessment, the prescription may comprise corrective dental appliances that are configured to correct deviation(s) from a treatment plan.

At an operation 170h, the dental professional system 150 may provide the diagnosis and/or prescription for treatment planning and/or virtual dental care to the virtual dental care system 106. At an operation 170i, the virtual care dental system 106 may use the diagnosis/prescription for treatment planning and/or virtual dental care. At an operation 170j, the dental professional system 150 may provide the diagnosis and/or prescription to the dental consumer/patient system 102. At an operation 170k, the dental consumer/patient system 102 may display the diagnosis to the consumer/patient.

In some embodiments, the elements of the system 100 (e.g., the virtual dental care modules 108 and/or the virtual dental care datastore(s) 120) may be operative to provide intelligent patient guidance to consumers/patients that use the dental consumer/patient system 102. "Intelligent patient guidance," as used herein, may include instructions to guide a consumer/patient to take one or more actions. In some implementations, the elements of the system 100 generate intelligent patient guidance using photos of a consumer/patient, treatment parameters supplied by a doctor, and/or other information.

In some implementations, intelligent patient guidance is supplied by automated agents without intervention (or with minimal intervention, e.g., a doctor providing treatment parameters and/or interacting with a guidance template). Intelligent patient guidance may include: e.g., instructions to change (and/or when to change) a specific dental appliance (e.g., an aligner, a retainer, etc.); instructions to continue use (and/or when to continue use) of a dental appliance in relation to a subsequent dental appliance, instructions to use (and/or a location of use) of a supplemental dental appliance (e.g., chewie, mint, etc.); instructions to direct attention to a region of a consumer/patient's dentition (anterior portions, posterior portions, portions that are likely to move during a specific stage, portions that anchor various tooth movements, etc.); instructions to notify a doctor at a specific time or in response to a specific event (e.g., teeth moving at a specific time, teeth moving in accordance with a specific movement pattern, etc.); instructions to capture one or more images of a consumer/patient's dentition for the purpose of progress tracking at a specified time/treatment stage; instructions to the consumer/patient to visit a doctor, set an appointment, or take other action in relation to a doctor; etc. As noted herein, intelligent patient guidance can include any combination and/or variations of the foregoing examples.

Intelligent patient guidance may accommodate deconfliction, e.g., may be determined based on prioritizing some forms of action and/or removing some conflicting forms of action from guidance. Guidance Rules may provide a set of conflicting or prioritized guidance to the patient. E.g., use a chewie (due to one rule) and set an appointment (due to another) and have the system alert the doctor (due to a third rule); in a case such as this, only a alert to a doctor rule might be activated because the doctor may override the other rules. Another example might be the rules indicating the use of a chewie on the first premolar and another rule indicating a chewie on the second premolar on the same side—clearly only one chewie is needed. Deconfliction may ensure that patient is provided with only relevant guidance.

Intelligent patient guidance supplied by the elements of the system 100 may be based on a dental condition and/or progress assessment (e.g., one reflected by images captured by a consumer/patient), treatment parameters, etc. "Treatment parameters," as used herein, may include a set of parameters that are used to specify attributes of a treatment plan to apply to a consumer/patient. Treatment parameters may include doctor-preference parameters, e.g., treatment parameters specifying treatment protocols that a doctor (and/or other doctors, e.g., those whose treatment protocols are used by a specific doctor) would prescribe for various patients and/or clinical conditions. Treatment parameters may include per-patient parameters, e.g., parameters used to specify treatment protocols for a specific consumer/patient. Per-patient parameters may be based on attributes of a consumer/patient (past treatments, anatomical information (attributes of specific dentitions, jaws, etc.), etc. Per-patient parameters need not be based on attributes of a specific consumer/patient, and, e.g., may include demographic information (information related to the consumer/patient's race, gender, age, etc.), information about historically treated cases (e.g., those with similar forms of dental conditions to the consumer/patient) information about idealized dental arches (e.g., those related to dental arches with idealized/near-idealized occlusions as defined by treatment professionals), and/or other information.

Figure 1D:
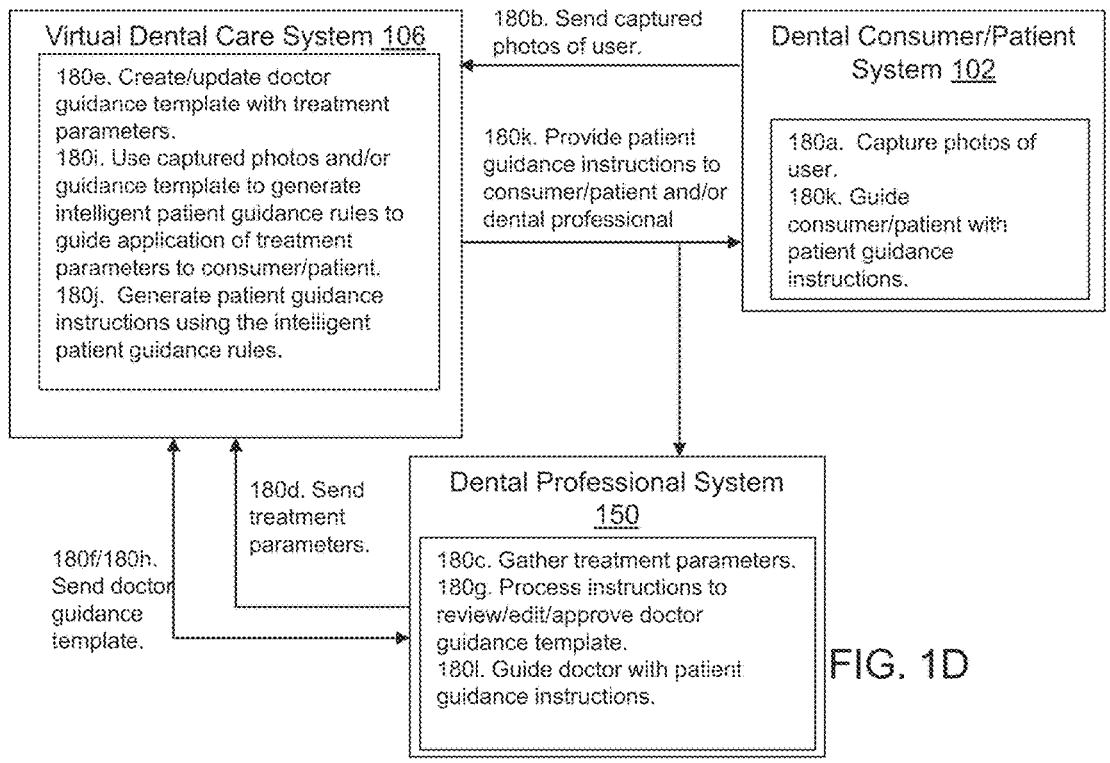
FIG. 1D shows a block diagram of an example system for intelligent patient guidance, in accordance with some embodiments.

In some implementations, the elements of the system 100 may utilize a doctor guidance template, which, as used herein, may include a formatted data structure that specifies a set of rules that a doctor can use for tracking a treatment plan. Examples of rules could be as specific as central incisors deviations from the treatment plan of 0.75 millimeters (mm) should result in a new appointment; central incisor deviations of 0.5-0.75 mm should be watched; central incisor deviations that increase over a period of two (2) months should result in a new appointment; central incisor deviations of 0.25 to 0.5 mm should wear the current set of aligners for an additional week; and central incisor deviations less than 0.25 mm can be considered "on-track". Other rules may specify that teeth marked "Do No Move" should not deviate from their treatment position and any deviation greater than 0.25 mm should result in an appointment. Rules in a doctor guidance template may allow conditionals based on a treatment plan and/or other factors. In some implementations, rules in a doctor guidance template may be written with a temporal frame of reference and/or based on patient historical data (e.g., historical information about patient guidance provided to a consumer/patient in the past and/or historical measurement information). An example of how the elements of the system 100 may operate to provide intelligent patient guidance is shown in FIG. 1D.

At an operation 180a, the dental consumer/patient system 102 may capture one or more images of a consumer/patient. The one or more images may comprise photos taken by the camera of the dental consumer/patient system 102. The one or more photos may be captured by intelligent photo guidance techniques described further herein. The one or more images may include various perspectives and/or views of the dentition of the consumer/patient. The one or more photos captured at operation 180a need not include scan data, height map information, and/or data a clinical scanner uses to stitch together a mesh representation of consumer/patient's dentition. The one or more photos may reflect a state of a treatment plan that is intended for and/or is underway on the consumer/patient. As an example, the one or more photos may capture an initial assessment of the consumer/patient's dentition and/or reflect the patient's progress at a specified stage of a treatment plan. The dental consumer/patient system 102 may store images captured locally, in a networked folder, etc. At an operation 180b, the dental consumer/patient system 102 may send captured photos of the consumer/patient to the virtual dental care system 106. This operation may include a file and/or other data transfer over the computer-readable medium 104.

At an operation 180c, the dental professional system 150 may gather treatment parameters for the consumer/patient. As noted herein, the treatment parameters may include doctor-preference parameters, per-patient parameters, etc. At an operation 180d, the dental professional system 150 may send the treatment parameters to the virtual dental care system 106. This operation may include a file and/or transfer over the computer-readable medium 104. As noted herein, the treatment parameters may comprise doctor-preference parameters and/or per-patient parameters.

At an operation 180e, the virtual dental care system 106 may create and/or update a doctor guidance template with treatment parameters. As noted herein, the doctor guidance template may supply a template with one or more rules that a doctor can use to track implementation of a treatment plan to a consumer/patient. The doctor guidance template may accommodate one or more rules to perform guidance deconfliction and/or prioritize various forms of action given doctor preferences, patient attributes, etc. The virtual dental care system 106 may store a doctor guidance template in any relevant format, including but not limited to any transitory and/or non-transitory medium. The virtual dental care system 106 may, in an operation 180f, send a doctor guidance template to the dental professional system 150.

At an operation 180g, the dental professional system 150 may process instructions to review, edit, and/or approve a doctor guidance template. In some implementations, the dental professional system 150 may provide a doctor with a user interface and/or other software that allows the doctor to review doctor guidance templates, make any changes to a doctor guidance template, and/or approve/finalize a doctor guidance template so that it can be applied to a specific patient, such as the consumer/patient using the dental consumer/patient system 102. As an example, in some implementations, a doctor may provide instructions to override a specific part of a doctor guidance template based on one or more factors, such as factors related to specific attributes of a specific consumer/patient. The dental professional system 150 may, in an operation 180h, send a reviewed/edited/approved doctor guidance template to the virtual dental care system 106. This operation may occur as a file and/or data transfer over the computer-readable medium 104.

At an operation 180i, the virtual dental care system 106 may use the captured photos and optionally the guidance template to generate intelligent patient guidance rules (e.g., rules that guide application of the treatment parameters to the consumer/patient). In some implementations, the virtual care dental system 106 may use the captured photos that were captured at the dental consumer/patient system 102 and a doctor guidance template reviewed, edited, and/or approved by the dental professional system 150 to generate intelligent patient guidance rules for the consumer/patient. At an operation 180j, the virtual care dental system 106 can generate patient guidance instructions using the intelligent patient guidance rules. Patient guidance instructions may take the form of instructions to the consumer/patient to take specific actions (add/change a dental appliance, wear a dental appliance longer or shorter than initially prescribed), may take the form of instructions to modify appointments and/or tasks, and/or may take the form of instructions to interact with the doctor in new and/or modified ways (e.g., draw attention to an area of dentition that is of increased interest).

At an operation 180k, the virtual dental care system 106 may provide patient guidance instructions to the dental consumer/patient system 102 and/or the dental professional system 150. This operation may occur as a file and/or data transfer over the computer-readable medium 104.

At an operation 180k, the dental consumer/patient system 102 may guide a consumer/patient using patient guidance instructions. In various implementations, the dental/consumer system 102 may present a consumer/patient with automated and/or interactive software elements that instruct the consumer/patient to take specified actions in relation to their treatment plans. As noted herein, example actions include instructions to change a dental appliance, instructions to keep a dental appliance beyond an initially prescribed time, use a supplemental dental appliance at a specific time/location, set an appointment for a specific condition and/or at a specific time/place, etc. At an operation 180l, the dental professional system 150 may guide the doctor with patient guidance instructions. In various implementations, the dental professional system 150 may present a doctor with automated and/or interactive software elements that, e.g., set appointments for a patient, notify a doctor about one or more conditions and/or regions of a consumer/patient's dentition to focus on, etc.

Figure 1E:
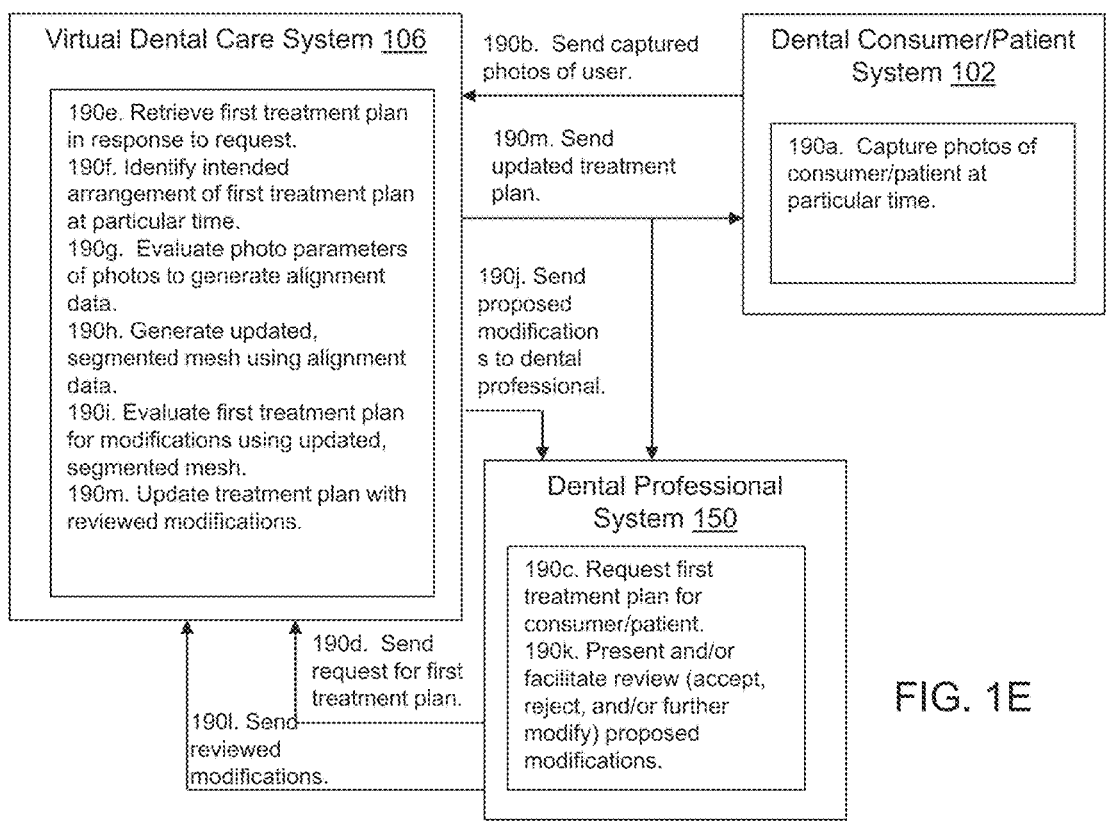
FIG. 1E shows a block diagram of an example system for photo-based refinement, in accordance with some embodiments.

In some embodiments, the elements of the system 100 (e.g., the virtual dental care modules 108 and/or the virtual dental care datastore(s) 120) may be operative to provide photo-based refinements to users of the dental professional system 150. "Photo-based refinements," as used herein, may include tools that allow a doctor performing virtual dental care to prescribe orders for consumers/patients whose treatments deviate from an intended course of treatment. The tools may use photos and may avoid requirements to rescan (e.g., perform a second and/or subsequent clinical scan after an initial clinical scan) the consumer/patient and/or provide a live evaluation of the consumer/patient, e.g., at the doctor's office. In some implementations, photo-based refinements may provide tools for a doctor to create a secondary (e.g., a refined) treatment plan remotely without ever physically seeing and/or evaluating a consumer/patient. Photo-based refinements may optimize one or more camera parameters to align a consumer/patient's treatment plan to photos captured by/for the consumer/patient. Photo-based refinements may also optimize one or more pose parameters (e.g., location parameters, orientation parameters, etc.) of a consumer/patient's teeth to ensure the teeth are in appropriate spaces. As noted herein, photo-based refinements may be displayed to doctors as user interface elements (e.g., overlays) representing a consumer/patient's dentition in relation to a treatment plan. Photo-based refinements can be used to plan one or more refinement treatment plans using 3D tooth shapes from a primary treatment plan and/or locations found using the techniques described herein; as noted herein, this information may be used to plan one or more new/refined treatment plans. An example of how the elements of the system 100 may operate to provide photo-based refinements is shown in FIG. 1E.

At an operation 190a, the dental consumer/patient system 102 may capture one or more images of a consumer/patient at a particular time, e.g., at one or more time during the course of virtual dental care. The one or more images may comprise photos taken by the camera of the dental consumer/patient system 102. The one or more photos may be captured by intelligent photo guidance techniques described further herein. The one or more images may include various perspectives and/or views of the dentition of the consumer/patient. As an example, the one or more images may include a plurality of images that represent more than one perspective of the consumer/patient's dentition. For instance, the images may be taken from anterior, left buccal, right buccal, and/or other perspectives. As noted herein, the one or more images may be captured as the consumer/patient is intelligently guided to take photos of their dentition. The one or more photos captured at operation 190a need not include scan data, height map information, and/or data a clinical scanner uses to stitch together a mesh representation of consumer/patient's dentition. The one or more photos may reflect a state of a treatment plan that is intended for and/or is underway on the consumer/patient. As an example, the one or more photos may capture an initial assessment of the consumer/patient's dentition and/or reflect the patient's progress at a specified stage of a treatment plan. The dental consumer/patient system 102 may store images captured locally, in a networked folder, etc. At an operation 190b, the dental consumer/patient system 102 may send captured photos of the consumer/patient to the virtual dental care system 106. This operation may include a file and/or other data transfer over the computer-readable medium 104.

At an operation 190c, the dental professional system 150 may request a first treatment plan for the consumer/patient. In some implementations, a doctor may, through instructions provided to the dental professional system 150, request a first treatment plan for a consumer/patient. The first treatment plan may comprise any set of instructions to address a dental condition of the consumer/patient. As an example, the first treatment plan may include instructions to move a consumer/patient's teeth from a first arrangement toward a target arrangement. The first treatment plan may prescribe use of successive dental appliances (e.g., a plurality of successive aligners shaped to receive and resiliently reposition a consumer/patient's teeth from the initial arrangement toward the target arrangement). The first treatment plan may include restoring attributes of a consumer/patient's dentition using crowns, bridges, implants, and/or other restorative dental appliances. In various implementations, the first treatment plan is based on a clinical scan, such as a clinical scan that occurred before the operation 190a.

At an operation 190d, the dental professional system 150 may send the request for the first treatment plan to the virtual dental care system 106. This operation may occur as a file and/or data transfer over the computer-readable medium 104.

At an operation 190e, the virtual dental care system 106 may retrieve the first treatment plan in response to the request for the first treatment plan. Retrieving the first treatment plan may involve providing instructions to a treatment datastore to retrieve a clinical data file associated with a consumer/patient. The clinical data file may represent an initial position of the consumer/patient's dentition, an intended target position of the consumer/patient's dentition, and/or a plurality of intermediate positions to move the consumer/patient's dentition from the initial position toward the intended target position. In some implementations, the clinical data file may include specific clinical preferences (stage(s) at which interproximal reduction (IPR) was performed, locations and/or times of application of attachments applied during the first treatment plan, etc.). The clinical data file may also include clinical preferences of the doctor who managed prescription of the first treatment plan as well as specific attributes of dental appliances used to implement the first treatment plan.

At an operation 190f, the virtual dental care system 106 may identify an intended arrangement of a first treatment plan at the particular time that the photos of the consumer/patient were taken at the dental consumer/patient system 102. The virtual dental care system 106 may, e.g., use a length of time since initial implementation of the first treatment plan, spatial relationships between teeth in the photos captured at the dental consumer/patient system 102, and/or other information to identify the stage of the first treatment plan at which the photos were captured at the dental consumer/patient system 102. The virtual dental care system 106 may further evaluate a file that represents the intended arrangement of the identified stage of the first treatment plan to identify 3D structures, e.g., meshes corresponding to the identified stage of the first treatment plan.

At an operation 190g, the virtual dental care system 106 may evaluate photo parameters of the photos captured at the dental consumer/patient system 102 to generate alignment data, e.g., data representing an alignment of the intended arrangement of the first treatment plan to the photos. In some implementations, the virtual dental care system 106 optimizes 3D parameters from the images captured at the dental consumer/patient system 102. Examples of 3D parameters that may be optimized include camera parameters, location parameters, orientation parameters, etc. 3D parameter optimization may be performed using a variety of techniques, such as differential rendering, expectation maximization, etc. Applicant hereby incorporates by reference the following applications as if set forth fully here: U.S. Pat. App. Ser. No. 62/952,850, U.S. patent application Ser. No. 16/417,354; US Pat. App. Ser. No. 16/400,980; US Pat. App. Ser. No. 16/455,441; and U.S. patent application Ser. No. 14/831,548 (now U.S. patent Ser. No. 10/248,883). Once photo parameters are evaluated/optimized, the virtual dental care system 106 may use those photo parameters to determine places where the consumer/patient's teeth are not tracking to the first treatment plan. For instance, the virtual dental care system 106 may evaluate where the consumer/patient's teeth are in intended locations/orientations as well as where teeth deviate from intended locations/orientations.

At an operation 190h, the virtual care dental system 106 may generate an alignment mesh (e.g., an updated, segmented mesh) using the alignment data. The alignment mesh may comprise a 3D representation of the consumer/patient's dentition that reflects the photos taken at the consumer/patient system 102. At an operation 190i, the virtual care dental system 106 may evaluate the first treatment plan for modifications using the alignment mesh. The virtual dental care system 106 may identify locations where the consumer/patient's teeth are off-track and/or deviating from an intended arrangement prescribed by the first treatment plan. The virtual dental care system 106 may store any modifications in a clinical data file associated with the consumer/patient. At an operation 190j, the virtual dental care system 106 may send proposed modifications to a doctor. This operation may occur as a file and/or data transfer over the computer-readable medium 104.

At an operation 190k, the dental professional system 150 may present and/or facilitate review of proposed modifications to the doctor. In various implementations, the dental professional system 150 shows a doctor the proposed modifications on a 3D model and/or images representing the consumer/patient's dentition. The dental professional system 150 may further allow the doctor to accept, reject, and/or further modify the 3D model and/or the images. As an example, the dental professional system 150 may allow the doctor to further move positions of attachments, modify aligners and/or force systems, modify stages at which IPR is performed, etc. At an operation 190l, the dental professional system 150 may send reviewed modifications to the virtual dental care system 106, e.g., as a file and/or data transfer over the computer-readable medium 104. At an operation 190m, the virtual dental care system 106 may update the first treatment plan with the reviewed modifications. In various implementations, the virtual dental care system 106 updates a clinical data file associated with the consumer/patient with the reviewed modifications.

For example, and as will be described in greater detail below, one or more of virtual dental care modules 108 may cause dental consumer/patient system 102, the dental professional system, 150, and/or the virtual dental care system 106 to recite steps of method claim using one or more of FIGS. 3, 7, 14, 15, and/or 17.

Intelligent Photo Guidance

To perform virtual orthodontic care, virtual dental care, and/or other remote medicine, the practitioner may wish to visually inspect the patient. For example, the practitioner may wish to inspect the patient's progress during a treatment plan, diagnose possible issues, and modify the treatment plan as needed. The availability of high-resolution cameras, for instance integrated with smartphones, allows patients to take sufficiently high-resolution photos that may enable the practitioner to inspect patients. However, patients may not know how to properly frame the clinically relevant body parts for the practitioner to inspect. For example, an orthodontic practitioner may require specific views of specific teeth of the patient. The patient may not be aware of which specific teeth to capture, which angles to take photos, whether to wear oral appliances, etc.

As will be described further below, the systems and methods provided in this disclosure may utilize artificial intelligence to provide a patient with guidance on taking clinically relevant orthodontic photos. The systems and methods provided in this disclosure may improve the functioning of a computing device by more efficiently acquiring image data, which may further reduce storage requirements and network bandwidth. In addition, the systems and methods provided herein may improve the field of virtual medicine by improving the functional capabilities of remote devices. Moreover, the systems and methods provided herein may improve the field of medical imaging by providing a near-real-time classification of images for various classifiers.

Figure 2:
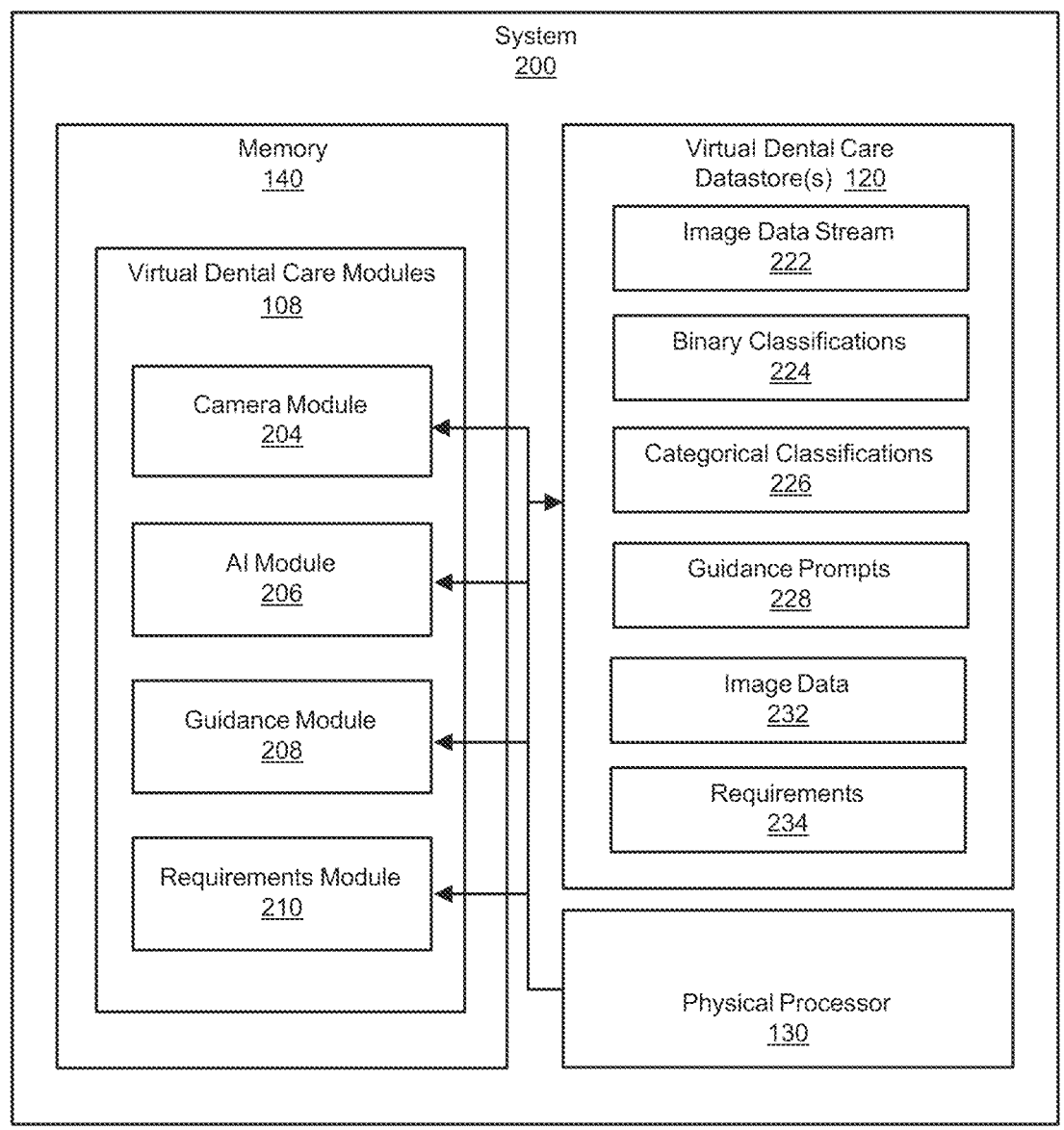
FIG. 2 shows a block diagram of an example system for photo guidance, in accordance with some embodiments.

FIG. 2 is a block diagram of an example system 200 for artificial intelligence (AI) assisted photo guidance. As illustrated in this figure, example system 200 may include one or more virtual dental care modules 108 for performing one or more tasks. As will be explained in greater detail below, virtual dental care modules 108 may include a camera module 204, a AI module 206, a guidance module 208, and a requirements module 210. Although illustrated as separate elements, one or more of virtual dental care modules 108 in FIG. 2 may represent portions of a single module or application.

In certain embodiments, one or more of virtual dental care modules 108 in FIG. 2 may represent one or more software applications or programs that, when executed by a computing device, may cause the computing device to perform one or more tasks. For example, and as will be described in greater detail below, one or more of virtual dental care modules 108 may represent modules stored and configured to run on one or more computing devices, such as the devices illustrated in FIG. 1A (e.g., computing device 102 and/or server 106). One or more of virtual dental care modules 108 in FIG. 2 may also represent all or portions of one or more special-purpose computers configured to perform one or more tasks.

As illustrated in FIG. 2, example system 200 may also include one or more virtual dental care datastore(s) 120, such as an image data stream datastore 222, binary classifications datastore 224, categorical classifications datastore 226, guidance prompts datastore 228, image data 232, and requirements data 234. Virtual dental care datastore(s) 120 may comprise one or more datastores configured to store any type or form of data or information.

Figure 3:
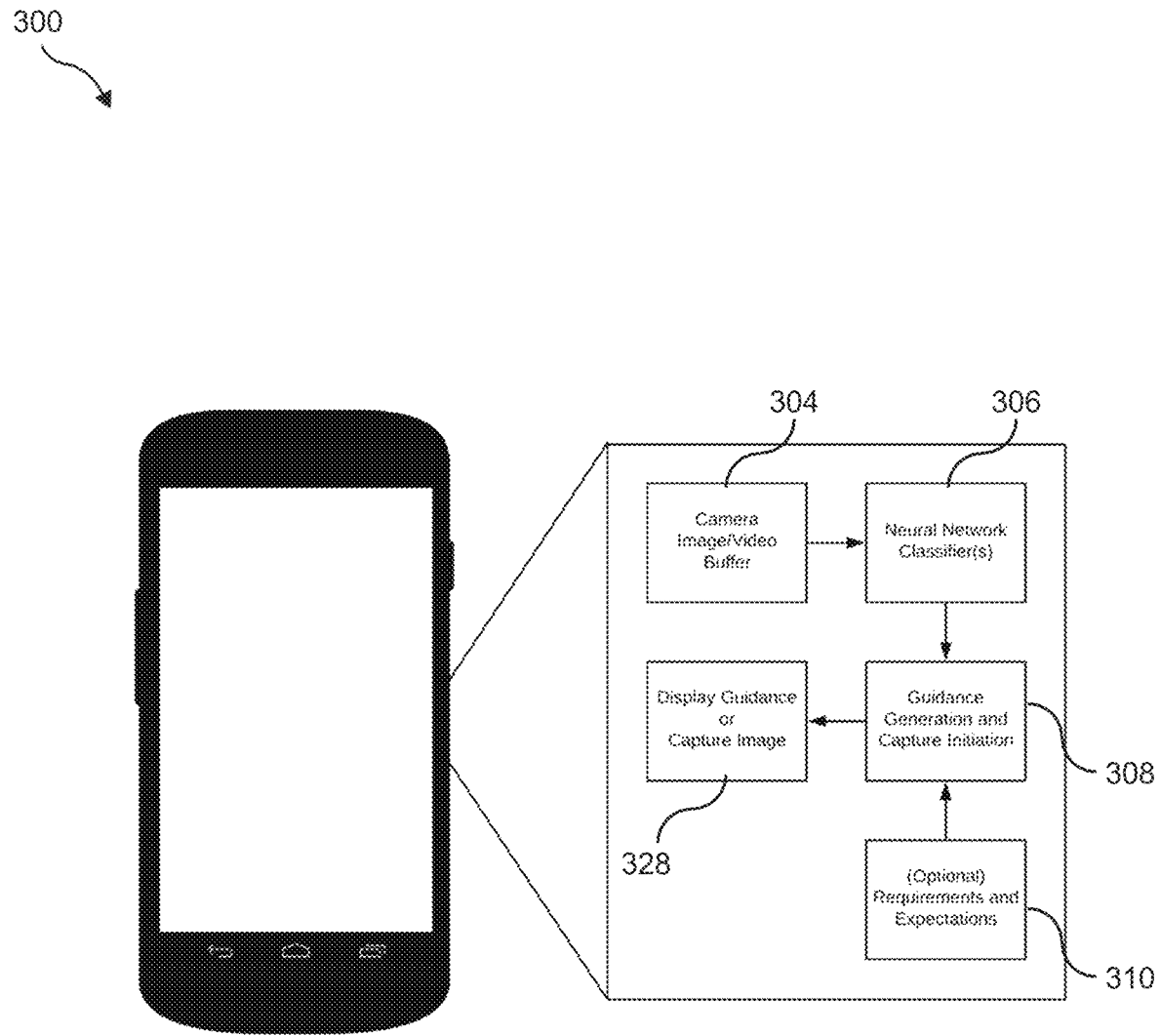
FIG. 3 shows a flow diagram of example method for photo guidance, in accordance with some embodiments.

FIG. 3 is a flow diagram of an exemplary computer-implemented method 300 for AI-assisted photo guidance. The steps shown in FIG. 3 may be performed by any suitable computer-executable code and/or computing system, including the system(s) illustrated in FIGS. 1 and 2. In one example, each of the steps shown in FIG. 3 may represent an algorithm whose structure includes and/or is represented by multiple sub-steps, examples of which will be provided in greater detail below.

As illustrated in FIG. 3, at step 302 one or more of the systems described herein may receive an image data stream from a camera. For example, camera module 204 may receive image data stream 222 from camera 132 of system 200 or another camera in communication with system 200.

In some embodiments, the term "image data stream" may refer to optical capture data which may be temporarily stored in a buffer (e.g., a camera buffer) or otherwise saved in a device memory. Examples of image data streams include, without limitation, one or more photos, video, etc. An image data stream may include additional sensor data, such as depth data.

The systems described herein may perform step 302 in a variety of ways. In one example, camera module 204 may receive image data stream 222 from a buffer of camera 132. Image data stream 222 may be image data temporarily stored, such as image data corresponding to a viewfinder of camera 132. In other examples, image data stream 222 may include captured and stored images.

Figure 4:
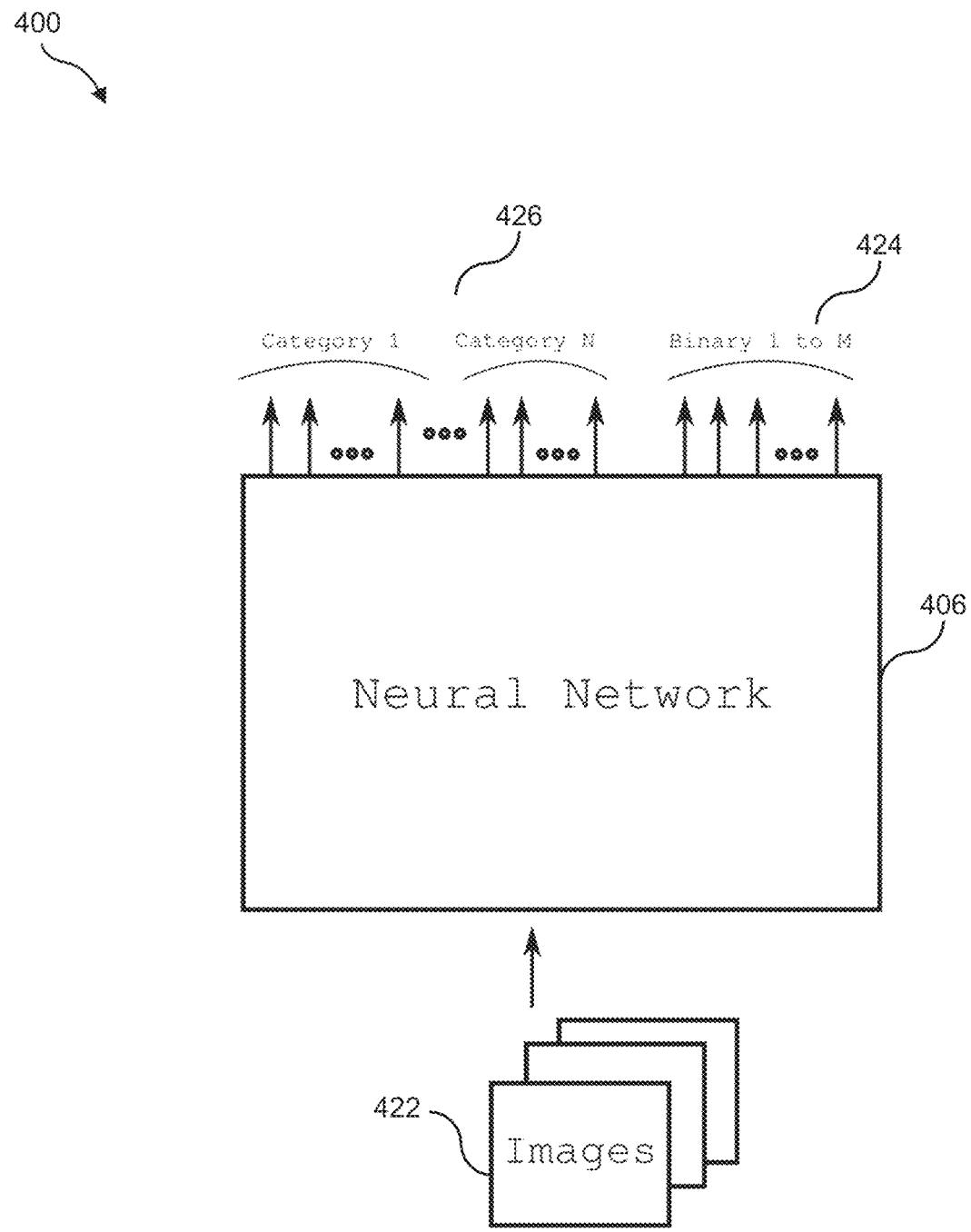
FIG. 4 shows an example user device for photo guidance, in accordance with some embodiments.

FIG. 4 illustrates data flow of a device 400, which may correspond to system 200 and/or computing device 102. At 404, a camera image/video buffer may temporarily store image data (e.g., image data stream 222). Image data stream 222 may be raw image and/or video data, or may be processed. For example, image data stream 222 may be corrected for any visual artefacts, compressed and/or decompressed, reformatted and/or resized for further processing, etc.

Returning to FIG. 3, at step 304 one or more of the systems described herein may determine, using an artificial intelligence scheme, one or more binary classifications and one or more categorical classifications from the image data stream. For example, AI module 206 may determine binary classifications 224 and categorical classifications 226 from image data stream 222.

In some embodiments, the term "binary classification" may refer to characteristics that may be defined as having one of two states (e.g., yes or no). With respect to the image data stream, examples of binary classifications may include, without limitation, whether a particular tooth is visible, whether a particular group of teeth are visible (e.g., posterior teeth, etc.), whether an upper jaw is visible, whether a lower jaw is visible, whether an appliance (e.g., an aligner, a cheek retractor, etc.) is visible, whether a focal distance threshold—corresponding to whether an entirety of the body part is visible—is satisfied, whether upper and lower teeth contact, whether a lighting threshold is satisfied, whether a localized calculus (e.g., plaque buildup) is present, and whether a gingiva recession is present.

In some embodiments, the term "categorical classification" may refer to characteristics that may be classified into one or more categories. In some implementations, the characteristics may be classified into one or more sets of mutually exclusive categories. With respect to the image data stream, examples of categorical classifications may include, without limitation, an anterior view, a left buccal view, and a right buccal view.

In some embodiments, certain characteristics may be either binary or categorical classifications. For example, a head pose of the patient (e.g., an angle of the patient's head as viewed in the image data stream) may be a binary classification (e.g., upright or tilted) or a categorical classification (e.g., classified into various pose categories based on slight tilt, large tilt, angle toward or away, etc.). In another example, a blurriness of the image data stream may be either a binary classification (e.g., too blurry or not too blurry) or a categorical classification (e.g., a degree of blurriness, an area within the image data stream being blurry).

The systems described herein may perform step 304 in a variety of ways. In one example, AI module 206 may analyze image data stream 222 and save the analysis results as binary classifications 224 and categorical classifications 226. In FIG. 4, at 406, image data stream 222 may be classified by the neural network classifier (e.g., AI module 206).

Figure 5:
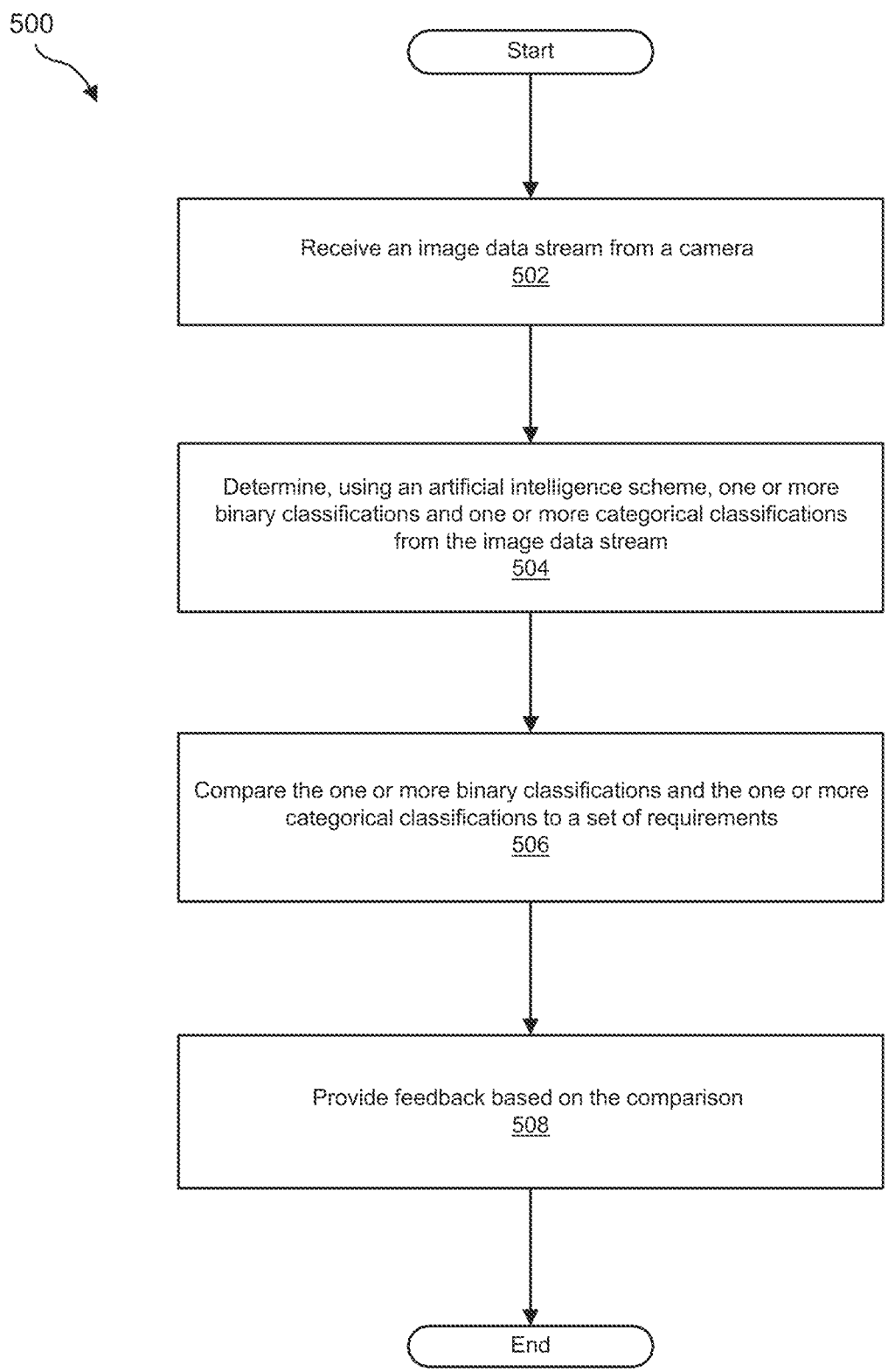
FIG. 5 shows an example neural network for photo guidance, in accordance with some embodiments.

FIG. 5 illustrates an environment 500 for classification. Images 522, which may correspond to image data stream 222, may be an input to neural network 506, which may correspond to AI module 206. Neural network 506 may include one or more AI schemes, such as a convolutional neural network, deep learning, etc. Neural network 506 may undergo training via training data in order to recognize the various classifications described above. Neural network 506 may determine categorical classifications 526, which may correspond to categorical classifications 226.

In addition, neural network 506 may include a binary classifier. The binary classifier may determine the binary classifications using binary cross-entropy, which may utilize a loss function to predict a probability of between two possible values for each binary classification. Neural network 506 may determine binary classifications 524, which may correspond to binary classifications 224.

Turning back to FIG. 3, at step 306 one or more of the systems described herein may compare the one or more binary classifications and the one or more categorical classifications to a set of requirements. For example, guidance module 208 may compare binary classifications 224 and categorical classifications 226 to requirements 234. The requirements may indicate what clinically relevant information may be required, particular with respect to photos.

The systems described herein may perform step 306 in a variety of ways. In one example, requirements module 210 may determine requirements 234 that may be customized for a particular patient at a particular state of treatment. For example, requirements module 210 may analyze patient data 136 and/or treatment data 138 to determine requirements 234. Patient data 136 may indicate patient-specific circumstances which may affect requirements 234. For example, patient data 136 may indicate that the patient is missing certain teeth such that requirements 234 may not require visibility of teeth that are known to be missing and therefore not visible.

In some examples, requirements module 210 may reside in server 106 such that requirements 234 may be sent to computing device 102. In other examples, server 106 may send patient data 136 and/or treatment data 138 to computing device 102 such that computing device 102 may locally determine requirements 234. FIG. 4 illustrates at 410 that requirements and expectations (e.g., requirements 234) may be an input for guidance generation and capture initiation at 408.

Requirements 234 may include, for instance, visibility of a particular body part (e.g., posterior teeth, etc.), visibility of a particular appliance (e.g., cheek retractor), type of view captured, head pose (e.g., satisfactory head pose with respect to camera), etc. The particular body part may correspond to a tooth of interest identified from the current state of treatment plan. For example, patient data 136 and/or treatment data 138 may indicate significant movement for a certain tooth. The particular body part may further correspond to one or more teeth near the tooth of interest. For example, if significant movement is expected for a certain tooth, the neighboring teeth may be of interest.

In some examples, the diagnosis may require the patient to wear an appliance. For example, the patient may be required to wear a cheek retractor to properly expose the patient's teeth for viewing. In another example, the patient may be required to wear an orthodontic aligner so that the practitioner may inspect the aligner's interaction with the patient's teeth.

Guidance module 208 may determine from binary classifications 224 and categorical classifications 226 whether requirements 234 are met. For example, guidance module 208 may determine from categorical classifications 226 whether binary the required views of the patient's teeth are captured. Guidance module 208 may determine from binary classifications 224 may indicate whether the required teeth are in the required views.

Returning to FIG. 3, at step 308 one or more of the systems described herein may provide feedback based on the comparison. For example, guidance module 208 may provide guidance prompts 228.

In some embodiments, the term "guidance prompts" may refer to audio, visual, and/or haptic prompts that may provide instruction to a user. Examples of guidance prompts may include, without limitation, overlays on a device screen, text notifications, oral instructions, a tone or other sound, a vibration, etc.

The systems described herein may perform step 308 in a variety of ways. In one example, guidance module 208 may determine guidance prompts 228 based on the comparison. Guidance prompts 228 may include instructions for the user to manipulate system 200 into a configuration that may take images satisfying requirements 234. For example, the instructions may include an instruction to adjust a camera view of the camera to include a particular body part in the camera view, such as moving the camera closer or farther, pan/tilt/zoom the camera, change an angle, tracking or otherwise moving the camera, etc. The instructions may include an instruction to insert or remove a particular appliance. The instructions may also include an instruction to move a particular body part, such as open or close the patient's bite, open the patient's jaw wider, etc. The instruction may include an instruction to adjust one or more camera settings, such as zoom, focus, turn on/off a flash, etc.

Guidance prompts 228 may indicate if requirements 234 are met. For example, guidance prompts 228 may instruct the patient to take the photo to save as image data 232.

In FIG. 4, at 428 the guidance may be displayed (e.g., guidance prompts 228) or the image may be captured. Guidance prompts 228 may include visual prompts that may be displayed visually, such as an overlay showing guide lines, arrows, graphical instructions, as text in an overlay or window, light patterns, grayed out images, ghost images, etc. Guidance prompts 228 may include audible prompts that may be presented as audio, such as oral instructions, chimes, warning tones, increasing/decreasing beeps (e.g., as the view gets closer/further from satisfying requirements 234), etc. Guidance prompts 228 may include haptic prompts that may be presented as vibrations (e.g., of decreasing strength as requirements 234 are closer to satisfaction, a vibration when requirements 234 are satisfied), warning vibrations, or other haptic responses.

The feedback may include instructions to system 200 for performing automatic actions when requirements 234 are not satisfied. Guidance prompts 228 may instruct camera module 204 to automatically adjust one or more camera settings. For example, rather than instruction the patient to adjust the camera settings, camera module 204 may automatically make the adjustments. In another example, guidance prompts 228 may instruct camera module 204 to automatically capture image data 232 if requirements 234 are satisfied. Alternatively, automatically capturing image data 232 may include saving portions of image data stream 222 that satisfies requirements 234. In some examples, guidance prompts 228 may include a confirmation such that the patient may confirm or cancel the automatic actions.

In some examples, guidance prompts 228 may prevent certain actions, such as preventing capture of image data 232 of the body part when at least one of requirements 234 is not satisfied. In some examples, requirements 234 may include hardware requirements (e.g., camera resolution, zoom, etc.)

such that guidance prompts 228 may prevent capture of image data 232 if the hardware requirements are not satisfied. In some examples, guidance prompts 228 may include sending a notification. System 200 may send a notification to server 106 or other computing device to inform the practitioner of certain results. For instance, the notification may indicate if an attachment has fallen off of a tooth, that a plaque buildup is detected, or other abnormal condition that may be highlighted for the practitioner.

Although method 300 is presented as a sequence of steps, in some examples, the steps of method 300 may be repeated as needed to provide continuous feedback until the desired images are captured. Thus, certain steps may be repeated, and requirements 234 and/or guidance prompts 228 may be continuously updated until image data 232 is sufficiently captured.

As described above, a patient may have a device, such as a smartphone, that is capable of taking photos. The smartphone may be provided a previously-trained neural network that may assist the patient in taking clinically relevant photos. The patient may be provided guidance to ensure the photos satisfy clinical requirements. The requirements may be customized to the patient at that particular stage of the patient's treatment. Thus, the patient's doctor may be able to remotely view the patient to track the patient's progress, update the treatment, or diagnose any issues.

Although the examples herein are described with respect to orthodontic care, in other implementations the remote care may include any other medical care that may be conducted via external photography.

Image Based Assessment

Image-based systems and methods as described herein may allow for remote assessment and follow-up with a patient during orthodontic treatment. The systems and methods allow a doctor to quickly and accurately assess a patient's progress or lack thereof based on photos or images the patient has taken. The photos or images to be taken outside the doctor's office or other clinical offices and instead may be taken by, for example, a handheld device such as a smart phone or digital camera. The assessment may include tracking the actual movement and position of a patient's teeth during orthodontic treatment as compared to the expected movement and position of the patient's teeth during orthodontic treatment.

In some embodiments, the patient captures two-dimensional photographic images of their teeth, which are then compared with three-dimensional models of the expected position of the patient's teeth during a given stage of treatment. The comparison may include determining the positional deviation or error between the actual position of the patient's teeth and the expected position of the patient's teeth based on a three-dimensional model of the patient's teeth for the particular stage of treatment. Other methods of assessing a patient's progress may include monitoring the fit of an orthodontic aligner on the patient's teeth. However, the fit of an orthodontic aligner or a gap between the orthodontic aligner and the patient's teeth is not necessarily reflective of an off-track deviation of the patient's teeth.

Figure 6:
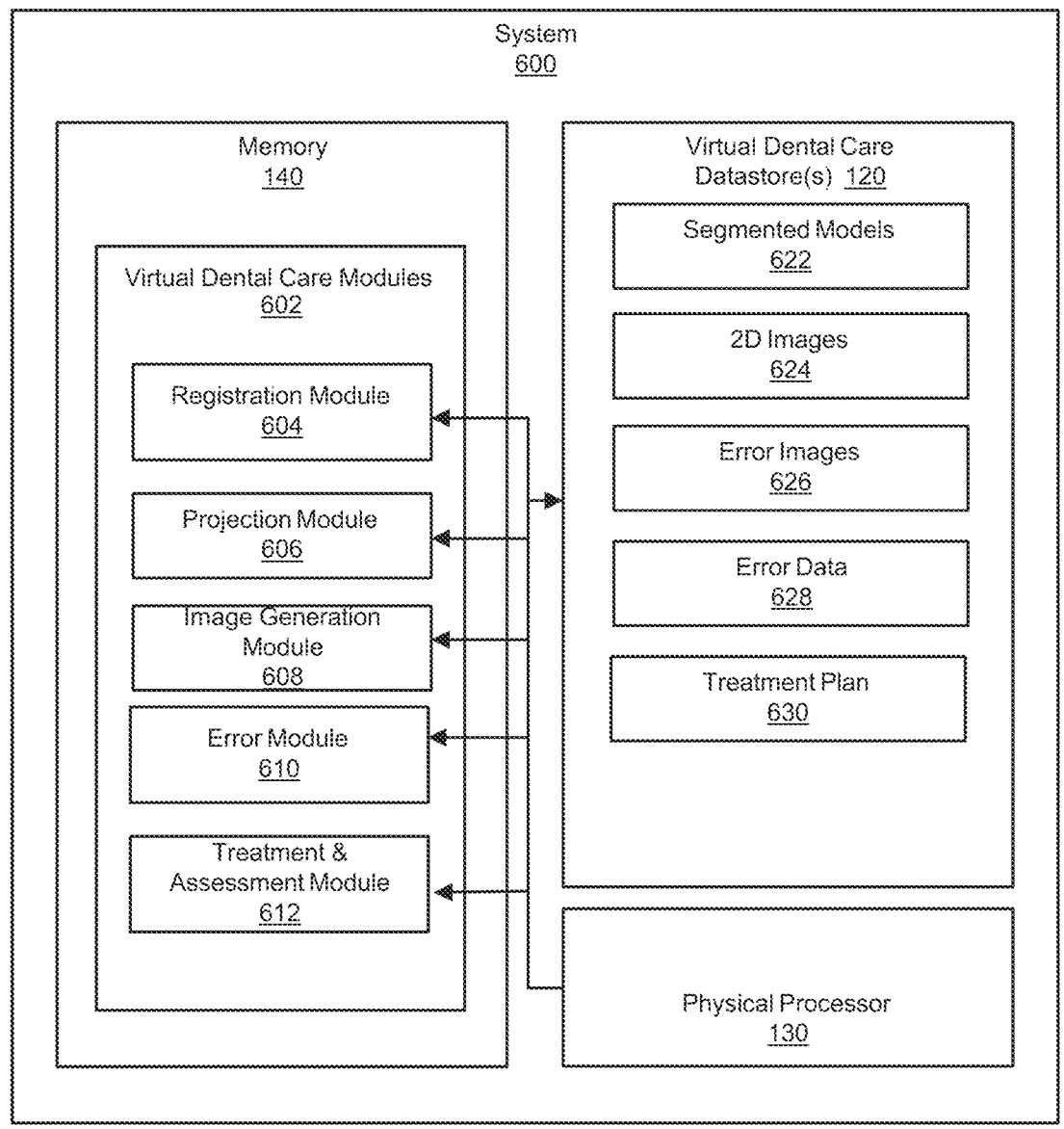
FIG. 6 shows a block diagram of an example system for differential error generation, according to embodiments herein.

FIG. 6 is a block diagram of an example system 600 for determining an error between an expected tooth position and an actual tooth position. As illustrated in this figure, example system 600 may include one or more virtual dental care modules 602 for performing one or more tasks. As will be explained in greater detail below, virtual dental care modules 602 may include a registration module 604, a projection module 606, an image generation module 608, an error module 610, and a treatment and assessment module 612. Although illustrated as separate elements, one or more of virtual dental care modules 602 in FIG. 6 may represent portions of a single module or application.

In certain embodiments, one or more of virtual dental care modules 602 in FIG. 6 may represent one or more software applications or programs that, when executed by a computing device, may cause the computing device to perform one or more tasks. For example, and as will be described in greater detail below, one or more of virtual dental care modules 602 may represent modules stored and configured to run on one or more computing devices, such as the devices illustrated in FIG. 1A (e.g., computing device 102 and/or server 106). One or more of modules 602 in FIG. 6 may also represent all or portions of one or more special-purpose computers configured to perform one or more tasks.

As illustrated in FIG. 6, example system 600 may also include one or more virtual dental care datastore(s) 120, such as segmented teeth models 622, two-dimensional images 624, error images 626, error data 628, and treatment plan data 630. Virtual dental care datastore(s) 120 may include one or more datastores configured to store any type or form of data or information.

The virtual dental care datastore(s) 120 may include segmented teeth models 622 which may include data representing three-dimensional models of each individual tooth of the patient. The three-dimensional models may be generated based on an initial three-dimensional (or 3D) intraoral scan of the patient's teeth. During an intraoral scan, a handheld scanning device generates a three-dimensional model of the patient's upper and lower arches. After capturing three-dimensional models of the upper and lower arches, each tooth within the three-dimensional model is separated from the model to form an individual tooth model. These individual tooth models are then used during the treatment planning process in order to generate each of the of treatment stages to move the teeth from an initial position towards a target final position and then to generate orthodontic aligners that are worn on the patient's teeth in order to move the teeth from the initial position towards the final position.

The virtual dental care datastore(s) 120 may include two-dimensional (or 2D) images 624 which may include data representing two-dimensional images of the patient's mouth and teeth. In some embodiments, the two-dimensional images 624 are captured using the systems and methods described herein, for example by using the AI based photo capture system discussed above. The two-dimensional images 624 may include one or more of three buccal and two occlusal photos of the patient's teeth. For example, the three buccal photos may include an anterior image of the patient's teeth in occlusion, a left buccal image of the patient's teeth in occlusion, and a right buccal image of the patient's teeth in occlusion. In some embodiments, the buccal photos may also include images of the teeth in a neutral bite or non-occluded position. The two-dimensional images 624 may also include occlusal photos of the patient's teeth. For example, the two-dimensional images 624 may include an image of the occlusal surfaces of teeth of the patient's upper arch and an image of the occlusal surfaces of teeth of the patient's lower arch.

The virtual dental care datastore(s) 120 may include treatment plan data 630. The treatment plan data 630 may include the positions and orientations of each of the patient's teeth for each stage of a treatment plan. In some embodiments, the positions and orientations of the teeth may be stored as three-dimensional positional locations and angular orientations of each tooth and the patient's upper and lower arches. In some embodiments the positions and orientations of the patient's teeth may be stored as a collection of three-dimensional segmented models of the patient's upper and lower arches for each stage of treatment. In some embodiments, the three-dimensional positional locations may be partial. For example, rather than exhibiting tooth-to-gum lines, the 3D positional locations may be tooth-to-tooth or tooth-to-space. In some embodiments, the treatment plan data may include other information such as the location of attachments on the patient's teeth, and other orthodontic devices such as wire and bracket braces, elastics, temporary anchorage devices, and other orthodontic devices.

Figure 9:
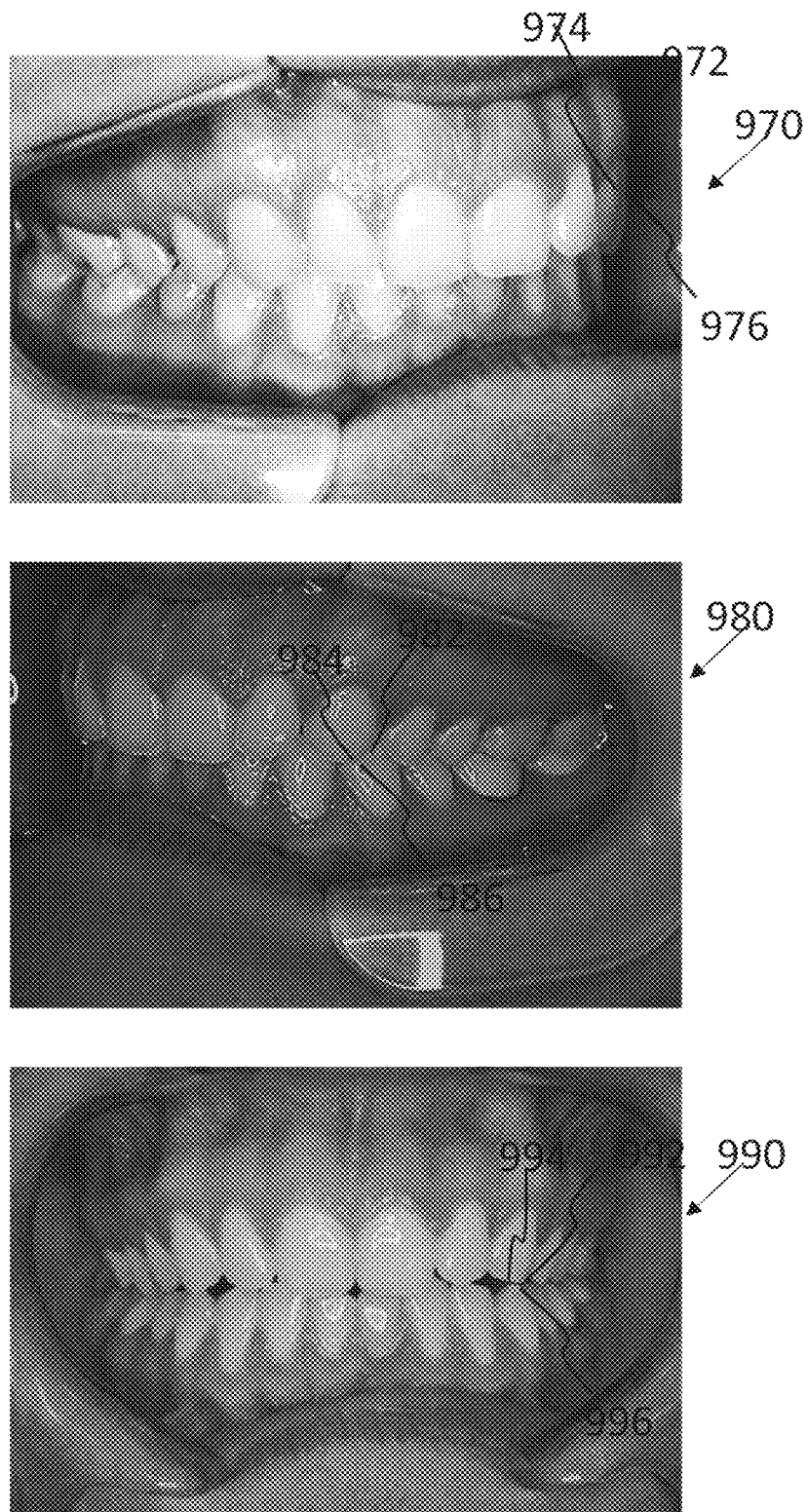
FIG. 9 an outlined differential error image of teeth of a patient for a stage of treatment, according to embodiments herein.
Figure 10:
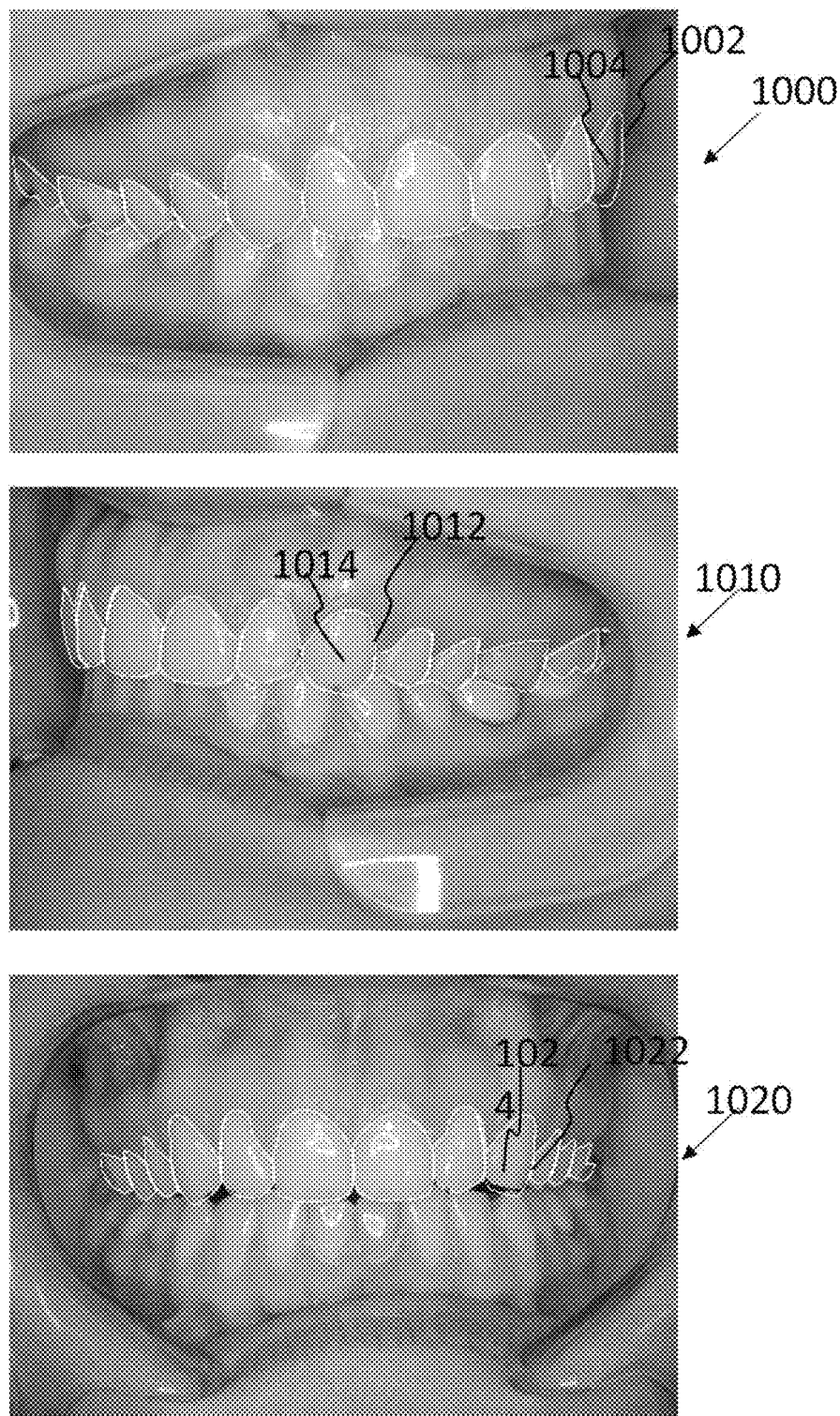
FIG. 10 an outlined differential error image of teeth of a patient for a stage of treatment, according to embodiments herein.

The virtual dental care datastore(s) 120 may include error images 626. The systems and methods disclosed herein may generate error images 626 based on a difference in tooth position between a two dimensional image of the patient's teeth and a three dimensional dentition model that is generated based on the expected tooth position for a current stage of the patient's treatment plan. As discussed below with respect to capital FIG. 7, the error images 626 may be generated through a process of registering the 3D model of the patient's expected tooth positions to a current stage two-dimensional photograph or photographs of the patient's dentition. After registration, the dentition is projected into the same image plane as the two-dimensional image and then the difference between the position and orientation of the teeth and the two-dimensional image and the three-dimensional projection are used to form of an error image, for example as shown in FIG. 8. In FIG. 9, a plurality of error images are shown wherein the error between the tooth position in the three dimensional dentition model and the tooth position in the two-dimensional images are shown via an overlay over the two-dimensional image. In FIG. 10 a plurality of error images are shown wherein the error between the tooth position in the three-dimensional dentition model and the tooth position in the two-dimensional images are shown via an outline of the tooth position of the digital model overlaid onto the two-dimensional images. In FIG. 11 error images may include 3D generated models of the treatment plans current stage next to the 2D image of the patient's teeth. In some embodiments, the error between the 3D model and 2D image may be indicated by a color or other visual indicator to show how much on or off track the tooth positions are.

The virtual dental care datastore(s) 120 may include error data 628. The systems and methods disclosed herein may generate error data in many ways. For example, the error data may be generated based on the differences between the position and orientation of the teeth and the two-dimensional image and the three-dimensional projection. The error data 628 may include differential position and rotational angles in three-dimensional space for each of the teeth in the patient's dentition. FIG. 12 shows an example of a chart generated using error data 628 including differential position between the expected position of each of the patient's tooth at each stage of treatment and the actual position of each of the patient's teeth. In some embodiments, the error may be calculated as a numerical value, such as a distance in millimeters, indicating a degree to which the tooth positions are off track.

The virtual dental care modules 602 may include a registration module 604. The registration module 604 registers the patient's three-dimensional dentition including three-dimensional segmented models of the teeth and arrangements as found in the current stage of the treatment plan with two-dimensional images of the patient's teeth taken during the current stage of the treatment plan. The three-dimensional segmented models and the two-dimensional images may be registered in many ways. For example, edge detection techniques may be used to determine the edges and shapes of the teeth in the two-dimensional images in order to determine which teeth are visible in the two-dimensional image and where they are located within the two-dimensional image and which teeth in the two-dimensional image correspond to particular teeth and the three dimensional image.

The virtual dental care modules 602 may include a projection module 606. The projection module 606 projects the three-dimensional dentition for the current stage of treatment onto the two-dimensional image of the patient. The projection may be made based on knowledge of the properties of the camera when the image was taken. The properties may include camera focal length and aperture, camera focusing distance, camera angle and orientation, and the distance between the camera and the patient's dentition, among other properties. Using the property information, the three-dimensional dentition is projected as a two-dimensional image in the same coordinate space as the teeth within the two-dimensional image.

The virtual dental care modules 602 may include an image generation module 608. The image generation module 608 generate error images such as the error images depicted in FIGS. 8, 9, 10, and 11. The projection from the projection module may be used to generate the error images in the image generation module 608. For example, in FIG. 8 a two-dimensional error image is generated based on the difference between the positions of the teeth in the two-dimensional image and the positions of the teeth in the three-dimensional projection. The outline shown in FIG. 8 represents the error between the location of the teeth and the 3D projection and the 2D image. In FIG. 9, a plurality of error images are shown wherein the error between the tooth position in the three dimensional dentition model and the tooth position in the two-dimensional images are shown via an overlay over the two-dimensional image. In FIG. 10, a plurality of error images are shown wherein the error between the tooth position in the three-dimensional dentition model and the tooth position in the two-dimensional images are shown via an outline of the tooth position in the digital model overlaid onto the two-dimensional images. In FIG. 11, error images may include three-dimensional generated models of the teeth in a current stage of the treatment plan next to the two-dimensional image of the patient's teeth. In FIG. 12, three-dimensional error images are shown including a first image depicting a three-dimensional view of the patient's expected tooth position based on a treatment plan side-by-side with the actual position of the patient's teeth based on the two-dimensional images.

The virtual dental care modules 602 may include an error generation module 610. The error generation module 610 quantifies the error between the positions of the teeth in the two-dimensional images and the three-dimensional projections. The error may be determined in many ways, for example, the error image in FIG. 8 may be analyzed to find the pixel difference for each tooth of the patient's dentition. The pixel difference may be the difference between, for example, a location of an edge of a tooth in the two-dimensional image and the position of a corresponding edge of the corresponding tooth in the two-dimensional projection of the three-dimensional model. The number of pixels between the corresponding edges may be determined and then based on the dimensions of the pixels within the image, the real-world distance between the corresponding edges may be determined. For example, if each pixel within an image corresponds to 100 µm and there are 10 pixels between the corresponding edges of the corresponding teeth, then the error between the expected location of the tooth at the current stage and the actual location of the tooth at the current stage from that particular projection's point of view is 1000 µm. Such analysis may be carried out from multiple projection's points of view, for example in FIGS. 8, 9, and 10, left buccal, right buccal, and anterior projections of points of view are shown. In some embodiments, the maximum error for each tooth is determined from the error in of each projection and this error may be used to generate charts for each stage for example such as shown in FIG. 12.

The virtual dental care modules 602 may include a treatment and assessment module 612. The treatment and assessment module 612 may perform an assessment of the patient's teeth or facilitate the performance of an assessment of the patient's teeth and help determine guidance and potential intervention and treatment for the patient based on the progress of the patient's treatment determined from the errors between the actual positions of the patient's teeth and the expected positions of the patient's teeth, as discussed herein. The assessment and treatment may take many forms, for example the assessment may determine whether and how far off track the patient's treatment is, as compared to the expected positions of the patient's teeth for each stage of treatment. Based on this information additional, intervention or treatment may be suggested to the patient or doctor, as discussed herein.

Figure 7:
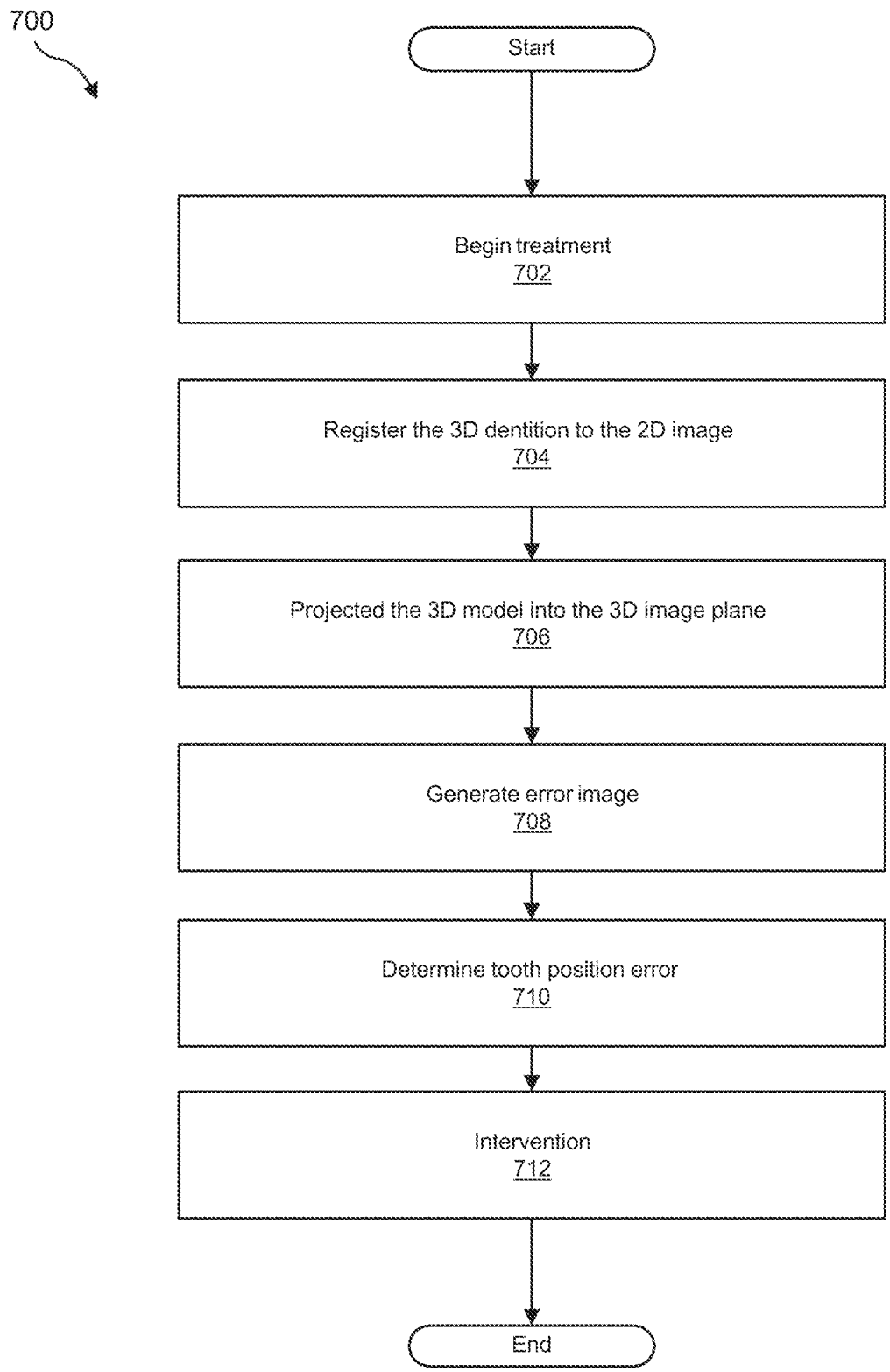
FIG. 7 shows a method of assessing the movement of teeth of a patient, according to embodiments herein, according to embodiments herein.

FIG. 7 shows a method 700 of assessing the movement of teeth of a patient. The method 700 may begin at step 702 with the initiation of orthodontic treatment of the patient's teeth. Initiation of orthodontic treatment to the patient's teeth may include many processes. In some embodiments, the patient's dentition is scanned with the three-dimensional intraoral scanner in order to generate a three-dimensional model of the patient's dentition. The three-dimensional model of the patient's dentition may include individually segmented teeth representing each of the patient's teeth of their upper and lower arches. An assessment may be made as to desired final positions of the patient's teeth based on the initial position of the patient's teeth obtained from the intraoral scan. A series of intermediate tooth positions of the patient's teeth may be generated to incrementally move the teeth through a series of stages from the initial positions towards the final positions. Dental appliances may be fabricated based on the intermediate positions of the patient's teeth in order to move the teeth from the initial positions towards the final positions. A patient then wears each of the dental appliance for a period of time, for example 10 days to two weeks, during which time the dental appliance applies forces to the patient's teeth to move the teeth from a first position at the beginning of the treatment stage towards a second position at the end of the treatment stage. Each appliance is worn in succession in order to move the patient's teeth.

However, treatment may not progress as expected. Sometimes a patient's compliance may not be as expected. A patient may not wear the dental appliances throughout the day, for example they may take them off before eating and forget to put them on after completing their meal. Such lack of compliance may lead to teeth positions lagging their expected positions. Sometimes teeth provide more or less resistance to movement than expected. This may result in teeth moving slower or faster than expected. Differences in compliance and tooth resistance may result in a treatment going off-track, such that the actual position of the patient's tooth during a given stage of treatment may deviate from the expected position to a degree that an appliance may not fit the patient's teeth or may otherwise not provide the desired movement for stage.

Doctors may monitor the progress of the patient's treatment in order to anticipate or determined that a patient's treatment has gone off-track or may be progressing towards off-track so that they can provide intervention in order to bring the treatment back on track or to generate a new treatment plan to treat the patient's teeth.

At some point during treatment the doctor may decide to assess a patient's progress, for example at each stage of the patient's treatment their doctor may request the patient to take one or more photos of the patient's teeth, guided by the artificial intelligence systems and methods discussed herein.

At step 704 the process may register the three-dimensional model of the patient's dentition at the current stage of treatment with the two-dimensional image or images of the patient's teeth. The registration and other processes that occur during step 704 may be carried out by one or more modules of the system described herein, for example by the registration module 604. The registration module 604 may register the patient's three-dimensional dentition, including the three-dimensional segmented models, to the two-dimensional images in many ways. For example, edge detection techniques may be used to determine the edges and shapes of the teeth in the two-dimensional images in order to determine which teeth are visible in the two-dimensional image and where they are located within the two-dimensional image and which teeth in the two-dimensional image correspond to particular teeth and the three dimensional image.

At step 706 the three-dimensional image of the patient's teeth are projected into the two-dimensional image plane of one or more of the two-dimensional images. The projection module 606 may carry out the processes of step 706 by projecting the three-dimensional dentition for the current stage of treatment onto the two-dimensional image of the patient. The projection may be made based on knowledge of the properties of the camera when the image was taken. The properties may include camera focal length and aperture, camera focusing distance, camera angle and orientation, and the distance between the camera and the patient's dentition, among other properties. Using the property information, the three-dimensional dentition is projected as a two-dimensional image in the same coordinate space as the teeth within the two-dimensional image.

At step 708 in error image is generated. The image generation module 608 may generate the error images at step 708. Examples of error images are depicted in FIGS. 8, 9, 10, and 11. At step 708 the projection generated at step 706 by the projection module 606 may be used to generate the error images. For example, in generating the error image depicted in FIG. 8, a two dimensional error image is generated based on the difference between the positions of the teeth in the two-dimensional image and the positions of the teeth in the three-dimensional projection. The outline shown in FIG. 8 represents the error between the location of the teeth and the 3D projection and the 2D image. In generating the error images depicted in FIG. 9, the error image depicted in FIG. 8 may be used to create an overlay over the two-dimensional image. The overlay may be a mask, wherein the color properties of the image are adjusted in order to highlight the positional errors of the teeth for example the mask may adjust the brightness luminance or color values of the two-dimensional image based on the error mask.

In generating the error images depicted in FIG. 10, an overlay including an outline of the teeth of the projected three-dimensional model of the current stage of treatment is overlaid onto the two-dimensional image of the patient's teeth. The outline may be opaque or translucent and may take on one or more colors for example the outline may be a white outline the black outline or another color.

In some embodiments, the overlay shown in FIG. 9 and the overlay in FIG. 10 may vary based on one or more factors. For example, the color, brightness, thickness, and other properties of the overlay may vary based on the degree of error between the expected position of the tooth and the actual position of the tooth. In some embodiments, the overlay may be a two-dimensional rendering of the three-dimensional model of the patient's teeth the patient's teeth which may be rendered on top of the two-dimensional image. The two-dimensional rendering of the three-dimensional model may be shown as partially translucent, in false color, or may include other indications to show the difference between the expected position of the patient's teeth and the actual position of the patient's teeth. In some embodiments, the overlay may be blinked on and off in order to help an observer observe the differing positions of the patient's teeth.

In generating the error images depicted in FIG. 11, a three-dimensional model of the treatment plan's current stage and a two-dimensional image of the patient's teeth may be generated. The three-dimensional model and the two-dimensional image are generated side-by-side to allow for simultaneous viewing of each image. In some embodiments, a three-dimensional model of the patient's teeth may be generated based on the positions of the teeth in the two-dimensional images of the patient. The two-dimensional images may be used as textures to provide appropriate color and shading to the three-dimensional model. This three-dimensional model of the patient's teeth may be displayed side-by-side or simultaneously with the three-dimensional model of the patient's teeth in their expected position.

In generating the error images depicted in FIG. 12, a first image depicting a three-dimensional view of the patient's expected tooth position based on a treatment plan is displayed side-by-side with the actual position of the patient's teeth based on the two-dimensional images.

In some embodiments, error images may be generated for a plurality of stages of the patient's treatment. For example, error images may be generated at each stage of the patient's treatment in order to allow a doctor to assess a patient's progress over time. In some embodiments, the error images may be presented with a user interface that includes user adjustable navigation tools such as a time selector or slider whereby the doctor may quickly move between error images of various stages of treatment. In some embodiments, the user interface may include navigation and zoom tools that allow a doctor other user to zoom in and out on the patient's error images to more closely observe the error and may allow the doctor to pan and rotate the error images in order to further facilitate assessment of the patient's dentition. In some embodiments, the various views of the error images may be synchronized with each other such that a zoom, pan, or rotation of one model or image causes a corresponding zoom, pan, or rotation of another model or image.

At step 710 the positional error of each tooth may be determined. The process of step 710 may be performed by the error generation module 610. At step 710, the error between the positions of the teeth in the two-dimensional images and the three-dimensional projections is quantified. The error may be quantified in many ways, for example, the error image in FIG. 8 may be analyzed to find the pixel difference for each tooth of the patient's dentition. The pixel difference may be the difference between, for example a location of an edge of tooth in the two-dimensional image and the position of a corresponding edge of the corresponding tooth in the two-dimensional projection. The number of pixels between the corresponding edges may be determined and then based on the dimensions of the pixels within the image the real-world distance between the corresponding edges may be determined. For example, if each pixel within an image corresponds to 100 μm and there are 10 pixels between the corresponding edges of the corresponding teeth, then the error between the expected location of the tooth at the current stage and the actual location of the tooth at the current stage from that particular projection's point of view is 1000 μm. Such analysis may be carried out from multiple projection's points of view, for example in FIGS. 8, 9, and 10, left buccal, right buccal, and anterior projections of points of view are shown. In some embodiments, the maximum error for each tooth is determined from the error in of each projection. This error may be used to generate charts for each stage, for example, such as shown in FIG. 12. In some embodiments, charts, such as those shown in FIG. 12, may be generated in a subsequent error image generation step 708

At step 712 intervention in the patient's treatment and/or revisions to the treatment plan may be generated as discussed herein, for example with respect to FIGS. 13-18.

FIG. 8 shows differential error images of teeth of a patient for a stage of treatment. The top image is a right buccal view error image 870, the middle image is a left buccal view error image 880, and the bottom image is an anterior view error image 890. The error images 870, 880, 890 are two-dimensional error images generated based on the difference between the positions of the teeth in the two-dimensional image and the positions of the teeth in the three-dimensional projection. The error image 870, represents the error between the location of the teeth and the three-dimensional projection and the three-dimensional image, as viewed from a right buccal position. The error image shows differences in the actual position of the patient's teeth and the expected position of the patient's teeth. In the right buccal view, the right molars 841, the right bicuspids 843, the right canine 845, the incisors 847, and the left canine 842 are visible. With reference to the left canine 842, the first edge 844 of the error image 840 corresponds to the edge of the left canine 842 in the two-dimensional image. The second edge 846 corresponds to the same edge of the left canine 842 of the three-dimensional model of the patient's teeth projected in the same plane as the two-dimensional image of the patient's teeth such that the edge aligns with edge of the tooth and the three-dimensional model from the perspective of the camera that took the two-dimensional image of the patient's dentition from the right buccal side of the patient. The difference between the location of the first edge 844 and the second edge 846 quantifies the displacement of the tooth 842 in the plane of the two-dimensional image 840.

The error image 850, represents the error between the location of the teeth and the three-dimensional projection and the three-dimensional image as viewed from a left buccal position. The error image shows differences in the actual position of the patient's teeth and the expected position of the patient's teeth. In the left buccal view, the left molars 851, the left bicuspids 853, the left canine 842, the incisors 847, and the right canine 845 are visible. With reference to the left canine 842, the first edge 854 of the error image 850 corresponds to the edge of the left canine 842 in the two-dimensional image taken from the left buccal perspective. The second edge 856 corresponds to the same edge of the left canine 842 of the three-dimensional model of the patient's teeth projected in the same plane as the two-dimensional image of the patient's teeth such that the edge aligns with edge of the tooth and the three-dimensional model from the perspective of the camera that took the two-dimensional image of the patient's dentition from the left buccal side of the patient. The difference between the location of the first edge 854 and the second edge 856 quantifies the displacement of the tooth 842 in the plane of the two-dimensional image 850.

The error image 860, represents the error between the location of the teeth and the three-dimensional projection and the three-dimensional image as viewed from a anterior position. The error image shows differences in the actual position of the patient's teeth and the expected position of the patient's teeth. In the anterior view, the left canine 842, the incisors 847, and the right canine 845 are visible. With reference to the left canine 842, the first edge 864 of the error image 860 corresponds to the edge of the left canine 842 in the two-dimensional image taken from the anterior perspective. The second edge 866 corresponds to the same edge of the left canine 842 of the three-dimensional model of the patient's teeth projected in the same plane as the two-dimensional image of the patient's teeth such that the edge aligns with edge of the tooth and the three-dimensional model from the perspective of the camera that took the two-dimensional image of the patient's dentition from the left buccal side of the patient. The difference between the location of the first edge 864 and the second edge 866 quantifies the displacement of the tooth 842 in the plane of the two-dimensional image 860.

In some embodiments, the differences between the locations of the edges of the teeth in the three different image planes of the error images 840, 850, 860 may be used to directly determine the displacement of the teeth with respect to the expected location of the teeth. In some embodiments the locations of the teeth in the error images 840, 850, 860 may be used to determine the location of the teeth and three-dimensional space based on known angles and orientations of the camera and the image plane in which the two-dimensional images were taken. As discussed below, the error image may be used to highlight or otherwise indicate the difference between the expected position of the patient's teeth and the actual position of the patient's teeth.

For example, in FIG. 9 the error images are used to create a mask of the two-dimensional images of the patient's teeth. In generating the error images depicted in FIG. 9, the error image depicted in FIG. 8 is used to create an mask that generates an overlay over the two-dimensional image. The color properties of the masked area of the two-dimensional image may be altered to highlight the difference in the locations of the teeth in the two-dimensional image, as compared to the three-dimensional projection. In some embodiments the color properties of the masked portion of the images are adjusted in order to highlight the positional deviation of the teeth, for example the mask may adjust the brightness, luminance, or color values of the two-dimensional image based on the error mask.

The error images 970, 980, 990 are two-dimensional error images generated based on the difference between the positions of the teeth in the two-dimensional image and the positions of the teeth in the three-dimensional projection. In the error image 970, the mask 978 represents the error between the location of the teeth and the three-dimensional projection and the three-dimensional image as viewed from a right buccal position. In the right buccal view, the right molars 841, the right bicuspids 843, the right canine 845, the incisors 847, and the left canine 842 are visible. With reference to the left canine 842, the first edge 974 of the mask 978 corresponds to the edge of the left canine 842 in the two-dimensional image. The second edge 976 corresponds to the same edge of the left canine 842 of the three-dimensional model of the patient's teeth projected in the same plane as the two-dimensional image of the patient's teeth such that the edge aligns with edge of the tooth and the three-dimensional model from the perspective of the camera that took the two-dimensional image of the patient's dentition from the right buccal side of the patient. Thus, the overlay created by the mask 978 highlights the positional difference between the location of the first edge 974 and the second edge 976 of the tooth 842 in the plane of the two-dimensional image 970.

In the error image 980, the mask 982 represents the error between the location of the teeth and the three-dimensional projection and the three-dimensional image as viewed from a left buccal position. In the left buccal view, the left molars 851, the left bicuspids 853, the left canine 842, the incisors 847, and the right canine 845 are visible. With reference to the left canine 842, the first edge 984 of the mask 982 corresponds to the edge of the left canine 842 in the two-dimensional image taken from the left buccal perspective. The second edge 986 corresponds to the same edge of the left canine 842 of the three-dimensional model of the patient's teeth projected in the same plane as the two-dimensional image of the patient's teeth such that the edge aligns with edge of the tooth and the three-dimensional model from the perspective of the camera that took the two-dimensional image of the patient's dentition from the left buccal side of the patient. Thus, the overlay created by the mask 982 highlights the positional difference between the location of the first edge 984 and the second edge 986 highlights the positional difference between the location of the first edge 984 and the second edge 986 of the tooth 842 in the plane of the two-dimensional image 980.

In the error image 990, the mask 992 represents the error between the location of the teeth and the three-dimensional projection and the three-dimensional image as viewed from a anterior position. In the anterior view, the left canine 842, the incisors 847, and the right canine 845 are visible. With reference to the left canine 842, the first edge 994 of the mask 996 corresponds to the edge of the left canine 842 in the two-dimensional image taken from the anterior perspective. The second edge 996 corresponds to the same edge of the left canine 842 of the three-dimensional model of the patient's teeth projected in the same plane as the two-dimensional image of the patient's teeth such that the edge aligns with edge of the tooth and the three-dimensional model from the perspective of the camera that took the two-dimensional image of the patient's dentition from the left buccal side of the patient. Thus, the overlay created by the mask 992 highlights the positional difference between the location of the first edge 994 and the second edge 996 highlights the positional difference between the location of the first edge 994 and the second edge 996 of the tooth 842 in the plane of the two-dimensional image 990.

In some embodiments, the differences between the locations of the edges of the teeth in the three different image planes of the error images 840, 850, 860 may be used to directly determine the displacement of the teeth with respect to the expected location of the teeth. In some embodiments the locations of the teeth in the error images 840, 850, 860 may be used to determine the location of the teeth and three-dimensional space based on known angles and orientations of the camera and the image plane in which the two-dimensional images were taken. As discussed below, the error image may be used to highlight or otherwise indicate the difference between the expected position of the patient's teeth and the actual position of the patient's teeth.

FIG. 10 depicts outlined error images 1000, 1010, 1020 of teeth of a patient for a stage of treatment. Error image 1000 depicts a two-dimensional image of the patient's dentition from a right buccal perspective. The patient's teeth 1004 in their current position are depicted in the two-dimensional image while the outline 1002 depicts the expected position of the patient's teeth according to the current stage of the treatment plan. The outline 1002 is generated based on a projection onto the two-dimensional image plane of a three-dimensional model of the patient's teeth at the expected position according to the current stage of the treatment plan. Each visible tooth of the dentition is represented in the outline 1002. The outline represents the edges of the teeth in the projected three-dimensional model. Each tooth outline may represent an outline of a silhouette of the patient's tooth from the two-dimensional image perspective. In some embodiments a tooth outline tooth outline may be defined by an occlusal or incisal edge, the interproximal edges of the teeth, and the gingival margin.

Error image 1010 depicts a two-dimensional image of the patient's dentition from a right buccal perspective. The patient's teeth 1014 in their current position are depicted in the two-dimensional image while the outline 1012 depicts the expected position of the patient's teeth according to the current stage of the treatment plan. The outline 1012 is generated based on a projection onto the two-dimensional image plane of a three-dimensional model of the patient's teeth at the expected position according to the current stage of the treatment plan. Each visible tooth of the dentition is represented in the outline 1012.

Error image 1020 depicts a two-dimensional image of the patient's dentition from a right buccal perspective. The patient's teeth 1024 in their current position are depicted in the two-dimensional image while the outline 1022 depicts the expected position of the patient's teeth according to the current stage of the treatment plan. The outline 1022 is generated based on a projection onto the two-dimensional image plane of a three-dimensional model of the patient's teeth at the expected position according to the current stage of the treatment plan. Each visible tooth of the dentition is represented in the outline 1022.

FIG. 11 shows a side-by-side of a three-dimensional rendered teeth image 1130 of the patient's teeth in their expected position that is based on the treatment plan and a two-dimensional image 1140 of the actual position of the patient's teeth. In generating the error images depicted in FIG. 11 the three-dimensional model 1130 of the treatment plan's current stage and the two-dimensional image 1140 of the patient's teeth may be generated. The three-dimensional model 1130 and the two-dimensional image 1140 may be generated side-by-side to allow for simultaneous viewing of each image. In some embodiments, image 1140 may represent a three-dimensional model of the patient's teeth in their actual current position generated based on the positions of the teeth in the two-dimensional images of the patient. The two-dimensional images may be used as textures to provide appropriate color and shading to the three-dimensional model. This three-dimensional model of the patient's teeth may be displayed side-by-side or simultaneously with the three-dimensional model of the patient's teeth in their expected position.

FIG. 12 shows charts 1250, 1260 of differential error, sometimes referred to as the degree of on-track or off-track of the teeth for teeth of a patient for each stage of treatment. Each column 1252 in the charts 1250, 1260 represents a tooth of an arch of a patient by its corresponding tooth number. Each row 1254 in the charts 1250, 1260 represents a stage of a treatment plan. The shading in each stage for each tooth depicts the degree of variation between the expected position of the patient's tooth and that stage and the actual position of the patient's tooth in that stage for example as determined above. The legend 1256 shows that the darker the shading the more off-track the patient's tooth. The chart 1250 shows the upper jaw tracking for the patient's teeth through stage 12 of a treatment plan. As shown by block 1257, block 1258, and block 1259 tooth 2, tooth 4, and tooth 7 are deviating from their expected position more than the other teeth. However, as shown by chart 1260, by stage 20 tooth 4 merely maintains its level off-trackness, while block 1268 and block 1269 show that tooth 2 and tooth 7 have continued to get further off-track over the course of treatment a doctor may use such a chart to determine whether and how to provide guidance to or treatment intervention for the patient.

Guidance Generation

Monitoring and assessing a patient's treatment progress in order to determine appropriate treatment guidance for the patient and then providing the treatment guidance to the patient may be a difficult, expensive, and time-consuming task. The use of stage by stage tracking or other periodic tracking and tooth deviations, as discussed above, allows a doctor to at least partially simplify the task of determining the type of guidance to give a patient and providing that guidance to the patient. For example, the patient may take pictures of their dentition using the artificial intelligence guidance, as discussed above and then the deviation of each of the patient's teeth from there expected position may be determined, as also discussed above. In addition, other image-based analysis may be conducted on the captured images in order to aid in assessment of the patient's treatment progress. Based on this information and doctor provided guidance information, the patient's teeth may be assessed and appropriate guidance for continuing or modifying the patient's treatment may be provided to the doctor or the patient.

Figure 13:
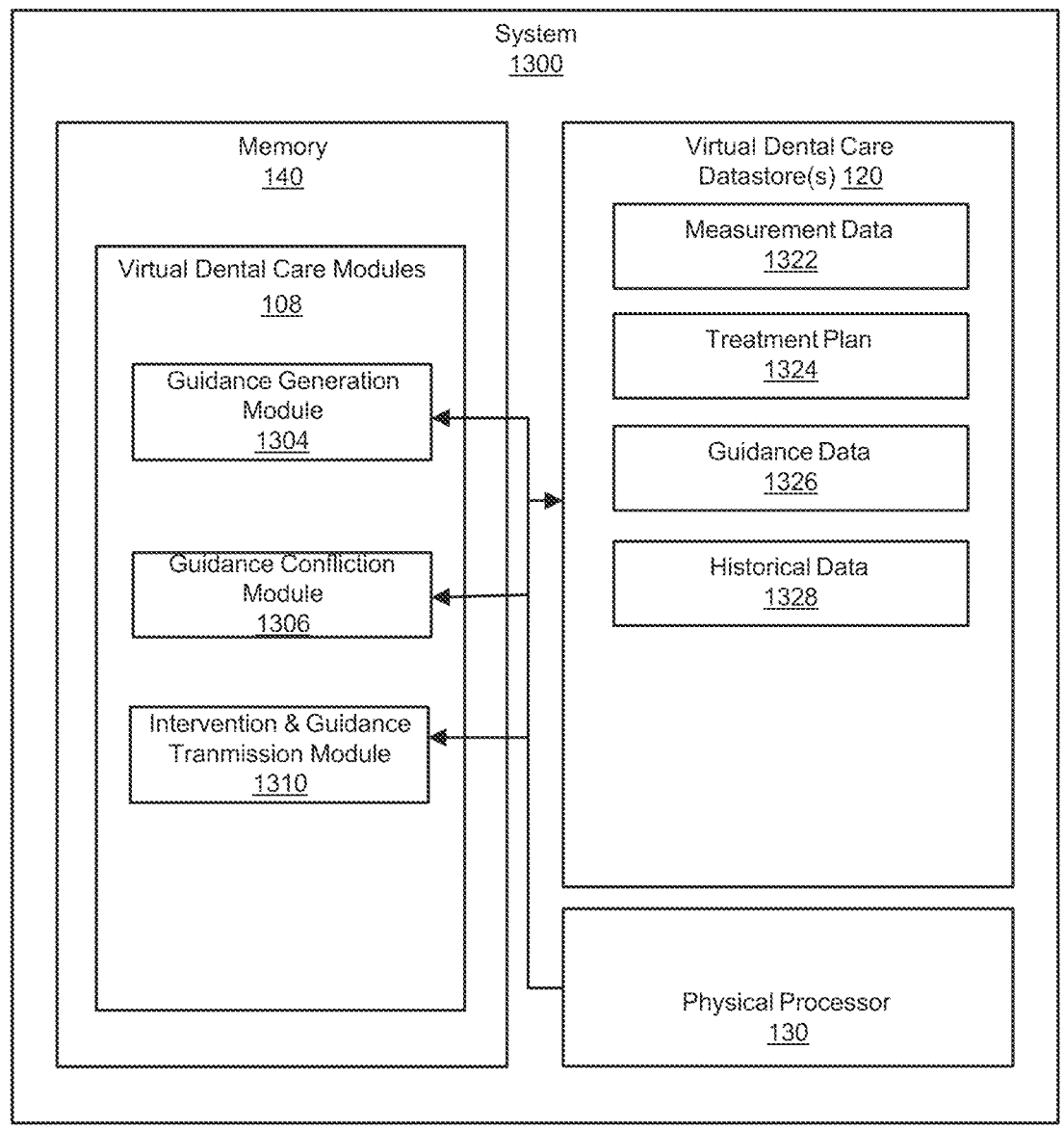
FIG. 13 shows a block diagram of an example system for providing guidance, according to embodiments herein.

FIG. 13 shows a block diagram of an example system 1300 for providing guidance. As illustrated in this figure, example system 1300 may include one or more virtual dental care modules 108 for performing one or more tasks. As will be explained in greater detail below, virtual dental care modules 108 may include a guidance generation module 1304, a guidance deconfliction module 1306, and a guidance and intervention transmission module 1308. Although illustrated as separate elements, one or more of virtual dental care modules 108 in FIG. 13 may represent portions of a single module or application.

In certain embodiments, one or more of virtual dental care modules 108 in FIG. 13 may represent one or more software applications or programs that, when executed by a computing device, may cause the computing device to perform one or more tasks. For example, and as will be described in greater detail below, one or more of virtual dental care modules 108 may represent modules stored and configured to run on one or more computing devices, such as the devices illustrated in FIG. 1A (e.g., computing device 102 and/or server 106). One or more of virtual dental care modules 108 in FIG. 13 may also represent all or portions of one or more special-purpose computers configured to perform one or more tasks.

As illustrated in FIG. 13, example system 1300 may also include one or more virtual dental care datastore(s) 120, such as measurement data 1322, treatment plan data 1324, guidance information 1326, and historical data 1323. Virtual dental care datastore(s) 120 may comprise any type or form of data or information.

The virtual dental care datastore(s) 120 may include measurement data 1322. Measurement data may include data, such as the error data discussed above with respect to FIG. 6. For example, the measurement data may include error data generated based on the differences between the position and orientation of the teeth and a two-dimensional image of a patient's teach and a give stage of treatment and a three-dimensional projection of the a three-dimensional model of the patient's teeth for the given stage of treatment. The measurement data 1322 may include differential position and rotational angles in three-dimensional space for each of the teeth in the patient's dentition. In some embodiments, the measurement data may also include the presence and absence of attachments and other orthodontic devices on the patient's dentition. In some embodiments, the measurement data 1322 may include information regarding the fit of the aligner on the patient's teeth. For example, the measurement data 1322 may include the tooth receiving cavities of a dental appliance that do not properly fit on the patient's teeth. In some embodiments, the measurement data 1322 may include a magnitude of the and improper fit of the dental appliance such as we distance between and includes all or a incisal surface of a tooth receiving cavity and a corresponding occlusal or incisal surface of a corresponding tooth.

In some embodiments, the measurement data 1322 may include the above-described data for each of the stages of the treatment plan and may further include rates of change and other information determined based on the differences between the patient's teeth and orthodontic appliances used for treatment over multiple stages of the treatment plan. In some embodiments, the measurement data 1322 includes per-tooth deviations from the current treatment plan in the anterior, left buccal, and right buccal views, as discussed above. In some embodiments, the measurement data 1322 may include measure distances and angles of the deviation between the expected and actual positions and orientations of each tooth. In some embodiments, the measurement data 1322 may include both a distance and direction of the deviation of the tooth. For example, the error information may include data indicating that a tooth is not tracking in intrusion and is 0.25 mm from the expected position in the treatment plan.

The virtual dental care datastore(s) 120 may include treatment plan data 1324. The treatment plan data 1324 may include the positions and orientations of each of the patient's teeth for each stage of a treatment plan 1514. In some embodiments, the positions and orientations of the teeth may be stored as three-dimensional positional locations and angular orientations of each tooth and the patient's upper and lower arches. In some embodiments the positions and orientations of the patient's teeth may be stored as a collection of three-dimensional segmented models of the patient's upper and lower arches for each stage of treatment. In some embodiments, the treatment plan data may include other information such as the location of attachments on the patient's teeth, and other orthodontic devices such as wire and bracket braces, elastics, temporary anchorage devices, and other orthodontic devices.

The virtual dental care datastore(s) 120 may include guidance information 1326. The guidance information 1326 may include a doctor's guidance template data 1512. The doctor's guidance template data 1512 may include information including threshold values that the doctor uses for tracking a treatment plan and determining potential variations in treatment and guidance to provide to the patient based on the threshold values. For example, the thresholds values could be as specific as if the central incisors deviate from the treatment plan by 0.75 mm, the guidance should be sent to the patient to schedule a new appointment, if one of the central incisors deviation between 0.5-0.75 mm from the treatment plan, then further deviations should be watched, if the central incisor deviations increase over a period of 2 months should result in a new appointment, if the central incisor deviations are between 0.25 to 0.5 mm, then the patient should be given guidance to wear the current set of aligners for an additional week, and central incisor deviations less than 0.25 mm can be considered "on-track". Other thresholds may specify that teeth marked "Do No Move" according to the treatment plan should not deviate from their treatment position and any deviation greater than 0.25 mm should result in an appointment.

The guidance information 1326 may also include case-by-case guidance 1516 based on one or more of the particular treatment plan and the particular patient. For example, a treatment plan with a particularly out of place tooth may have case specific thresholds that are higher or lower than the thresholds in the doctor's guidance template or, for example, the patient may be missing one or more teeth and accordingly the case-by-case guidance data may omit any thresholds related to the missing teeth or may include patient specific thresholds related to closing a gap formed by the missing tooth.

The virtual dental care datastore(s) 120 may include historical data 1323. The historical data 1323 may include information related to guidance previously provided to the patient and historical measurement information 1524. The use of historical data 1323 may allow guidance thresholds to be written with a temporal frame of reference. For example, the guidance thresholds may include things such as if a condition worsens over a certain number of weeks then provide the particular type of guidance.

The modules 1102 may include a guidance generation module 1304. The guidance generation module receives the measurement data 1322, the treatment plan data 1322, guidance information 1326, and the historical data 1323 and uses this information to apply the guidance to the patient's current dental occlusion, such as the position of the patient's teeth, with respect to the expected occlusion in the treatment plan. For example, the guidance may include a threshold such as if the incisor's position as determined by the measurement data 1322 is greater than 0.5 mm from the expected position, then send guidance to the patient to schedule an appointment, or by incorporating historical data, if the deviation of the incisor's position increases by more than 0.1 in two consecutive stages then send guidance to the patient to schedule an appointment. In some embodiments, for example in which treatment plans include the use of attachments, the guidance generation module may generate guidance to the patient or the doctor based on the absence or detachment of an attachment.

The guidance may also include guidance related to the timing of switching aligners for example guidance to where the dental liner for an additional amount of time before changing to the aligner for the next stage of treatment or to change to the next stage at an earlier time. The guidance may also include instructions to wear a retainer or switch from an aligner to a retainer. The guidance may further include instructions relating to proper seating of the aligner, such as how the aligner should look or feel when properly seated, including, for example a distance between the aligner and the gingiva. Other interventions or guidance may include instructions on how to use and when to use chewies, when to schedule an orthodontic follow-up appointment, and other guidance. The guidance may also include instructions to the doctor or example to contact the patient for follow-up appointment or to guide the next steps of treatment and suggested interventions for consideration by the doctor. In other examples, the patient may not be contacted directly.

In some embodiments, conflicting guidance or duplicative guidance may be given to the patient based on differences in one or more of the guidance template and the case-by-case guidance. For example, a patient may have multiple issues, more than one of which may result in providing guidance to the patient to schedule an appointment while other guidance may suggest to the that the patient immediately see the doctor. In such cases the guidance deconfliction module 1306 may determine that the patient should only receive guidance to immediately see the doctor rather than to both immediately see the doctor and schedule an appointment. In some embodiments, the threshold may indicate that guidance should be provided for the patient to use a chewie on the first premolar and another threshold may indicate that guidance should be provided for the patient to use a chewie on the second premolar on the same side. Here, only one chewie is needed, accordingly, the guidance may be deconflicted to indicate that the patient should use a single chewie on the first and second premolars. In this way the guidance the confliction module 1306 can prevent the system from providing conflicting or confusing guidance to the patient.

The modules 1102 may include a guidance and intervention transmission module 1308. The guidance and intervention transmission module 1308 may transmit guidance or intervention information to one or more of the patient and the doctor. The guidance or intervention information may be sent via many means. For example, the guidance may be sent via text message, email, smart phone or browser-based application notifications, automated telephone calls, calendar invites, or other forms of messaging and communication. In some embodiments the guidance may include both text and audiovisual information, such as a video or image showing the proper use of a chewie.

Figure 14:
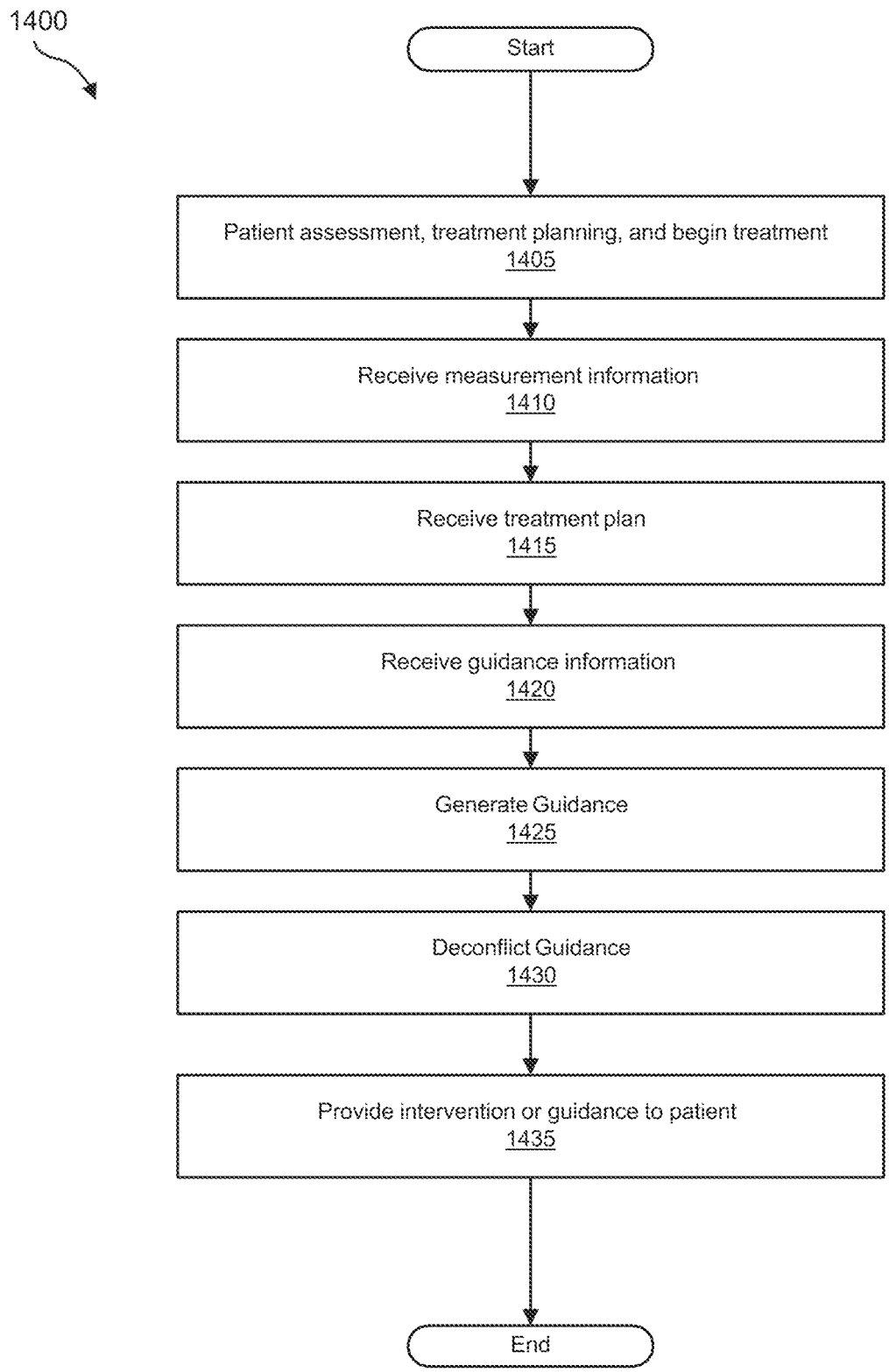
FIG. 14 shows a method of providing guidance, according to embodiments herein, according to embodiments herein.
Figure 15:
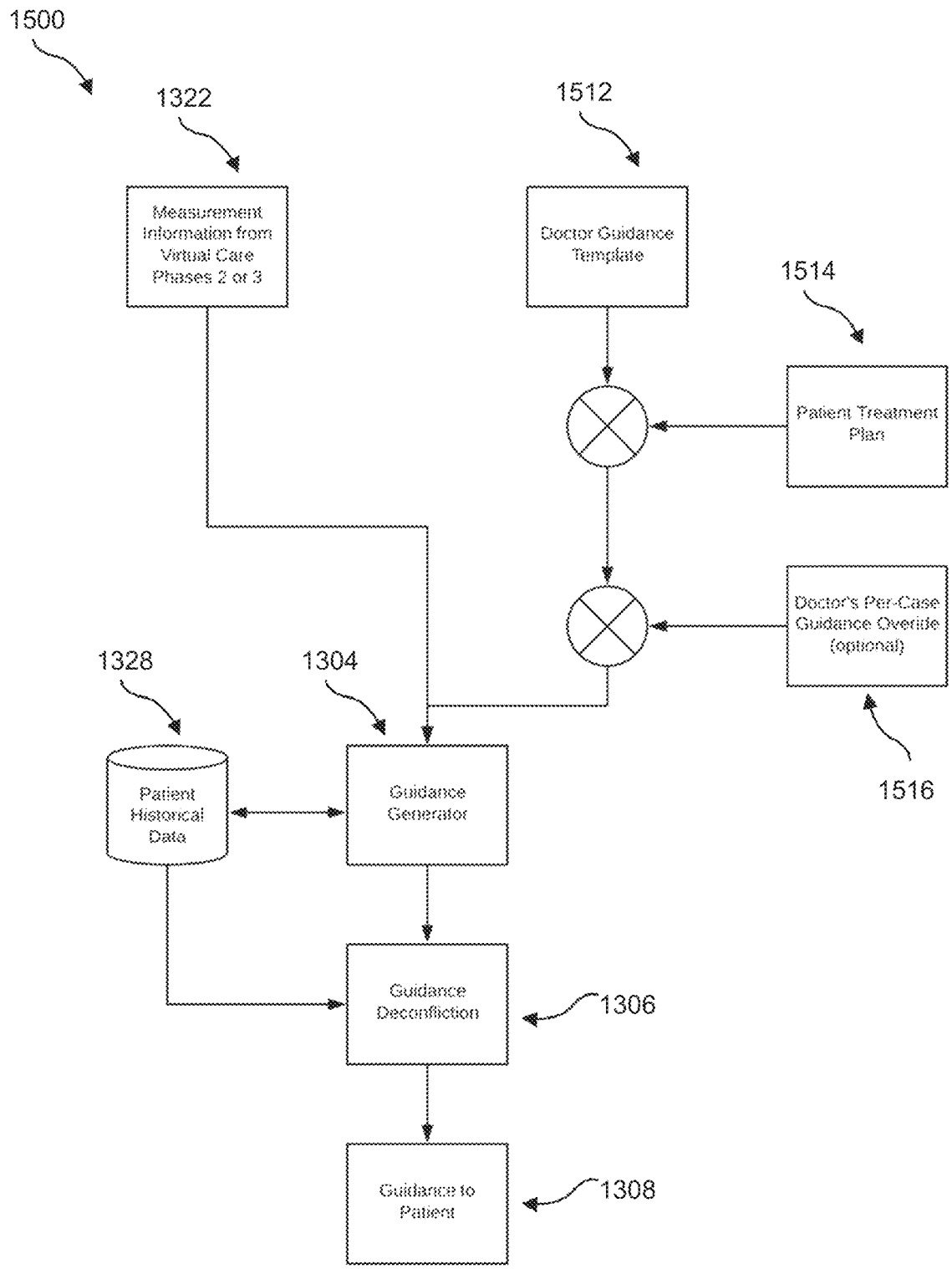
FIG. 15 shows a process flow diagram for generating and providing orthodontic guidance to a patient, according to embodiments herein.

FIG. 14 is a flow diagram of an exemplary computer-implemented method 1400 for determining and providing guidance. FIG. 15 is a process and information flow diagram 1350 of the exemplary computer-implemented method 1300 for determining and providing guidance. The steps and information flow shown in FIGS. 14 and 15 may be performed by any suitable computer-executable code and/or computing system, including the system(s) illustrated in FIGS. 1 and 13. In one example, each of the steps shown in FIGS. 14 and 15 may represent an algorithm whose structure includes and/or is represented by multiple sub-steps, examples of which will be provided in greater detail below.

With reference to FIGS. 14 and 15, at step 1405 the patient assessment, treatment planning, and the beginning of treatment may occur, for example as discussed above with reference to step 2002 of FIG. 20. At step 1410 the guidance generation module 1304 receives measurement data 1322. The measurement data 1322 may include two-dimensional images received from a patient over a communication network. In some embodiments, measurement data 1322 may include error data 628 received from, for example, the error module 610.

At step 1415 the guidance generation module 1304 receives the treatment plan data 1514. In some embodiments, guidance generation module 1304 receives the treatment plan data 1514 from the treatment planning system or module.

At step 1420 the guidance generation module 1304 receives the guidance information the guidance information may include both the doctors guidance template information 1514 and the case-by-case guidance information 1516.

At step 1425 the guidance generation module 1304 uses the received information from step 1420 and applies the received guidance to the patient's current dental occlusion based on the measurement data 1322 and the treatment plan data 1514. As discussed above, the guidance may include guidance related to the timing of switching aligners for example guidance to where the dental liner for an additional amount of time before changing to the aligner for the next stage of treatment or to change to the next stage at an earlier time based on thresholds as discussed above. The guidance may also include instructions to switch from wearing an aligner to a wearing retainer. The guidance may further include instructions relating to proper aligner seating, such as how the aligner should look or feel when properly seated, including, for example a distance between the aligner and the gingiva. Other interventions or guidance may include instructions on how to use and when to use chewies, when to schedule an orthodontic follow-up appointment, and other guidance. In some embodiments, for example in which treatment plans include the use of attachments, the guidance generation module may generate guidance to the patient or the doctor based on the absence or detachment of an attachment.

At step 1430 the guidance the confliction module 1306 the conflicts the guidance provided by the guidance generation module 1304. For example, the confliction module 1306 may determine that the patient should only receive guidance to immediately see the doctor rather than to both immediately see the doctor and schedule an appointment. In some embodiments, the threshold may indicate that guidance should be provided for the patient to use a chewie on the first premolar and another threshold may indicate that guidance should be provided for the patient to use a chewie on the second premolar on the same side. Here, only one chewie is needed, accordingly, the confliction module 1306 may indicate that the patient should use a single chewie on the first and second premolars. In this way, the system may be prevented from providing conflicting or confusing guidance to the patient.

At step 1435 the guidance and intervention transmission module 1308 may transmit guidance or intervention information to one or more of the patient and the doctor. At step 1435 the guidance or intervention information may be sent via many means. For example, the guidance may be sent via text message, email, smart phone or browser-based application notifications, automated telephone calls, calendar invites, or other forms of messaging and communication. In some embodiments, the guidance may include both text and audiovisual information, such as a video or image showing the proper use of a chewie. In other embodiments, the patient may not be directly contacted. For example, the doctor may maintain a list of guidance information to relate to the patient during the patient's next scheduled appointment.

In some embodiments, the guidance generation module 1304 may indicate that the treatment intervention may be desired, for example, when the positions of the teeth have deviated to the point where a new treatment planning process should begin to generate new stages of treatment to move the teeth from a current position towards the desired final position.

Photo Based Treatment Refinement

The practice of medicine is rapidly evolving toward tele-medicine—the remote treatment of patients. By using the above described systems and methods a doctor may remotely assess the patient's treatment progress and in the rare cases when the patient's progress becomes so off-track as to warrant a revised treatment plan, the images captured using the artificial intelligence guidance, discussed above, along with the segmented dental scans generated at the initiation of treatment may be used to prescribe a secondary order for an off-track patient using only their primary treatment plan data and a set of orthodontic photographs taken by the patient with a phone camera, without rescanning the patient or calling the patient back into the office.

Figure 16:
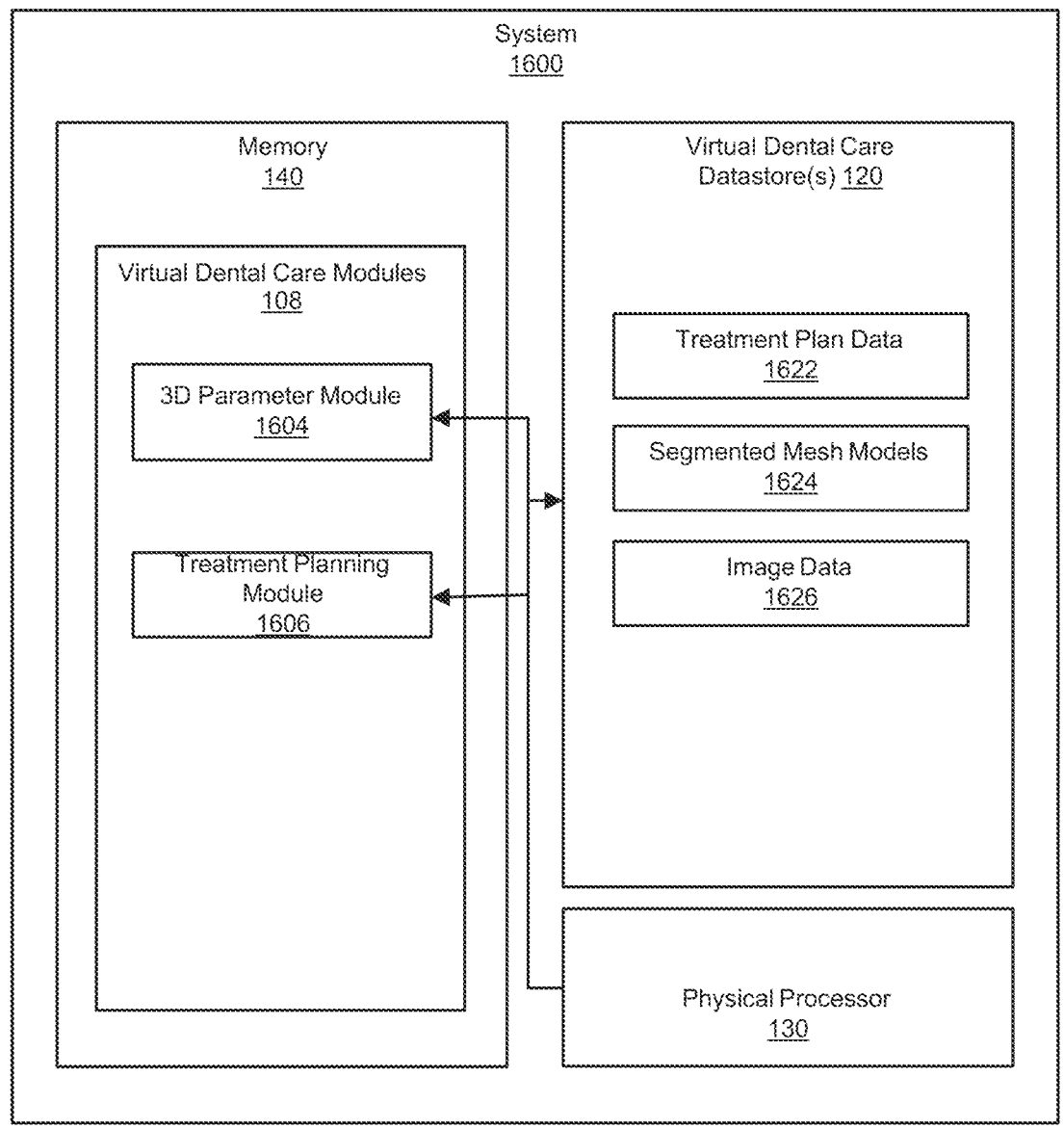
FIG. 16 shows a block diagram of an example system for off-track treatment planning, according to embodiments herein.

FIG. 16 shows a block diagram of an example system for off-track treatment planning. As illustrated in this figure, example system 1600 may include one or more virtual dental care modules 108 for performing one or more tasks. As will be explained in greater detail below, virtual dental care modules 108 may include a three dimensional parameterization module 1604 and a treatment planning module 1606. Although illustrated as separate elements, one or more of virtual dental care modules 108 in FIG. 16 may represent portions of a single module or application.

In certain embodiments, one or more of virtual dental care modules 108 in FIG. 16 may represent one or more software applications or programs that, when executed by a computing device, may cause the computing device to perform one or more tasks. For example, and as will be described in greater detail below, one or more of virtual dental care modules 108 may represent modules stored and configured to run on one or more computing devices, such as the devices illustrated in FIG. 1A (e.g., computing device 102 and/or server 106). One or more of virtual dental care modules 108 in FIG. 16 2 may also represent all or portions of one or more special-purpose computers configured to perform one or more tasks.

As illustrated in FIG. 16, example system 1600 may also include one or more virtual dental care datastore(s) 120, such as treatment plan data 1622, segmented mesh models 1624, and image data 1626. Virtual dental care datastore(s) 120 may include one or more datastores configured to store any type or form of data or information.

Virtual dental care datastore(s) 120 may include treatment plan data 1622. The treatment plan data 1622 may include the positions and orientations of each of the patient's teeth for each stage of a treatment plan. In some embodiments, the positions and orientations of the teeth may be stored as three-dimensional positional locations and angular orientations of each tooth and the patient's upper and lower arches. In some embodiments the positions and orientations of the patient's teeth may be stored as a collection of three-dimensional segmented models of the patient's upper and lower arches for each stage of treatment. In some embodiments, the treatment plan data may include other information such as the location of attachments on the patient's teeth, and other orthodontic devices such as wire and bracket braces, elastics, temporary anchorage devices, and other orthodontic devices.

Virtual dental care datastore(s) 120 may include segmented mesh models 1624. In some embodiments the segmented mesh models of the patient's teeth may be stored separately from the treatment plan data. The segmented mesh models may include three-dimensional mesh models of each of the patient's teeth.

Virtual dental care datastore(s) 120 may include image data 1626. The image data 1626 may include a two-dimensional image data, such as the two-dimensional image data captured using the artificial intelligence guidance, as discussed above.

The three-dimensional parameterization module 1604 receives the treatment plan data 1622 and the image data 1626 and uses the data to generate a three-dimensional model of the patient's dentition at a current position by determining the appropriate positions for the patient's teeth and placing the segmented tooth models from the treatment plan data into those positions. The three-dimensional parameterization model 1604 may use information such as the error data discussed above in order to determine the three-dimensional positions of the patient's teeth. In some embodiments, in addition to the three buccal images discussed above, upper and lower arch occlusal photos may also be used in order to determine the three-dimensional positions of the patient's teeth. Various methods may be used to align the three-dimensional models of the patient's teeth with the two-dimensional images of the patient's teeth. For example, in some embodiments a differential rendering algorithm may be used to align the teeth or an expectation-maximization algorithm may be used to match the position and orientation of the three-dimensional models of the patient's teeth with a corresponding locations and orientations of the teeth in the two-dimensional image. The three-dimensional parameterization module 1604 may output a new segmented dental mesh model of the patient's teeth in their current positions.

The treatment planning module 1606 may use the new segmented dental mesh model output by the three-dimensional parameterization module 1604 along with the treatment plan information in order to generate a revised treatment plan to move the patient's teeth from the new current position to the desired final position. In some embodiments, the revised treatment plan may move the teeth to a different, new desired final position.

Figure 17:
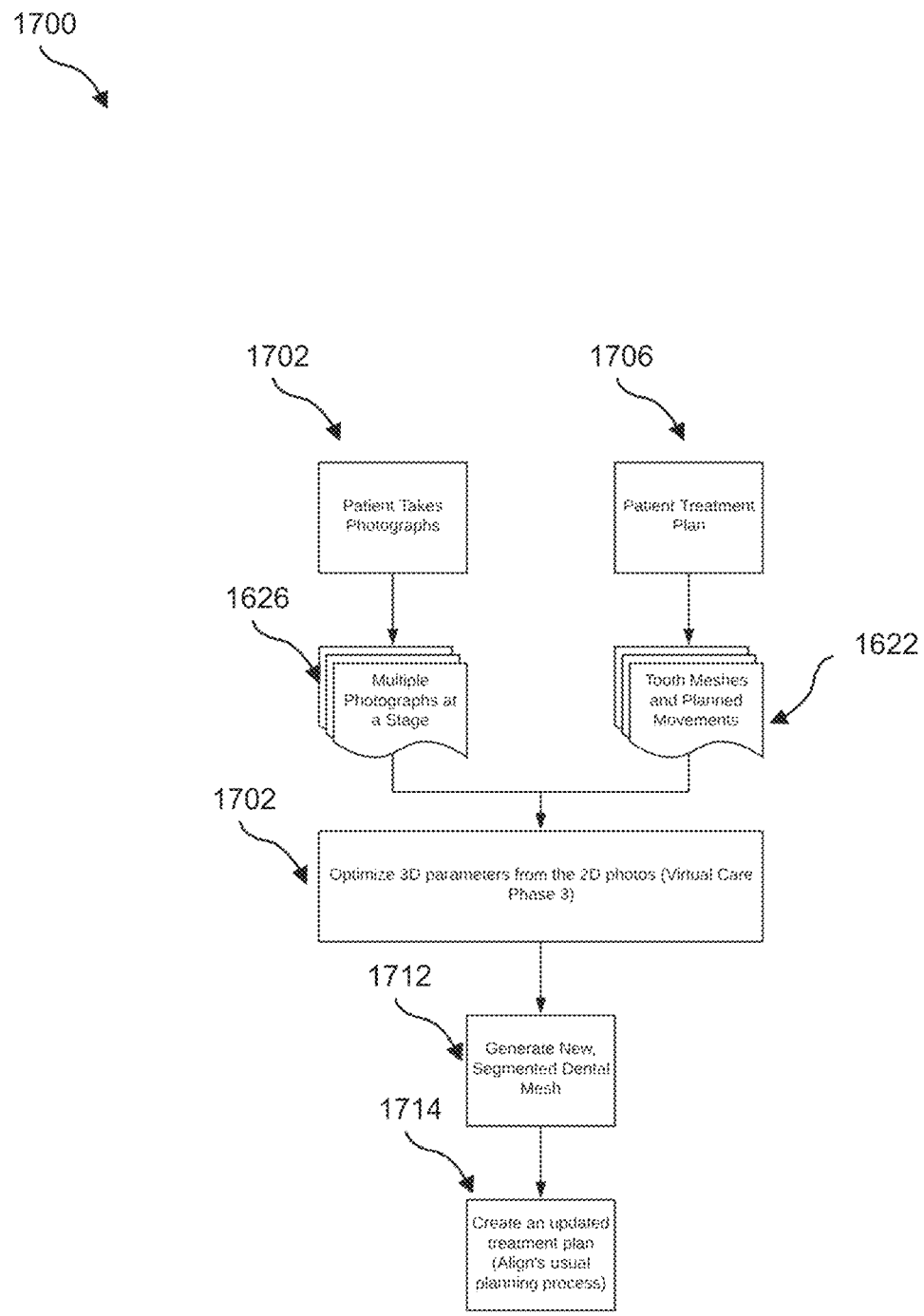
FIG. 17 shows a method of generating a treatment plan for off-track treatment of a patient, according to embodiments herein.

FIG. 17 is a flow diagram of an exemplary computer-implemented method 17 300 for photo based treatment refinement. The steps shown in FIG. 17 may be performed by any suitable computer-executable code and/or computing system, including the system(s) illustrated in FIGS. 1 and 16. In one example, each of the steps shown in FIG. 17 may represent an algorithm whose structure includes and/or is represented by multiple sub-steps, examples of which will be provided in greater detail below.

At step 1702 a patient takes two-dimensional photographs 1626 of their teeth. The photographs may include a left buccal, a right buccal, an anterior, and upper and lower occlusal the use of the patient's teeth. The capturing of the two-dimensional photographs 1626 may be guided by the artificial intelligence guidance system discussed above.

At step 1706 a treatment plan is gathered. The treatment plan may be gathered or generated, as discussed above. The treatment plan 1622 may include tooth meshes and the planned movements of the teeth for the initial treatment of the patient's dentition.

At step 1710 the three-dimensional parameterization module 1604 receives the treatment plan data 1622 and the image data 1626 and uses the data to generate a three-dimensional model of the patient's dentition at a current position by determining the appropriate positions for the patient's teeth and placing the segmented tooth models from the treatment plan data into those positions. The three-dimensional parameterization model 1604 may use information such as the error data discussed above in order to determine the three-dimensional positions of the patient's teeth. In some embodiments, in addition to the three buccal images discussed above, upper and lower arch occlusal photos may also be used in order to determine the three-dimensional positions of the patient's teeth. Various methods may be used to align the three-dimensional models of the patient's teeth with the two-dimensional images of the patient's teeth. For example, in some embodiments a differential rendering algorithm may be used to align the teeth or an expectation-maximization algorithm may be used to match the position and orientation of the three-dimensional models of the patient's teeth with a corresponding locations and orientations of the teeth in the two-dimensional image.

At step 1712 the three-dimensional parameterization module 1604 may output a new segmented dental mesh model of the patient's teeth in their current positions. FIG. 18 shows segmented mesh teeth arches generated from existing scans of a patient's teeth and 2D images for a patent's teeth using the algorithms discussed above, according to embodiments herein. The alignment 1810 shows the alignment of a mesh depicting expected position of the patient's teeth 1804 according to the treatment plan with a mesh of the actual current position of the patient's teeth 1802 generated using the segmented three-dimensional models of the patient's teeth and the two-dimensional images captured by the patient.

The alignment 1820 shows the alignment of a mesh depicting the alignment of the three-dimensional mesh models 1806 of the patient's teeth from the treatment plan with a mesh of the actual current position of the patient's teeth 1802 generated using the segmented three-dimensional models of the patient's teeth and the two-dimensional images captured by the patient. The close agreement between the two models shows that the algorithms discussed above produce meshes of suitable accuracy for use in treatment planning without rescanning the patient's teeth.

At step 1714 treatment planning module 1606 may use the new segmented dental mesh model output by the three-dimensional parameterization module 1604 along with the treatment plan information in order to generate a revised treatment plan to move the patient's teeth from the new current position to the desired final position. In some embodiments, the revised treatment plan may move the teeth to a different, new desired final position.

The updated treatment plan may be used to fabricate new dental appliances to move the patient's teeth from the new current position to a desired final position.

Computing System

Figure 19:
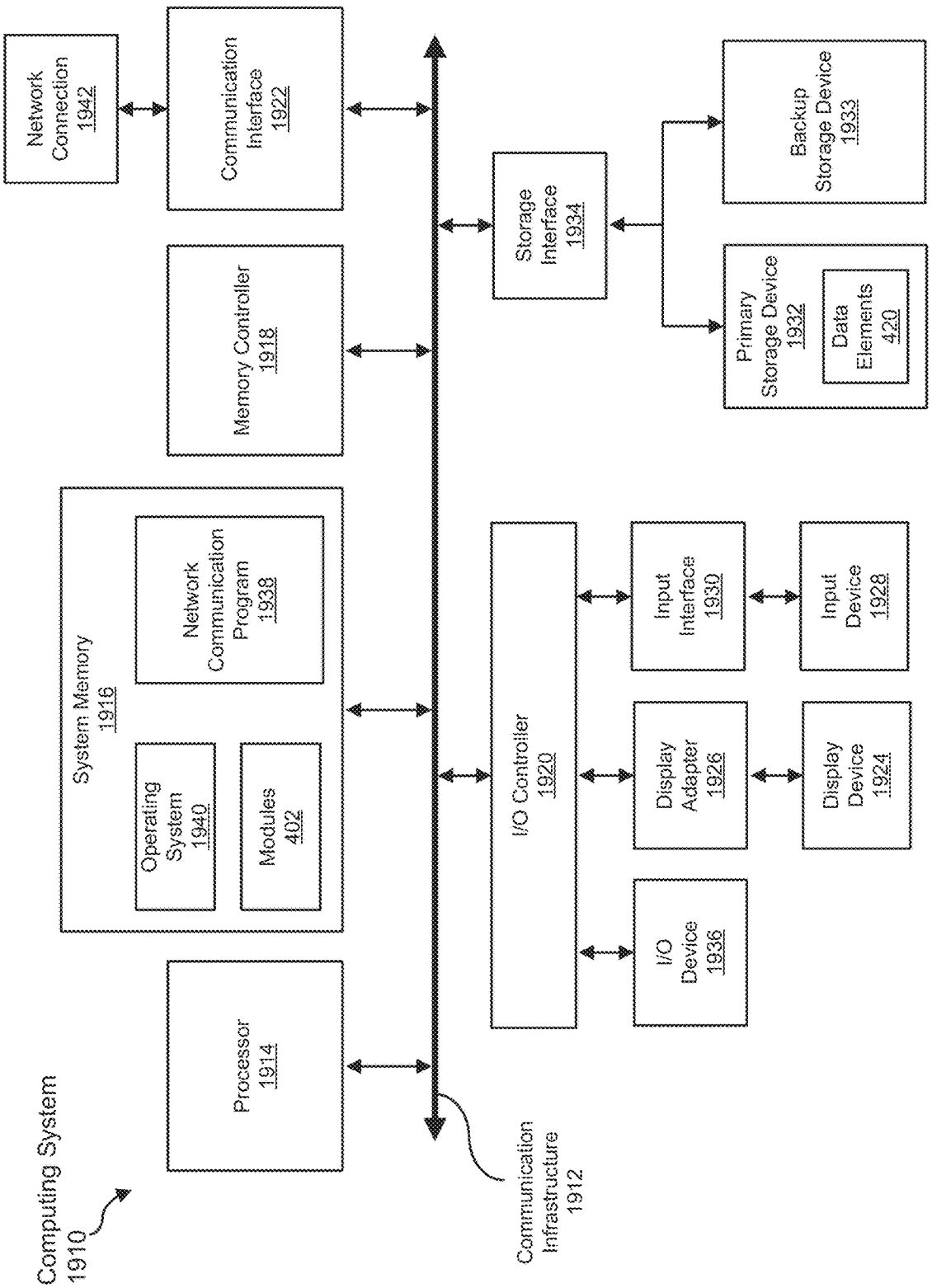
FIG. 19 shows a block diagram of an example computing system capable of implementing one or more embodiments described and/or illustrated herein, in accordance with some embodiments.

FIG. 19 is a block diagram of an example computing system 1910 capable of implementing one or more of the embodiments described and/or illustrated herein. For example, all or a portion of computing system 1910 may perform and/or be a means for performing, either alone or in combination with other elements, one or more of the steps described herein (such as one or more of the steps illustrated in FIGS. 3, 7, 14, 15, and 17). All or a portion of computing system 1910 may also perform and/or be a means for performing any other steps, methods, or processes described and/or illustrated herein.

Computing system 1910 broadly represents any single or multi-processor computing device or system capable of executing computer-readable instructions. Examples of computing system 1910 include, without limitation, workstations, laptops, client-side terminals, servers, distributed computing systems, handheld devices, or any other computing system or device. In its most basic configuration, computing system 1910 may include at least one processor 1914 and a system memory 1916.

Processor 1914 generally represents any type or form of physical processing unit (e.g., a hardware-implemented central processing unit) capable of processing data or interpreting and executing instructions. In certain embodiments, processor 1914 may receive instructions from a software application or module. These instructions may cause processor 1914 to perform the functions of one or more of the example embodiments described and/or illustrated herein.

System memory 1916 generally represents any type or form of volatile or non-volatile storage device or medium capable of storing data and/or other computer-readable instructions. Examples of system memory 1916 include, without limitation, Random Access Memory (RAM), Read Only Memory (ROM), flash memory, or any other suitable memory device. Although not required, in certain embodiments computing system 1910 may include both a volatile memory unit (such as, for example, system memory 1916) and a non-volatile storage device (such as, for example, primary storage device 1932, as described in detail below). In one example, one or more of virtual dental care modules 108 from FIG. 1A may be loaded into system memory 1916.

In some examples, system memory 1916 may store and/or load an operating system 1940 for execution by processor 1914. In one example, operating system 1940 may include and/or represent software that manages computer hardware and software resources and/or provides common services to computer programs and/or applications on computing system 1910. Examples of operating system 1940 include, without limitation, LINUX, JUNOS, MICROSOFT WINDOWS, WINDOWS MOBILE, MAC OS, APPLE'S IOS, UNIX, GOOGLE CHROME OS, GOOGLE'S ANDROID, SOLARIS, variations of one or more of the same, and/or any other suitable operating system.

In certain embodiments, example computing system 1910 may also include one or more components or elements in addition to processor 1914 and system memory 1916. For example, as illustrated in FIG. 19, computing system 1910 may include a memory controller 1918, an Input/Output (I/O) controller 1920, and a communication interface 1922, each of which may be interconnected via a communication infrastructure 1912. Communication infrastructure 1912 generally represents any type or form of infrastructure capable of facilitating communication between one or more components of a computing device. Examples of communication infrastructure 1912 include, without limitation, a communication bus (such as an Industry Standard Architecture (ISA), Peripheral Component Interconnect (PCI), PCI Express (PCIe), or similar bus) and a network.

Memory controller 1918 generally represents any type or form of device capable of handling memory or data or controlling communication between one or more components of computing system 1910. For example, in certain embodiments memory controller 1918 may control communication between processor 1914, system memory 1916, and I/O controller 1920 via communication infrastructure 1912.

I/O controller 1920 generally represents any type or form of module capable of coordinating and/or controlling the input and output functions of a computing device. For example, in certain embodiments I/O controller 1920 may control or facilitate transfer of data between one or more elements of computing system 1910, such as processor

1914, system memory 1916, communication interface 1922, display adapter 1926, input interface 1930, and storage interface 1934.

As illustrated in FIG. 19, computing system 1910 may also include at least one display device 1924 coupled to I/O controller 1920 via a display adapter 1926. Display device 1924 generally represents any type or form of device capable of visually displaying information forwarded by display adapter 1926. Similarly, display adapter 1926 generally represents any type or form of device configured to forward graphics, text, and other data from communication infrastructure 1912 (or from a frame buffer, as known in the art) for display on display device 1924.

As illustrated in FIG. 19, example computing system 1910 may also include at least one input device 1928 coupled to I/O controller 1920 via an input interface 1930. Input device 1928 generally represents any type or form of input device capable of providing input, either computer or human generated, to example computing system 1910. Examples of input device 1928 include, without limitation, a keyboard, a pointing device, a speech recognition device, variations or combinations of one or more of the same, and/or any other input device.

Additionally or alternatively, example computing system 1910 may include additional I/O devices. For example, example computing system 1910 may include I/O device 1936. In this example, I/O device 1936 may include and/or represent a user interface that facilitates human interaction with computing system 1910. Examples of I/O device 1936 include, without limitation, a computer mouse, a keyboard, a monitor, a printer, a modem, a camera, a scanner, a microphone, a touchscreen device, variations or combinations of one or more of the same, and/or any other I/O device.

Communication interface 1922 broadly represents any type or form of communication device or adapter capable of facilitating communication between example computing system 1910 and one or more additional devices. For example, in certain embodiments communication interface 1922 may facilitate communication between computing system 1910 and a private or public network including additional computing systems. Examples of communication interface 1922 include, without limitation, a wired network interface (such as a network interface card), a wireless network interface (such as a wireless network interface card), a modem, and any other suitable interface. In at least one embodiment, communication interface 1922 may provide a direct connection to a remote server via a direct link to a network, such as the Internet. Communication interface 1922 may also indirectly provide such a connection through, for example, a local area network (such as an Ethernet network), a personal area network, a telephone or cable network, a cellular telephone connection, a satellite data connection, or any other suitable connection.

In certain embodiments, communication interface 1922 may also represent a host adapter configured to facilitate communication between computing system 1910 and one or more additional network or storage devices via an external bus or communications channel. Examples of host adapters include, without limitation, Small Computer System Interface (SCSI) host adapters, Universal Serial Bus (USB) host adapters, Institute of Electrical and Electronics Engineers (IEEE) 1394 host adapters, Advanced Technology Attachment (ATA), Parallel ATA (PATA), Serial ATA (SATA), and External SATA (eSATA) host adapters, Fibre Channel interface adapters, Ethernet adapters, or the like. Communication interface 1922 may also allow computing system 1910 to engage in distributed or remote computing. For example, communication interface 1922 may receive instructions from a remote device or send instructions to a remote device for execution.

In some examples, system memory 1916 may store and/or load a network communication program 1938 for execution by processor 1914. In one example, network communication program 1938 may include and/or represent software that enables computing system 1910 to establish a network connection 1942 with another computing system (not illustrated in FIG. 19) and/or communicate with the other computing system by way of communication interface 1922. In this example, network communication program 1938 may direct the flow of outgoing traffic that is sent to the other computing system via network connection 1942. Additionally or alternatively, network communication program 1938 may direct the processing of incoming traffic that is received from the other computing system via network connection 1942 in connection with processor 1914.

Although not illustrated in this way in FIG. 19, network communication program 1938 may alternatively be stored and/or loaded in communication interface 1922. For example, network communication program 1938 may include and/or represent at least a portion of software and/or firmware that is executed by a processor and/or Application Specific Integrated Circuit (ASIC) incorporated in communication interface 1922.

As illustrated in FIG. 19, example computing system 1910 may also include a primary storage device 1932 and a backup storage device 1933 coupled to communication infrastructure 1912 via a storage interface 1934. Storage devices 1932 and 1933 generally represent any type or form of storage device or medium capable of storing data and/or other computer-readable instructions. For example, storage devices 1932 and 1933 may be a magnetic disk drive (e.g., a so-called hard drive), a solid state drive, a floppy disk drive, a magnetic tape drive, an optical disk drive, a flash drive, or the like. Storage interface 1934 generally represents any type or form of interface or device for transferring data between storage devices 1932 and 1933 and other components of computing system 1910. In one example, virtual dental care datastore(s) 120 from FIG. 1A may be stored and/or loaded in primary storage device 1932.

In certain embodiments, storage devices 1932 and 1933 may be configured to read from and/or write to a removable storage unit configured to store computer software, data, or other computer-readable information. Examples of suitable removable storage units include, without limitation, a floppy disk, a magnetic tape, an optical disk, a flash memory device, or the like. Storage devices 1932 and 1933 may also include other similar structures or devices for allowing computer software, data, or other computer-readable instructions to be loaded into computing system 1910. For example, storage devices 1932 and 1933 may be configured to read and write software, data, or other computer-readable information. Storage devices 1932 and 1933 may also be a part of computing system 1910 or may be a separate device accessed through other interface systems.

Many other devices or subsystems may be connected to computing system 1910. Conversely, all of the components and devices illustrated in FIG. 19 need not be present to practice the embodiments described and/or illustrated herein. The devices and subsystems referenced above may also be interconnected in different ways from that shown in FIG. 19. Computing system 1910 may also employ any number of software, firmware, and/or hardware configurations. For example, one or more of the example embodiments disclosed herein may be encoded as a computer program (also referred to as computer software, software applications, computer-readable instructions, or computer control logic) on a computer-readable medium. The term "computer-readable medium," as used herein, generally refers to any form of device, carrier, or medium capable of storing or carrying computer-readable instructions. Examples of computer-readable media include, without limitation, transmission-type media, such as carrier waves, and non-transitory-type media, such as magnetic-storage media (e.g., hard disk drives, tape drives, and floppy disks), optical-storage media (e.g., Compact Disks (CDs), Digital Video Disks (DVDs), and BLU-RAY disks), electronic-storage media (e.g., solid-state drives and flash media), and other distribution systems.

The computer-readable medium containing the computer program may be loaded into computing system 1910. All or a portion of the computer program stored on the computer-readable medium may then be stored in system memory 1916 and/or various portions of storage devices 1932 and 1933. When executed by processor 1914, a computer program loaded into computing system 1910 may cause processor 1914 to perform and/or be a means for performing the functions of one or more of the example embodiments described and/or illustrated herein. Additionally or alternatively, one or more of the example embodiments described and/or illustrated herein may be implemented in firmware and/or hardware. For example, computing system 1910 may be configured as an Application Specific Integrated Circuit (ASIC) adapted to implement one or more of the example embodiments disclosed herein.

Figure 20:
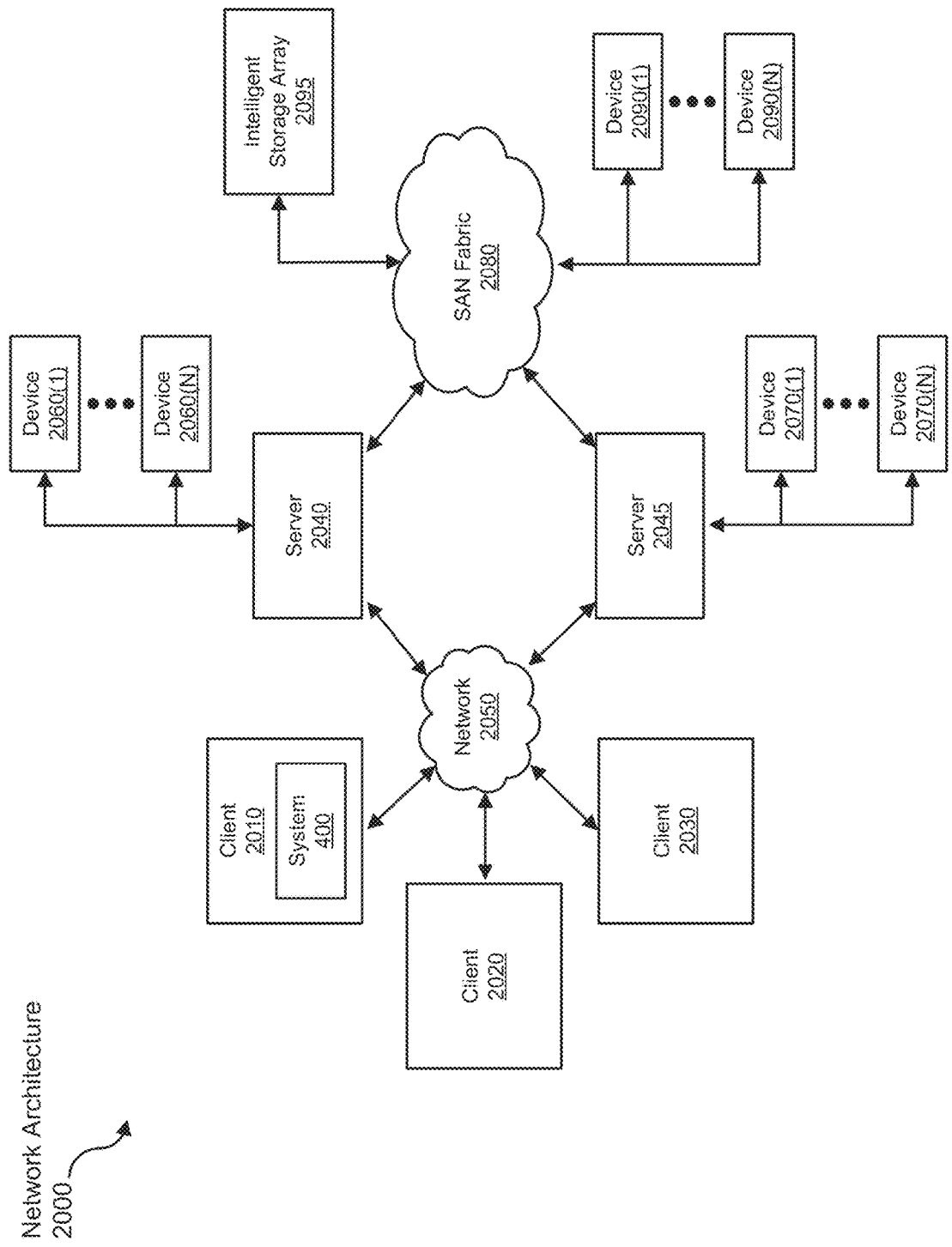
FIG. 20 shows a block diagram of an example computing network capable of implementing one or more of the embodiments described and/or illustrated herein, in accordance with some embodiments.

FIG. 20 is a block diagram of an example network architecture 2000 in which client systems 2010, 2020, and 2030 and servers 2040 and 2045 may be coupled to a network 2050. As detailed above, all or a portion of network architecture 2000 may perform and/or be a means for performing, either alone or in combination with other elements, one or more of the steps disclosed herein (such as one or more of the steps illustrated in FIGS. 3, 7, 14, 15, and 17). All or a portion of network architecture 2000 may also be used to perform and/or be a means for performing other steps and features set forth in the instant disclosure.

Client systems 2010, 2020, and 2030 generally represent any type or form of computing device or system, such as example computing system 1910 in FIG. 19. Similarly, servers 2040 and 2045 generally represent computing devices or systems, such as application servers or database servers, configured to provide various database services and/or run certain software applications. Network 2050 generally represents any telecommunication or computer network including, for example, an intranet, a WAN, a LAN, a PAN, or the Internet. In one example, client systems 2010, 2020, and/or 2030 and/or servers 2040 and/or 2045 may include all or a portion of system 100 from FIG. 1A.

As illustrated in FIG. 20, one or more storage devices 2060(1)-(N) may be directly attached to server 2040. Similarly, one or more storage devices 2070(1)-(N) may be directly attached to server 2045. Storage devices 2060(1)-(N) and storage devices 2070(1)-(N) generally represent any type or form of storage device or medium capable of storing data and/or other computer-readable instructions. In certain embodiments, storage devices 2060(1)-(N) and storage devices 2070(1)-(N) may represent Network-Attached Storage (NAS) devices configured to communicate with servers 2040 and 2045 using various protocols, such as Network File System (NFS), Server Message Block (SMB), or Common Internet File System (CIFS).

Servers 2040 and 2045 may also be connected to a Storage Area Network (SAN) fabric 2080. SAN fabric 2080 generally represents any type or form of computer network or architecture capable of facilitating communication between a plurality of storage devices. SAN fabric 2080 may facilitate communication between servers 2040 and 2045 and a plurality of storage devices 2090(1)-(N) and/or an intelligent storage array 2095. SAN fabric 2080 may also facilitate, via network 2050 and servers 2040 and 2045, communication between client systems 2010, 2020, and 2030 and storage devices 2090(1)-(N) and/or intelligent storage array 2095 in such a manner that devices 2090(1)-(N) and array 2095 appear as locally attached devices to client systems 2010, 2020, and 2030. As with storage devices 2060(1)-(N) and storage devices 2070(1)-(N), storage devices 2090(1)-(N) and intelligent storage array 2095 generally represent any type or form of storage device or medium capable of storing data and/or other computer-readable instructions.

In certain embodiments, and with reference to example computing system 1910 of FIG. 19, a communication interface, such as communication interface 1922 in FIG. 19, may be used to provide connectivity between each client system 2010, 2020, and 2030 and network 2050. Client systems 2010, 2020, and 2030 may be able to access information on server 2040 or 2045 using, for example, a web browser or other client software. Such software may allow client systems 2010, 2020, and 2030 to access data hosted by server 2040, server 2045, storage devices 2060(1)-(N), storage devices 2070(1)-(N), storage devices 2090(1)-(N), or intelligent storage array 2095. Although FIG. 20 depicts the use of a network (such as the Internet) for exchanging data, the embodiments described and/or illustrated herein are not limited to the Internet or any particular network-based environment.

In at least one embodiment, all or a portion of one or more of the example embodiments disclosed herein may be encoded as a computer program and loaded onto and executed by server 2040, server 2045, storage devices 2060(1)-(N), storage devices 2070(1)-(N), storage devices 2090(1)-(N), intelligent storage array 2095, or any combination thereof. All or a portion of one or more of the example embodiments disclosed herein may also be encoded as a computer program, stored in server 2040, run by server 2045, and distributed to client systems 2010, 2020, and 2030 over network 2050.

As detailed above, computing system 1910 and/or one or more components of network architecture 2000 may perform and/or be a means for performing, either alone or in combination with other elements, one or more steps of an example method for virtual care.

Treatment Based Photo Guidance

As discussed herein, to perform virtual orthodontic care, virtual dental care, and/or other remote medicine, the practitioner may wish to visually inspect the patient's dentition. For example, the practitioner may wish to inspect the patient's progress during a treatment plan, diagnose possible issues, and modify the treatment plan as needed. A dental practitioner or the treatment data 138, including a treatment plan, may be used to determine clinically relevant views from which image the patient's teeth.

Using the determined views, as described herein, the systems and methods provided in this disclosure may utilize artificial intelligence or other guidance means to provide a patient with guidance on taking clinically relevant orthodontic photos. The systems and methods provided in this disclosure may improve the functioning of a computing device by more efficiently acquiring image data, which may further reduce storage requirements and network bandwidth. In addition, the systems and methods provided herein may improve the field of virtual medicine by improving the functional capabilities of remote devices.

Figure 21:
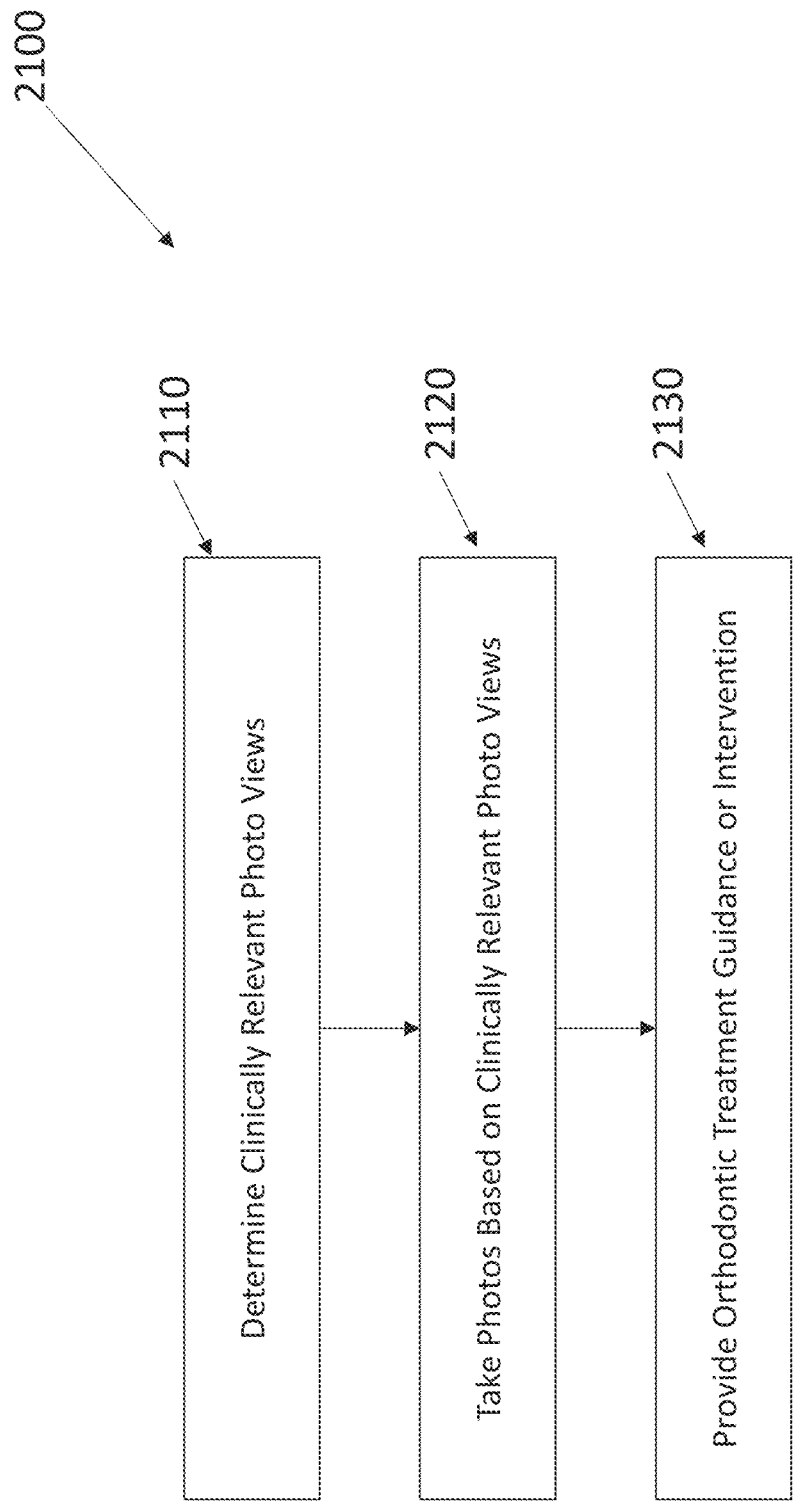
FIG. 21 depicts a method for acquiring and using clinically relevant images of a patient's teeth.

FIG. 21 depicts a method 2100 for acquiring and using clinically relevant images of a patient's teeth. The method may include determining clinically relevant photos views for taking clinically relevant images of the patient's teeth, taking the clinically relevant images of the patient's teeth including providing guidance for the capture of the images, and providing orthodontic treatment guidance or intervention based on the clinically relevant images.

At block 2110 clinically relevant photo or image view are determined. The clinically relevant photo or image views may include one or more of the teeth to be included in the image, a position, an orientation, and a field of view from which to take an image of a patient's dentition. In some embodiments, a dental professional such as the treating orthodontist or dentist may request one or more of the patient's teeth the image from one or more directions. For example, a dental professional may indicate that the upper central incisors included in the images and that the images be acquired from the occlusal direction and the buccal direction. In some embodiments, the treatment plan may be used in order to determine the views from which to take the clinically relevant images.

Figure 22:
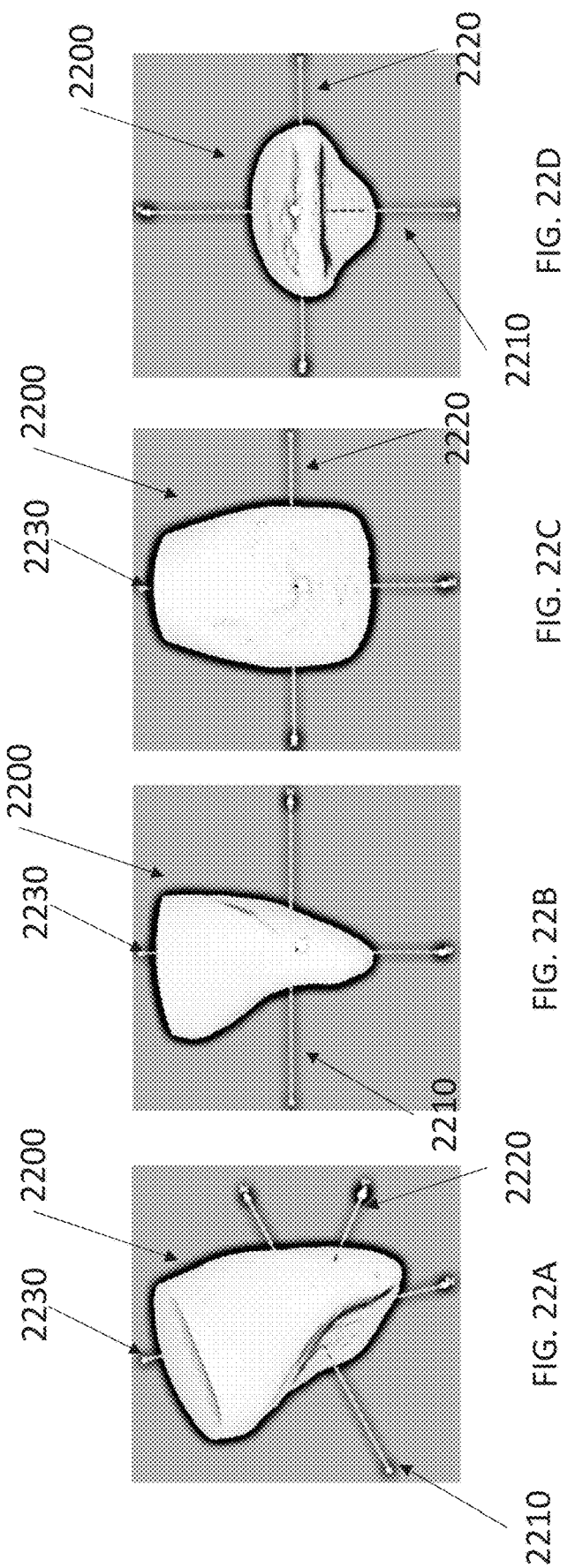
FIGS. 22A, 22B, 22C, and 22D depict teeth and an example set of axes about which a teeth may move, in accordance with some embodiments.

During orthodontic treatment, clinically relevant images are taken in order to capture the movement of the patient's teeth. In order to capture the movement of the patient's teeth the images should be taken from one or more views that are normal to the plane in which the teeth are translating or parallel to the axis about which the patient's teeth are rotating. FIGS. 22A-D depict an example set of axes about which a teeth may move. FIG. 22A depicts an isometric view of an upper central incisor. The mesial-distal axis 2220 may extend through the width of the tooth along the mesial-distal direction and may be referred to as the y-axis, the buccal-lingual axis 2210 may extend through the thickness of the tooth along the buccal-lingual direction and may be referred to as the x-axis, and the occlusal-gingival axis 2230 may extend through the length tooth along the occlusal-gingival direction and may be referred to as the z-axis. In some embodiments the x-axis, y-axis and z-axis are orthogonal to each other.

When a tooth movement for a treatment stage includes translation in the XZ plane shown in FIG. 22B or along the x-axis or z-axis, or includes rotation about the y-axis, then the clinically relevant image of the patient's teeth may include an image taken normal to or displaced from the XZ plane or along the y-axis. When a tooth movement for a treatment stage includes translation in the XY plane shown in FIG. 22D or along the x-axis or y-axis, or includes rotation about the z-axis, then the clinically relevant image of the patient's teeth may include an image taken normal to or displaced from the XY plane or along the z-axis. When a tooth movement for a treatment stage includes translation in the YZ plane shown in FIG. 22C or along the y-axis or z-axis, or includes rotation about the x-axis, then the clinically relevant image of the patient's teeth may include an image taken normal to or displaced from the YZ plane or along the x-axis.

As discussed above, a dental professional may select views for capturing the movement of the patient's teeth. In some embodiments, the treatment plan may be used in order to determine the views from which to take the clinically relevant images. As discussed elsewhere herein, a treatment plan may include a series of stages for moving the patient's teeth from an initial position towards a final position. Each treatment stage may include an initial position of the treatment stage and a final position of the treatment stage. The final position of a first treatment stage may the or correspond to the initial position of a second treatment stage. At block 2210, the virtual dental care system 106 may use the treatment data 138, including the treatment plan data, to determine which teeth are moving during a particular stage of treatment and in which directions and about which axes they are translating and/or rotating. Based on this determination, one or more views for capturing the movement of the patient's teeth may be determined. In some embodiments, determine which teeth are moving may include determining which teeth are scheduled to make a difficult movement during a treatment stage, such as a rotating canine, an intruding tooth, or an extruding tooth.

In some embodiments, the one or more views may be selected from one or more predetermined views. For example, the predetermined views may be a buccal view of the patient's teeth from an buccal direction centered along the patient's midline, one or more buccal views of the patient's teeth taken from a location offset on one side or the other from the patient's midline, for example offset 15°, 30°, 45°, 60°, 75°, and 90° offset to the left and right of the patient's midline, and one or more occlusal views taken from an occlusal position to capture the occlusal or incisal surfaces of the patient's teeth.

In some of embodiments the one or more views may be selected from one or more predetermined views of each of the patient's teeth. For example, the treatment plan may indicate that one or more teeth are moving or rotating in excess of a threshold amount during a particular stage of the treatment plan. The selected views may include a buccal image and an occlusal image of each of the teeth that are moving or rotating in excess of the threshold amount during the stage of the treatment plan. In some embodiments, a single image may capture more than one tooth accordingly views of adjacent teeth that may be within a field of view of an image being system such as a camera may be consolidated. For example, the virtual dental care system 106 after determining the desired clinically relevant views for each tooth may then consolidate one or more views for example of the one or more views of adjacent teeth. For example, in some embodiments of the left and right upper central incisors may be moving during a particular treatment stage accordingly, the virtual dental care system 106 may initially determine that buccal images and occlusal images for both the right and left central upper incisors should be captured, however at a consolidation step the two buccal images may be consolidated into a single buccal image and the two occlusal images may be consolidated into a single occlusal image that captures of teeth.

In some embodiments, at block 2110, patient specific views are determined. For example, the predicted tooth movement during a treatment stage may be assessed and based on the predicted tooth movement a patient specific view may be determined. Although the tooth movements in a treatment plan may be expressed as vectors in the three axes discussed above, not all tooth movements are along one of the orthogonal axes. In some embodiments, the movement of each tooth during each stage of the treatment may be determined and then a position and orientation of the clinically relevant view of the tooth from a perspective that is normal to the tooth movement may be determined in this view or perspective may be a patient specific view for capturing the patient's teeth for the treatment stage.

Figure 23:
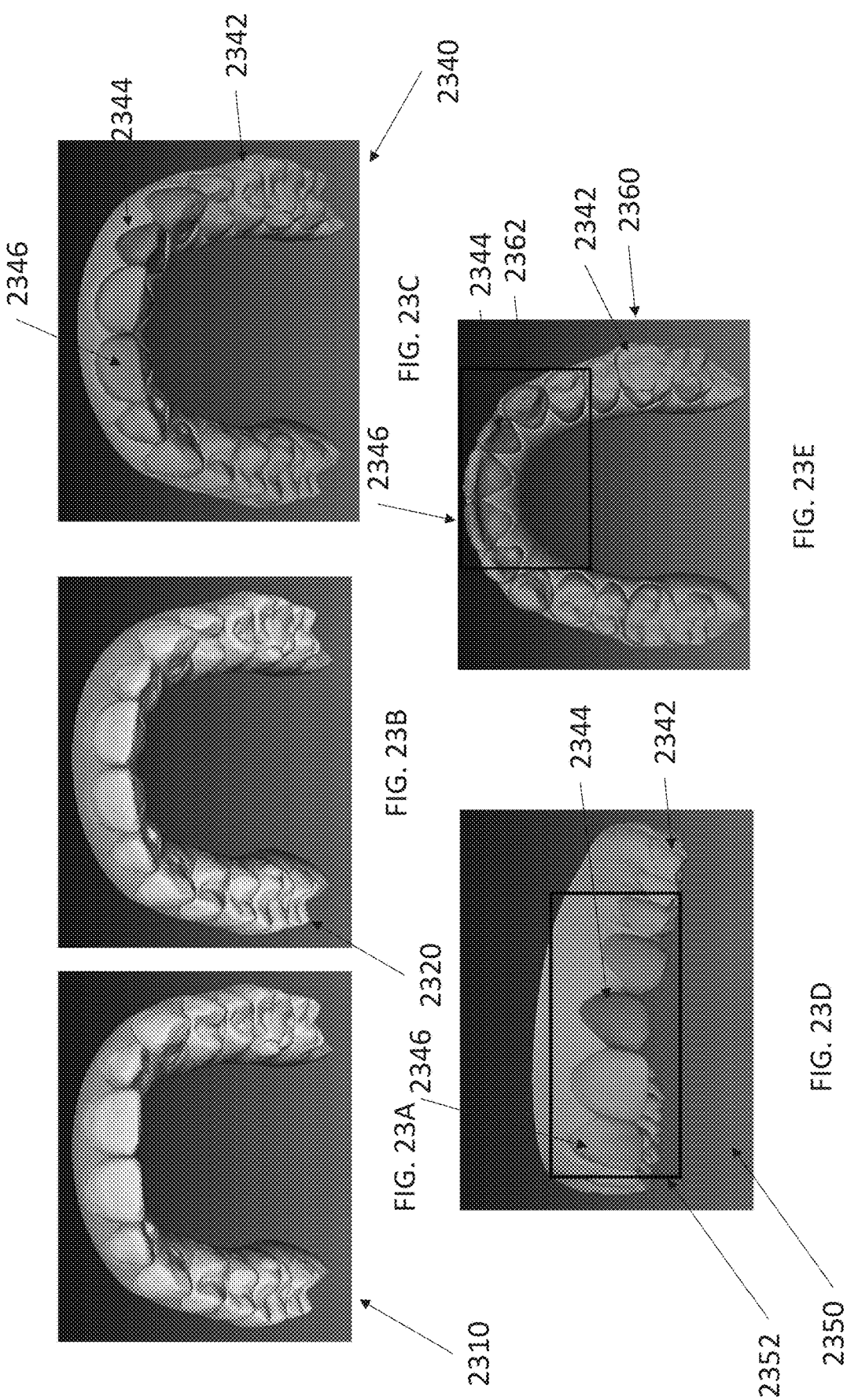
FIGS. 23A 23B, and 23C depict images of a patient's dentition determined based on a treatment plan, in accordance with some embodiments.
FIGS. 23D and 23E depict models of the patient's dentition and clinically relevant views for capturing the movement of the patient's teeth, in accordance with some embodiments.

FIGS. 23A-C depict images determined based on a treatment plan. FIG. 23A depicts a model 2310 of the patient's dentition for a first stage of treatment. The model may include a three-dimensional model formed by connected vertices that depicted the surface of the patient's teeth. FIG. 23B depicts a similar model 2320 of the patient's dentition for a second stage of treatment. FIG. 23C depicts a three-dimensional model 2340 of the patient's teeth for that is color-coded or shaded based on the vertex wise distance between the surfaces of the patient's teeth and the first and second stages. The darker shaded teeth for example tooth 2344 and tooth 2346 are moving during this stage of treatment while tooth 2342 is not moving or moving very little during the state of treatment. At block 210 the virtual dental care system 106 may determined that tooth 2344 and tooth 2346 should be imaged in order to assess the patient's dentition. Based on this determination the virtual dental care system 106 may determine one or more clinically relevant views.

FIG. 23D depicts a model 2350 of the patient's dentition and a first clinically relevant view 2352 for capturing the movement of the patient's teeth 2344 and 2346. View 2352 is a buccal view of the patient's teeth and may capture movement in mesial-distal directions and the occlusal-gingival directions. FIG. 23E depicts a model 2360 which may be the same model 2350 of the patient's dentition and a second clinically relevant view 2362 for capturing the movement of the patient's teeth 2344 and 2346. View 2362 is an occlusal view of the patient's teeth and may capture movement in the buccal-lingual direction and the mesial distal direction. View 2362 may also capture rotation of the teeth about the occlusal-gingival axis.

After determining the clinically relevant views the process may proceed to block 2120. At block 2120 guidance may be provided to acquire photos based on the clinically relevant views. The guidance may be provided as discussed herein with respect to FIGS. 2-5 in the 'Intelligent Photo Guidance' section. For example, one or more systems described herein may receive a clinically relevant view from the virtual dental care system 106 and an image data stream from a camera. For example, camera module 204 may receive image data stream 222 from camera 132 of system 200 or another camera in communication with system 200.

The one or more systems may then compare an image from the image data stream to the clinically relevant view, for example using an artificial intelligence scheme, one or more binary classifications and one or more categorical classifications from the image data stream. For example, AI module 206 may determine binary classifications 224 and categorical classifications 226 from image data stream 222. Based on a determination, the system may provide feedback as to how to change the view provided in the data stream or how to otherwise move the camera to capture the clinically relevant view. In some embodiments, the feedback may include guidance prompts which may refer to audio, visual, and/or haptic prompts that may provide instruction to a user. Examples of guidance prompts may include, without limitation, overlays on a device screen, text notifications, oral instructions, a tone or other sound, a vibration, etc.

Guidance prompts 228 may include instructions for the user to manipulate system 200 into a configuration that may take images satisfying requirements 234. For example, the instructions may include an instruction to adjust a camera view of the camera to include a particular body part in the camera view, such as moving the camera closer or farther, pan/tilt/zoom the camera, change an angle, tracking or otherwise moving the camera, etc. The instructions may include an instruction to insert or remove a particular appliance. The instructions may also include an instruction to move a particular body part, such as open or close the patient's bite, open the patient's jaw wider, etc. The instruction may include an instruction to adjust one or more camera settings, such as zoom, focus, turn on/off a flash, etc.

When the system determines that the data stream includes the clinically relevant view the system may automatically capture the image or may instruct the user to provide input to capture the image. This process may repeat for each of the medically relevant views.

After capturing the clinically relevant views the process may proceed to block 2130. At block 2130 orthodontic treatment guidance or intervention may be provided. The guidance or intervention may be provided as discussed herein with respect to FIGS. 13-18 in the "Guidance Generation" and "Photo Based Treatment Refinement" sections. For example, a guidance generation module 1304 may receive guidance and apply the received guidance to the patient's current dental occlusion based on measurement data 1322 and the treatment plan data 1514. As discussed herein, the guidance may include guidance related to the timing of switching aligners for example guidance to where the dental liner for an additional amount of time before changing to the aligner for the next stage of treatment or to change to the next stage at an earlier time based on thresholds as discussed above. The guidance may also include instructions to switch from wearing an aligner to a wearing retainer. Other interventions are guidance may include instructions on how to use and when to use chewies, when to schedule a orthodontic follow-up appointment, and other guidance. In some embodiments, for example in which treatment plans include the use of attachments, the guidance generation module may generate guidance to the patient or the doctor based on the absence or detachment of an attachment.

The guidance may be transmitted to one or more of the patient and the doctor or later revision to the patient. For example, the guidance may be sent via text message, email, smart phone or browser-based application notifications, automated telephone calls, calendar invites, or other forms of messaging and communication. In some embodiments the guidance may include both text and audiovisual information, such as a video or image showing the proper use of a chewie.

Intervention may include revisions to the treatment plan. For example, if it is determined that the patient's orthodontic treatment is off track to a sufficient degree that a new treatment plan should be developed, then the clinically relevant images may be used to generate a three-dimensional model of the patient's current dentition. The current dentition may then be used to develop an updated treatment plan for moving the teeth from their current position towards a position. For example, as shown and described with respect to FIGS. 16 and 17, herein.

Virtual Care—Aligner Fit

As described herein, using tele-orthodontics or a virtual care system, patients may take their own photographs of their own dentition and send these photographs to their doctor. The doctor may then assess patients' progress toward treatment goals. As described herein, the doctor may assess patients' actual dentitions via photographs and the virtual care system. However, patients and doctors may wish to use tele-orthodontics for assessing orthodontic appliances, such as assessing "aligner fit" for assessing the quality of seating of an aligner on the patient's dentition.

When using a clear aligner for a patient's treatment, aspects of aligner fit may be visible from photographs taken by the patient. As described further herein, the present disclosure provides systems and methods for remote assessment of the quality of seating for clear aligners.

Figure 24:
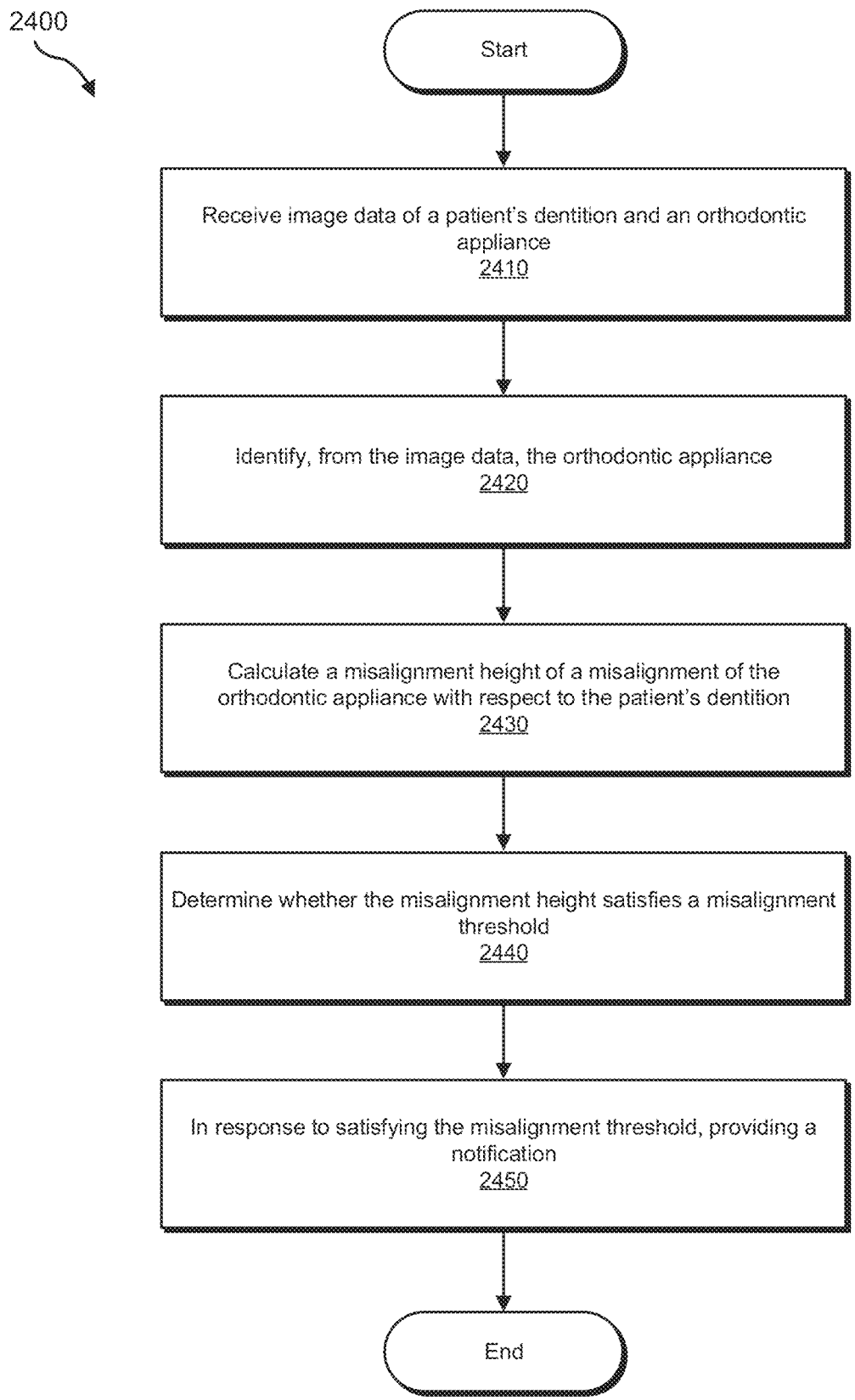
FIG. 24 shows a method of assessing the quality of seating for clear aligners, in accordance with some embodiments.

FIG. 24 is a flow diagram of an exemplary computer-implemented method 2400 for assessing the quality of seating for clear aligners. The steps shown in FIG. 24 may be performed by any suitable computer-executable code and/or computing system, including the systems illustrated in FIGS. 1A, 1B, 1C, 1D, 1E, 2, 3, 4, 6, 13, 15, 16, 19, and 20. In one example, each of the steps shown in FIG. 24 may represent an algorithm whose structure includes and/or is represented by multiple sub-steps, examples of which will be provided in greater detail below.

As illustrated in FIG. 24, at step 2410 one or more of the systems described herein may receive image data of a patient's dentition and an orthodontic appliance. For example, example system 200 in FIG. 2, system 600 in FIG. 6, system 1300 in FIG. 13, or system 1600 in FIG. 16 may receives image data, similar to image data stream 222, image data 232, 2D images 624, etc., of the patient's dentition. As described herein, the patient may take their own photographs of their own dentition using their own devices (e.g., using dental consumer/patient system 102. This image data may include image data captured with the patient wearing their orthodontic appliance, which may be a clear aligner. The patient may capture the image data during a middle or near an end of a treatment stage, although the patient may capture the image data at any time.

The systems described herein may perform step 2410 in a variety of ways. In one example, the image data may be uploaded from a patient's device to another computing device, such as a server or other computer (e.g., virtual dental care system 106 and/or dental professional system 150) for further processing. In other examples, the image data may be processed on the patient's device.

Figure 25A:
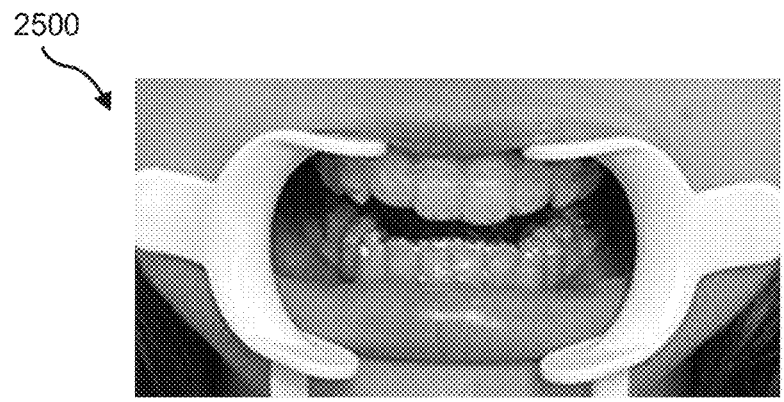
FIG. 25A shows example image data of a patient's dentition with a clear aligner, in accordance with some embodiments.

FIG. 25A illustrates image data 2500 of a patient's dentition including an orthodontic appliance.

At step 2420 one or more of the systems described herein may identify, from the image data, the orthodontic appliance. For example, example system 200 in FIG. 2, system 600 in FIG. 6, system 1300 in FIG. 13, or system 1600 in FIG. 16 may identify the orthodontic appliance, which may be a clear aligner.

The systems described herein may perform step 2420 in a variety of ways. In one example, semantic segmentation may be performed to classify each pixel of the image data into one of a plurality of classes. For example, a probability of belonging to each class may be determined for each pixel of the image data. Each pixel may be classified based on which class the pixel has the highest probability of matching. The classes may include, for example, a tooth class indicating the patient's teeth (which may be portions of the teeth not covered by the orthodontic appliance), a gap class indicating a gap between the orthodontic appliance and a corresponding gingival edge, and a space class indicating a space between an incisal edge of the orthodontic appliance and an incisal edge of a corresponding tooth. In other examples, other classes may be used, such as a gum class corresponding to the patient's gums, an appliance class, other classes, etc. By performing the semantic segmentation, pixels corresponding to the orthodontic appliance (e.g., the gap class and the space class) may be distinguished from pixels corresponding to the patient's dentition without the appliance (e.g., the tooth class). As will be described further below, the gap class and/or the space class may also correspond to a misalignment.

Figure 25B:
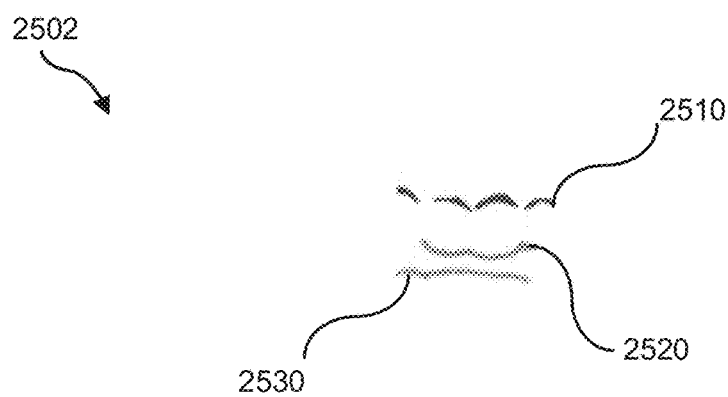
FIG. 25B shows example mask data derived from the image data of FIG. 25A, in accordance with some embodiments.
Figure 25C:
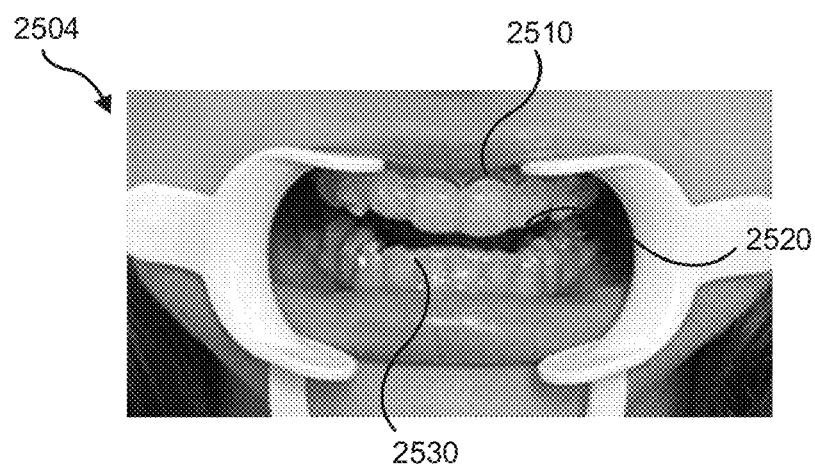
FIG. 25C shows the mask data of FIG. 25B overlaid onto the image data of FIG. 25A, in accordance with some embodiments.

FIG. 25B illustrates mask data 2502 in which semantic segmentation has identified a gap region 2510, a space region 2520, and a space region 2530. FIG. 25C illustrates image data 2504 in which mask data 2502 is overlaid onto image data 2500 to better show how semantic segmentation may produce mask data 2502.

In some examples, the semantic segmentation may be performed using machine learning. For example, neural network 406 or other machine learning scheme may be used to perform the semantic segmentation. In some example, neural network 406 may be trained to perform the semantic segmentation by inputting an image data set, such as a training data set, for semantic segmentation by the neural network. This training data set may have a corresponding mask data set of the desired semantic segmentation. The training may further include computing an error between an output of the neural network (e.g. by performing the semantic segmentation) and the mask data set corresponding to the image data set, and adjusting the parameters of neural network 406 to reduce the error.

In other examples, identifying the orthodontic appliance may include evaluating a color value of each pixel to identify a tooth portion without the orthodontic appliance and a tooth portion with the orthodontic appliance. For instance, a threshold-based segmentation may be used in which color thresholds corresponding to teeth, gums, appliances over teeth, and appliances without teeth, may be used to classify each pixel.

In other examples, identifying the orthodontic appliance may include applying one or more filters to the image data to determine a tooth edge and an orthodontic appliance edge. For instance, an edge-based segmentation may be used to find edges and regions inside the edges may be designated by class based on color features, such as the color threshold described herein.

In some examples, the various segmentation schemes described herein may be applied per tooth such that different segmentation schemes may be applied to different identified teeth. By identifying tooth-to-tooth boundaries, each tooth may be analyzed to provide tooth-specific information or data. For example, color evaluation may be applied per tooth such that color values and/or thresholds may be local to each tooth. Differences in lighting and/or actual differences between tooth colors may affect global color values whereas local tooth color analysis may more readily identify between classes. In another example, semantic segmentation may be applied to identify spaces per tooth. The semantic segmentation scheme may use a semantic segmentation model to find spacing for a given tooth, such as upper-left central incisor, etc. Alternatively, each tooth may be identified in the image data and identified tooth spacing may be associated to the corresponding specific tooth.

At step 2430 one or more of the systems described herein may calculate a misalignment height of a misalignment of the orthodontic appliance with respect to the patient's dentition. For example, example system 200 in FIG. 2, system 600 in FIG. 6, system 1300 in FIG. 13, or system 1600 in FIG. 16 may calculate the misalignment height of a misalignment determined using the identified orthodontic appliance.

The systems described herein may perform step 2430 in a variety of ways. In one example, the misalignment height may be calculated from a pixel height of the misalignment, which may be identified from misalignment classes such as the gap class and/or the space class as described herein. For instance, in FIGS. 25B and/or 25C, the pixel heights of gap region 2510, space region 2520, and space region 2530 may be calculated.

As seen in FIGS. 25B and 25C, each misalignment may occur in several regions, such as across a horizontal range. In such examples, the misalignment dimension (e.g., height, length, and/or width) may be calculated from aggregating the plurality of identified misalignments. For example, for space region 2530, the various heights across space region 2530 may be determined. The misalignment height for space region 2530 may be calculated using, for example, an 80th percentile value of the various heights, although in other examples, other percentiles may be used such that outlier values may not significantly impact the misalignment height. Alternatively, other aggregating functions, such as average, mode, etc. may be used. The misalignment height for gap region 2510 and space region 2520 may be similarly calculated.

Although pixel heights may be used, in some examples, the pixel height may be converted to a standard unit of measurement. For instance, the patient's doctor may prefer to see misalignment heights measured in millimeters or other unit of measurement. To convert the pixel measurement, a reference object, which may be an identifiable subset of teeth such as an incisor, may be identified from the image data. The reference object may be selected based on having an available known measurement. For example, the incisor measurement may be obtained from a treatment plan for the patient. A pixel height of the incisor may be determined from the image data (for example by determining edges for the identified incisor and counting pixels along a desired dimension) and used with the incisor measurement to determine a conversion factor between pixels and the standard unit of measurement (e.g., mm). The misalignment height may be converted from pixels to the standard unit of measurement using the conversion factor.

In some other examples, the conversion factor may be determined using a global average of pixels-per-tooth of all identified teeth, optionally excluding outlier values. In yet other examples, the conversion factor may be determined by constructing a field of pixel-to-mm sizes over an entirety of the image data and interpolating and/or extrapolating pixel-to-mm sizes across the identified arch.

In some examples, the misalignment height may be further adjusted. The semantic segmentation may overestimate misalignment regions. In such instances, a thickness offset may be subtracted from the calculated misalignment height to simulate a material thickness of the orthodontic appliance. The thickness offset may be obtained from a treatment plan for the patient.

In some examples, the misalignment height may be tracked over time using image data over time. For example, the patient may capture image data at various points in time during a treatment stage. A misalignment trend may be identified from the tracked misalignment heights. The misalignment trend may be defined as a general trend (e.g., increasing, decreasing, etc.), as height deltas (e.g., the changes in misalignment height at each point in time), or by actual misalignment height values.

At step 2440 one or more of the systems described herein may determine whether the misalignment height satisfies a misalignment threshold. For example, example system 200 in FIG. 2, system 600 in FIG. 6, system 1300 in FIG. 13, or system 1600 in FIG. 16 may determine whether the misalignment height satisfies a misalignment threshold. The misalignment threshold may be predetermined or precalculated, such as based on patient history and/or other empirical data, or may be manually selected, such as by the patient's doctor.

The systems described herein may perform step 2440 in a variety of ways. In one example, the misalignment threshold may comprise a plurality of misalignment thresholds. For example, 0.5 mm space may not be desirable but may not necessarily require corrective action and therefore may be set as a low threshold. However, 0.75 mm may require corrective action and thus be set as a high threshold. In some examples, if the misalignment trend is tracked, the misalignment threshold may include a misalignment trend threshold. For example, if the misalignment height remains at 0.75 mm at multiple points of time, corrective action may be needed.

At step 2450 one or more of the systems described herein may, in response to satisfying the misalignment threshold, provide a notification. For example, example system 200 in FIG. 2, system 600 in FIG. 6, system 1300 in FIG. 13, or system 1600 in FIG. 16 may provide a notification if the misalignment threshold is satisfied.

The systems described herein may perform step 2450 in a variety of ways. In one example, the notification may include a message or other notification to the patient's doctor. In some examples, the notification may include providing a visual overlay of the misalignment, as in FIG. 25C. In some examples, a color may indicate a type of misalignment.

In some examples, if the misalignment threshold includes a plurality of misalignment thresholds, the notification may include increasing priority based on the threshold met. For each range between the multiple thresholds, a different color may be used when depicting mask data. For example, if the misalignment height is below a low threshold, a low priority color such as blue may be used. If between the low and high threshold, a low warning color such as yellow may be used. If exceeding the high threshold, a high warning color such as orange may be used.

In some examples, the misalignment threshold may include the misalignment trend threshold. The notification may be provided in response to satisfying the misalignment trend threshold.

The virtual care system described herein may allow the patient's doctor to remotely monitor aspects of the patient's treatment progression. Such monitoring may allow early intervention when needed. For example, in response to the notification, the doctor may recommend certain actions or changes in treatment, such as repeating a particular stage, using chewable object (e.g., "chewies") to help the patient chew the orthodontic appliance into place, restart treatment, etc.

While the foregoing disclosure sets forth various embodiments using specific block diagrams, flowcharts, and examples, each block diagram component, flowchart step, operation, and/or component described and/or illustrated herein may be implemented, individually and/or collectively, using a wide range of hardware, software, or firmware (or any combination thereof) configurations. In addition, any disclosure of components contained within other components should be considered example in nature since many other architectures can be implemented to achieve the same functionality.

In some examples, all or a portion of example system 100 in FIG. 1A may represent portions of a cloud-computing or network-based environment. Cloud-computing environments may provide various services and applications via the Internet. These cloud-based services (e.g., software as a service, platform as a service, infrastructure as a service, etc.) may be accessible through a web browser or other remote interface. Various functions described herein may be provided through a remote desktop environment or any other cloud-based computing environment.

In various embodiments, all or a portion of example system 100 in FIG. 1A may facilitate multi-tenancy within a cloud-based computing environment. In other words, the software modules described herein may configure a computing system (e.g., a server) to facilitate multi-tenancy for one or more of the functions described herein. For example, one or more of the software modules described herein may program a server to enable two or more clients (e.g., customers) to share an application that is running on the server. A server programmed in this manner may share an application, operating system, processing system, and/or storage system among multiple customers (i.e., tenants). One or more of the modules described herein may also partition data and/or configuration information of a multi-tenant application for each customer such that one customer cannot access data and/or configuration information of another customer.

According to various embodiments, all or a portion of example system 100 in FIG. 1A may be implemented within a virtual environment. For example, the modules and/or data described herein may reside and/or execute within a virtual machine. As used herein, the term "virtual machine" generally refers to any operating system environment that is abstracted from computing hardware by a virtual machine manager (e.g., a hypervisor). Additionally or alternatively, the modules and/or data described herein may reside and/or execute within a virtualization layer. As used herein, the term "virtualization layer" generally refers to any data layer and/or application layer that overlays and/or is abstracted from an operating system environment. A virtualization layer may be managed by a software virtualization solution (e.g., a file system filter) that presents the virtualization layer as though it were part of an underlying base operating system. For example, a software virtualization solution may redirect calls that are initially directed to locations within a base file system and/or registry to locations within a virtualization layer.

In some examples, all or a portion of example system 100 in FIG. 1A may represent portions of a mobile computing environment. Mobile computing environments may be implemented by a wide range of mobile computing devices, including mobile phones, tablet computers, e-book readers, personal digital assistants, wearable computing devices (e.g., computing devices with a head-mounted display, smartwatches, etc.), and the like. In some examples, mobile computing environments may have one or more distinct features, including, for example, reliance on battery power, presenting only one foreground application at any given time, remote management features, touchscreen features, location and movement data (e.g., provided by Global Positioning Systems, gyroscopes, accelerometers, etc.), restricted platforms that restrict modifications to system-level configurations and/or that limit the ability of third-party software to inspect the behavior of other applications, controls to restrict the installation of applications (e.g., to only originate from approved application stores), etc. Various functions described herein may be provided for a mobile computing environment and/or may interact with a mobile computing environment.

In addition, all or a portion of example system 100 in FIG. 1A may represent portions of, interact with, consume data produced by, and/or produce data consumed by one or more systems for information management. As used herein, the term "information management" may refer to the protection, organization, and/or storage of data. Examples of systems for information management may include, without limitation, storage systems, backup systems, archival systems, replication systems, high availability systems, data search systems, virtualization systems, and the like.

In some embodiments, all or a portion of example system 100 in FIG. 1A may represent portions of, produce data protected by, and/or communicate with one or more systems for information security. As used herein, the term "information security" may refer to the control of access to protected data. Examples of systems for information security may include, without limitation, systems providing managed security services, data loss prevention systems, identity authentication systems, access control systems, encryption systems, policy compliance systems, intrusion detection and prevention systems, electronic discovery systems, and the like.

The process parameters and sequence of steps described and/or illustrated herein are given by way of example only and can be varied as desired. For example, while the steps illustrated and/or described herein may be shown or discussed in a particular order, these steps do not necessarily need to be performed in the order illustrated or discussed. The various example methods described and/or illustrated herein may also omit one or more of the steps described or illustrated herein or include additional steps in addition to those disclosed.

While various embodiments have been described and/or illustrated herein in the context of fully functional computing systems, one or more of these example embodiments may be distributed as a program product in a variety of forms, regardless of the particular type of computer-readable media used to actually carry out the distribution. The embodiments disclosed herein may also be implemented using software modules that perform certain tasks. These software modules may include script, batch, or other executable files that may be stored on a computer-readable storage medium or in a computing system. In some embodiments, these software modules may configure a computing system to perform one or more of the example embodiments disclosed herein.

As described herein, the computing devices and systems described and/or illustrated herein broadly represent any type or form of computing device or system capable of executing computer-readable instructions, such as those contained within the modules described herein. In their most basic configuration, these computing device(s) may each comprise at least one memory device and at least one physical processor.

The term "memory" or "memory device," as used herein, generally represents any type or form of volatile or non-volatile storage device or medium capable of storing data and/or computer-readable instructions. In one example, a memory device may store, load, and/or maintain one or more of the modules described herein. Examples of memory devices comprise, without limitation, Random Access Memory (RAM), Read Only Memory (ROM), flash memory, Hard Disk Drives (HDDs), Solid-State Drives (SSDs), optical disk drives, caches, variations or combinations of one or more of the same, or any other suitable storage memory.

In addition, the term "processor" or "physical processor," as used herein, generally refers to any type or form of hardware-implemented processing unit capable of interpreting and/or executing computer-readable instructions. In one example, a physical processor may access and/or modify one or more modules stored in the above-described memory device. Examples of physical processors comprise, without limitation, microprocessors, microcontrollers, Central Processing Units (CPUs), Field-Programmable Gate Arrays (FPGAs) that implement softcore processors, Application-Specific Integrated Circuits (ASICs), portions of one or more of the same, variations or combinations of one or more of the same, or any other suitable physical processor.

Although illustrated as separate elements, the method steps described and/or illustrated herein may represent portions of a single application. In addition, in some embodiments one or more of these steps may represent or correspond to one or more software applications or programs that, when executed by a computing device, may cause the computing device to perform one or more tasks, such as the method step.

In addition, one or more of the devices described herein may transform data, physical devices, and/or representations of physical devices from one form to another. Additionally or alternatively, one or more of the modules recited herein may transform a processor, volatile memory, non-volatile memory, and/or any other portion of a physical computing device from one form of computing device to another form of computing device by executing on the computing device, storing data on the computing device, and/or otherwise interacting with the computing device.

The term "computer-readable medium," as used herein, generally refers to any form of device, carrier, or medium capable of storing or carrying computer-readable instructions. Examples of computer-readable media comprise, without limitation, transmission-type media, such as carrier waves, and non-transitory-type media, such as magnetic-storage media (e.g., hard disk drives, tape drives, and floppy disks), optical-storage media (e.g., Compact Disks (CDs), Digital Video Disks (DVDs), and BLU-RAY disks), electronic-storage media (e.g., solid-state drives and flash media), and other distribution systems.

A person of ordinary skill in the art will recognize that any process or method disclosed herein can be modified in many ways. The process parameters and sequence of the steps described and/or illustrated herein are given by way of example only and can be varied as desired. For example, while the steps illustrated and/or described herein may be shown or discussed in a particular order, these steps do not necessarily need to be performed in the order illustrated or discussed.

The various exemplary methods described and/or illustrated herein may also omit one or more of the steps described or illustrated herein or comprise additional steps in addition to those disclosed. Further, a step of any method as disclosed herein can be combined with any one or more steps of any other method as disclosed herein.

The processor as described herein can be configured to perform one or more steps of any method disclosed herein. Alternatively or in combination, the processor can be configured to combine one or more steps of one or more methods as disclosed herein.

Unless otherwise noted, the terms "connected to" and "coupled to" (and their derivatives), as used in the specification and claims, are to be construed as permitting both direct and indirect (i.e., via other elements or components) connection. In addition, the terms "a" or "an," as used in the specification and claims, are to be construed as meaning "at least one of." Finally, for ease of use, the terms "including" and "having" (and their derivatives), as used in the specification and claims, are interchangeable with and shall have the same meaning as the word "comprising.

The processor as disclosed herein can be configured with instructions to perform any one or more steps of any method as disclosed herein.

It will be understood that although the terms "first," "second," "third", etc. may be used herein to describe various layers, elements, components, regions or sections without referring to any particular order or sequence of events. These terms are merely used to distinguish one layer, element, component, region or section from another layer, element, component, region or section. A first layer, element, component, region or section as described herein could be referred to as a second layer, element, component, region or section without departing from the teachings of the present disclosure.

As used herein, the term "or" is used inclusively to refer items in the alternative and in combination.

As used herein, characters such as numerals refer to like elements.

The present disclosure includes the following numbered clauses.

Clause 1. A method for dental treatment comprising: receiving one or more photo parameters to define clinically acceptable criteria for a plurality of clinically relevant photos of a person's dentition, the clinically acceptable criteria including at least a plurality of clinically acceptable positions and a plurality of clinically acceptable orientations of teeth relative to a camera; gathering a plurality of image-capture rules to capture the plurality of clinically relevant photos, the plurality of image capture rules being based on the one or more photo parameters; providing first automated instructions to capture the plurality of clinically relevant photos of the person's dentition using the plurality of image-capture rules; capturing the plurality of clinically relevant photos with the camera in response to the first automated instructions.

Clause 2. The method of clause 1, wherein capturing the plurality of clinically relevant photos comprises receiving instructions from the person to capture the plurality of clinically relevant photos in response to the first automated instructions.

Clause 3. The method of clause 1, wherein capturing the plurality of clinically relevant photos comprises processing second automated instructions to the camera to capture the plurality of clinically relevant photos in response to the first automated instructions.

Clause 4. The method of clause 1, wherein the first automated instructions comprise instructions to modify a distance of the camera relative to the person's teeth.

Clause 5. The method of clause 1, wherein the first automated instructions comprise instructions to modify an orientation of the camera relative to the person's teeth.

Clause 6. The method of clause 1, wherein the first automated instructions comprise instructions to capture an anterior view, a left buccal view, a right buccal view, or some combination thereof, of the person's teeth.

Clause 7. The method of clause 1, wherein the first automated instructions comprise instructions to accommodate a bite state of the patient's teeth.

Clause 8. The method of clause 1, wherein the first automated instructions comprise instructions to accommodate a dental appliance on the patient's teeth.

Clause 9. The method of clause 1, wherein the first automated instructions comprise instructions to accommodate a dental appliance on the patient's teeth, wherein the dental appliance comprises a cheek retractor.

Clause 10. The method of clause 1, wherein the first automated instructions comprise instructions to accommodate a dental appliance on the patient's teeth, wherein the dental appliance comprises one or more aligners.

Clause 11. The method of clause 1, wherein the first automated instructions comprise instructions to modify one or more photo settings on the camera.

Clause 12. The method of clause 1, further displaying to the person clinically relevant guidance based on the first automated instructions.

Clause 13. The method of clause 1, further displaying to the person clinically relevant guidance based on the first automated instructions, wherein the clinically relevant guidance comprises an overlay over a representation of the person's teeth.

Clause 14. The method of clause 1, further displaying to the person clinically relevant guidance based on the first automated instructions, wherein the clinically relevant guidance comprises verbal instructions to modify a location of the camera, an orientation of the camera, or some combination thereof.

Clause 15. The method of clause 1, further comprising deriving the plurality of image-capture rules using the one or more photo parameters.

Clause 16. The method of clause 1, further comprising: training a neural network to identify the image-capture rules using the one or more photo parameters on a training dataset of training images; storing the image capture-rules in a datastore.

Clause 17. The method of clause 1, further comprising using the plurality of clinically relevant photos for virtual dental care on the person.

Clause 18. The method of clause 1, further comprising gathering the one or more photo parameters.

Clause 19. The method of clause 1, wherein the method is executed on a mobile device.

Clause 20. The method of clause 1, wherein the plurality of clinically relevant photos do not comprise a three-dimensional (3D) mesh of the patient's teeth.

Clause 21. The method of clause 1, wherein the plurality of clinically relevant photos do not comprise height-map data.

Clause 22. A system comprising: one or more processors; memory storing computer program instructions that, when executed by the one or more processors, cause the system to execute a computer-implemented method comprising: receiving one or more photo parameters to define clinically acceptable criteria for a plurality of clinically relevant photos of a person's dentition, the clinically acceptable criteria including at least a plurality of clinically acceptable positions and a plurality of clinically acceptable orientations of teeth relative to a camera; gathering a plurality of image-capture rules to capture the plurality of clinically relevant photos, the plurality of image capture rules being based on the one or more photo parameters; providing first automated instructions to capture the plurality of clinically relevant photos of the person's dentition using the plurality of image-capture rules; capturing the plurality of clinically relevant photos with the camera in response to the first automated instructions.

Clause 23 The system of clause 22, wherein the system comprises a mobile device.

Clause 24. The system of clause 22, wherein the memory storing computer program instructions that, when executed by the one or more processors, further cause the system to execute a computer-implemented method comprising any of the clauses 1-21.

Clause 25. A non-transitory computer-readable medium comprising one or more computer-executable instructions that, when executed by at least one processor of a computing device, cause the computing device to: perform any of the methods of clauses 1-21.

Clause 26. A method for dental treatment comprising: receiving photos of a person's dentition; identifying a stage of a treatment plan administered to the person's dentition; gathering a three-dimensional (3D) model of the person's dentition corresponding to the stage of the treatment plan; projecting attributes of the 3D model of the person's dentition onto an image plane to get a projected representation of the person's dentition at the stage of the treatment plan; comparing the photos to the projected representation to derive an error image representing the comparison; analyzing the error image for discrepancies, wherein the discrepancies represent one or more deviations of the person's dentition from the stage of the treatment plan.

Clause 27. The method of clause 26, wherein the deviations comprise one or more pixel differences per tooth of the person's dentition.

Clause 28. The method of clause 26, wherein: the deviations comprise one or more pixel differences per tooth of the person's dentition.

Clause 29. The method of clause 27, further comprising: approximating real-world distances between one or more of the discrepancies based on the one or more pixel differences per tooth.

Clause 30. The method of clause 26, further comprising displaying a digital assessment corresponding to one or more of the deviations.

Clause 31. The method of clause 26, wherein the method further comprises: displaying a digital assessment corresponding to one or more of the deviations; receiving one or more instructions to interact with the digital assessment; and modifying the display of the digital assessment using the instructions to interact with the digital assessment.

Clause 32. The method of clause 26, wherein: the method further comprises displaying one or more annotated photos of the person's dentition; and the one or more annotated photos comprise or more overlays showing the one or more of the deviations relative to the photos of the person's dentition.

Clause 33. The method of clause 26, wherein: the method further comprises displaying one or more annotated photos of the person's dentition; the one or more annotated photos comprise or more overlays showing the one or more of the deviations relative to the photos of the person's dentition; the method further comprises receiving one or more instructions to interact with the one or more annotated photos; and the method further comprises modifying a display of the one or more annotated photos in response to the one or more instructions to interact with the one or more annotated photos.

Clause 34. The method of clause 26, wherein the method further comprises: displaying the 3D model of the person's dentition; and displaying, simultaneously with the 3D model, a digital assessment corresponding to one or more of the deviations over the photos of the person's dentition.

Clause 35. The method of clause 26, wherein the method further comprises: displaying the 3D model of the person's dentition; and displaying, simultaneously with the 3D model, one or more annotated photos of the person's dentition, wherein the one or more annotated photos comprise or more overlays showing the one or more of the deviations relative to the photos of the person's dentition.

Clause 36. The method of clause 26, wherein the method further comprises: displaying the 3D model of the person's dentition; displaying, simultaneously with the 3D model, one or more annotated photos of the person's dentition, wherein the one or more annotated photos comprise or more overlays showing the one or more of the deviations relative to the photos of the person's dentition; receiving instructions to interact with the 3D model or the one or more annotated photos of the person's dentition; and modifying a display of the 3D model and the one or more annotated photos while locking the 3D model and the one or more annotated photos to a common orientation.

Clause 37. The method of clause 26, wherein the method further comprises: displaying one or more annotated photos of the person's dentition; and displaying one or more staging elements configured to represent stages of the person's dentition over the course of the treatment plan.

Clause 38. The method of clause 26, wherein: the method further comprises displaying one or more annotated photos of the person's dentition; the method further comprises displaying one or more staging elements configured to represent stages of the person's dentition over the course of the treatment plan; and the one or more staging elements show each jaw of the person's dentition relative to stages of the treatment plan.

Clause 39. The method of clause 26, wherein the method further comprises: displaying a digital assessment corresponding to one or more of the deviations; providing one or more digital diagnosis tools associated with the digital assessment; and receiving a diagnosis from a doctor using the one or more digital diagnosis tools.

Clause 40. The method of clause 26, further comprising: training a neural network to recognize machine-learned differences between projected representations of a first training set of 3D models and a second training set of training images; and using the machine-learned differences to compare the photos to the projected representation of the 3D model.

Clause 41. The method of clause 26, further comprising: providing intelligent guidance to a person to take the photos of the person's dentition; capturing the photos using the intelligent guidance.

Clause 42. The method of clause 26, wherein the photos do not comprise a three-dimensional (3D) mesh of the patient's teeth.

Clause 43. The method of clause 26, wherein the photos do not comprise height-map data.

Clause 44. The method of clause 26, further comprising modifying the treatment plan using the discrepancies.

Clause 45. The method of clause 26, wherein the photos comprise a plurality of photos, each photo of the plurality of photos having a different orientation with respect to the patient's dentition.

Clause 46. The method of clause 26, wherein the photos comprise a plurality of photos, a first photo of the plurality of photos having an anterior orientation, a second photo of the plurality of photos having a right buccal orientation, and a third photo of the plurality of photos having a left buccal orientation.

Clause 47. A system for dental treatment comprising: one or more processors; and memory storing computer program instructions that, when executed by the one or more processors, cause the system to execute a computer-implemented method comprising: receiving photos of a person's dentition; identifying a stage of a treatment plan administered to the person's dentition; gathering a three-dimensional (3D) model of the person's dentition corresponding to the stage of the treatment plan; projecting attributes of the 3D model of the person's dentition onto an image plane to get a projected representation of the person's dentition at the stage of the treatment plan; comparing the photos to the projected representation to derive an error image representing the comparison; and analyzing the error image for discrepancies, wherein the discrepancies represent one or more deviations of the person's dentition from the stage of the treatment plan.

Clause 48. The system of clause 47, wherein the memory storing computer program instructions that, when executed by the one or more processors, further cause the system to execute a computer-implemented method comprising any of the clauses 26-46.

Clause 49. A non-transitory computer-readable medium comprising one or more computer-executable instructions that, when executed by at least one processor of a computing device, cause the computing device to: perform any of the methods of clauses 26-46.

Clause 50. A method for dental treatment comprising: receiving photos of a patient's dentition; gathering treatment parameters for at treatment plan, the treatment parameters representing attributes of the treatment plan selected by a doctor for the patient's dentition of a patient; generating, using the photos and the treatment parameters, one or more intelligent guidance rules to guide application of at least a portion of the treatment parameters to the patient's dentition; generating instructions to apply the intelligent patient guidance rules to the patient's dentition; and providing the instructions to the patient to apply the at least a portion of the treatment plan in accordance with the intelligent patient guidance rules.

Clause 51. The method of clause 50, wherein the treatment parameters comprise doctor-preference parameters that specify treatment protocols the doctor has previously prescribed for a clinical condition.

Clause 52. The method of clause 50, wherein the treatment parameters comprise per-patient parameters that specify treatment protocols specific to the patient.

Clause 53. The method of clause 50, wherein: the method further comprises managing a doctor guidance template with the treatment parameters; and the one or more intelligent guidance rules are generated using the doctor guidance template.

Clause 54. The method of clause 50, wherein: the method further comprises managing a doctor guidance template with the treatment parameters; the doctor guidance template comprises a template configured to track implementation of the treatment plan; and the one or more intelligent guidance rules are generated using the doctor guidance template.

Clause 55. The method of clause 50, further comprising: managing a doctor guidance template with the treatment parameters; receiving modifications instructions to modify the doctor guidance template from the doctor; modifying the doctor guidance template based on the modification instructions.

Clause 56. The method of clause 50, further comprising configuring a display of a computing system to guide the patient to apply the at least a portion of the treatment plan in accordance with the intelligent patient guidance rules.

Clause 57. The method of clause 50, further comprising configuring a display of a computing system to display one or more interactive elements that guide the patient to apply the at least a portion of the treatment plan in accordance with the intelligent patient guidance rules.

Clause 58. The method of clause 50, wherein: the method further comprises configuring a display of a computing system to guide the patient to apply the at least a portion of the treatment plan in accordance with the intelligent patient guidance rules; and the computing system is a dental consumer/patient system associated with the patient.

Clause 59. The method of clause 50, wherein: the method further comprises configuring a display of a computing system to guide the patient to apply the at least a portion of the treatment plan in accordance with the intelligent patient guidance rules; and the computing system is a dental professional system associated with the doctor.

Clause 60. The method of clause 50, further comprising instructing the patient to take a corrective action comprising a modification of the treatment plan.

Clause 61. The method of clause 50, further comprising instructing the patient to manage a dental appliance used to implement the treatment plan.

Clause 62. The method of clause 50, further comprising notifying the doctor to instruct the patient to take a corrective action comprising a modification of the treatment plan.

Clause 63. The method of clause 50, wherein the instructions to apply the at least a portion of the treatment plan comprises one or more of: instructions to change a dental appliance, instructions to keep a dental appliance beyond a time prescribed by the treatment plan, instructions to use a supplemental dental appliance at a particular time or a particular location, instructions to set an appointment for a specific dental condition, instructions to notify the doctor about one or more dental conditions, and instructions to notify a doctor about a specific region of the patient's dentition for a particular aspect of the treatment plan.

Clause 64. The method of clause 50, wherein the treatment plan prescribes aligners to move the patient's teeth from an initial arrangement toward a target arrangement using a plurality of successive tooth-repositioning appliances.

Clause 65. The method of clause 50, further comprising: providing intelligent photo guidance instructions to the patient to capture the photos of the patient's dentition, wherein the photos comprise clinically relevant photos of the patient's dentition; and taking the photos of the patient dentition in accordance with the intelligent photo guidance instructions.

Clause 66. The method of clause 50, further comprising taking the photos of the patient dentition at a mobile device associated with the patient.

Clause 67. The method of clause 50, wherein the photos do not comprise a three-dimensional (3D) mesh of the patient's teeth.

Clause 68. The method of clause 50, wherein the photos do not comprise height-map data.

Clause 69. The method of clause 50, wherein the photos comprise a plurality of photos, each photo of the plurality of photos having a different orientation with respect to the patient's dentition.

Clause 70. The method of clause 50, wherein the photos comprise a plurality of photos, a first photo of the plurality of photos having an anterior orientation, a second photo of the plurality of photos having a right buccal orientation, and a third photo of the plurality of photos having a left buccal orientation.

Clause 71. The method of clause 50, further comprising: training a neural network to recognize the one or more intelligent guidance rules using a set of training photos and a set of training treatment parameters; and storing the one or more intelligent guidance rules in a datastore.

Clause 72. A system for dental treatment comprising: one or more processors; memory storing computer program instructions that, when executed by the one or more processors, cause the system to execute a computer-implemented method comprising: receiving photos of a patient's dentition; gathering treatment parameters for at treatment plan, the treatment parameters representing attributes of the treatment plan selected by a doctor for the patient's dentition of a patient; generate, using the photos and the treatment parameters, one or more intelligent guidance rules to guide application of at least a portion of the treatment parameters to the patient's dentition; generate instructions to apply the intelligent patient guidance rules to the patient's dentition; and provide the instructions to the patient to apply the at least a portion of the treatment plan in accordance with the intelligent patient guidance rules.

Clause 73. The system of clause 72, wherein the memory storing computer program instructions that, when executed by the one or more processors, further cause the system to execute a computer-implemented method comprising any of the clauses 50-71.

Clause 74. A non-transitory computer-readable medium comprising one or more computer-executable instructions that, when executed by at least one processor of a computing device, cause the computing device to: perform any of the methods of clauses 50-71.

Clause 75. A method for dental treatment comprising: receiving photos capturing a state of a patient's dentition of a patient at a specific time; retrieving a first treatment plan to treat the patient's dentition; identifying an intended arrangement of the first treatment plan at the specific time; evaluating the photo parameters of the photos to generate alignment data to align the intended arrangement of the first treatment plan and the photos; generating an alignment mesh using the alignment data, the alignment mesh comprising a three-dimensional (3D) mesh representation of the patient's dentition at the specific time; performing an evaluation of the first treatment plan for modifications using the alignment mesh; and identify proposed modifications to the first treatment plan based on the evaluation.

Clause 76. The method of clause 75, wherein the photo parameters comprise one or more of camera parameters, location parameters, and orientation parameters.

Clause 77. The method of clause 75, wherein evaluating the photo parameters comprises optimizing the photo parameter using a trained neural network.

Clause 78. The method of clause 75, wherein evaluating the photo parameters comprises implementing a differential renderer on the photo parameters.

Clause 79. The method of clause 75, wherein evaluating the photo parameters comprises performing an expectation maximization on the photo parameters.

Clause 80. The method of clause 75, wherein performing the evaluation of the first treatment plan comprises determining where portions of the patient's dentition have deviated from intended positions in the first treatment plan.

Clause 81. The method of clause 75, further comprising displaying one or more annotations representing the proposed modifications to a doctor.

Clause 82. The method of clause 75, further comprising displaying one or more overlays representing the proposed modifications to a doctor.

Clause 83. The method of clause 75, wherein: the method further comprises receiving from a doctor a request for the first treatment plan; the first treatment plan is retrieved in response to the request for the first treatment plan.

Clause 84. The method of clause 75, further comprising: providing the proposed modifications to a doctor; and facilitating review of the proposed modifications by the doctor.

Clause 85. The method of clause 75, further comprising: receiving, from a doctor, reviewed modifications based on the proposed modifications to the first treatment plan; and refining one or more steps of the first treatment plan using the reviewed modifications.

Clause 86. The method of clause 75, further comprising: receiving, from a doctor, reviewed modifications based on the proposed modifications to the first treatment plan; refining one or more steps of the first treatment plan using the reviewed modifications; and sending a refined treatment plan comprising the refined one or more steps to the patient or the doctor.

Clause 87. The method of clause 75, further comprising: receiving, from a doctor, reviewed modifications based on the proposed modifications to the first treatment plan; refining one or more steps of the first treatment plan using the reviewed modifications, wherein the one or more steps comprise placement of attachments, staging of teeth, or time for performing an interproximal reduction procedure.

Clause 88. The method of clause 75, further comprising taking the photos of the patient dentition at a mobile device associated with the patient.

Clause 89. The method of clause 75, wherein the photos do not comprise a three-dimensional (3D) mesh of the patient's teeth.

Clause 90. The method of clause 75, wherein the photos do not comprise height-map data.

Clause 91. The method of clause 75, further comprising: training a neural network to recognize the one or more intelligent guidance rules using a set of training photos and a set of training treatment parameters; and storing the one or more intelligent guidance rules in a datastore.

Clause 92. A system comprising: one or more processors; memory storing computer program instructions that, when executed by the one or more processors, cause the system to execute a computer-implemented method comprising: receiving photos capturing a state of a patient's dentition of a patient at a specific time; retrieving a first treatment plan to treat the patient's dentition; identify an intended arrangement of the first treatment plan at the specific time; evaluating the photo parameters of the photos to generate alignment data to align the intended arrangement of the first treatment plan and the photos; generating an alignment mesh using the alignment data, the alignment mesh comprising a three-dimensional (3D) mesh representation of the patient's dentition at the specific time; performing an evaluation of the first treatment plan for modifications using the alignment mesh; and identifying proposed modifications to the first treatment plan based on the evaluation.

Clause 93. The system of clause 92, wherein the memory storing computer program instructions that, when executed by the one or more processors, further cause the system to execute a computer-implemented method comprising any of the clauses 75-91.

Clause 94. A non-transitory computer-readable medium comprising one or more computer-executable instructions that, when executed by at least one processor of a computing device, cause the computing device to: perform any of the methods of clauses 75-91.

Clause 95. A method for treatment-based photo guidance, the method comprising: receiving a treatment plan; determining the movement of a first one or more teeth based on the movement of tooth models in the treatment plan; and determining one or more photo views for capturing the movement of the first one or more teeth.

Clause 96. The method of clause 95, wherein the treatment plan includes models of the positions of the patient's teeth.

Clause 97. The method of clause 95, determining the movement of a first one or more teeth includes determining the difference between a position of a first tooth in a first stage of a treatment plan and a position of the first tooth in a second stage of the treatment plan.

Clause 98. The method of clause 97, wherein determining the movement includes determining a vertex was movement between the first stage and the second stage.

Clause 99. The method of clause 97, further comprising determining a movement vector based on the difference in position.

Clause 100. The method of clause 99, wherein determining a photo view includes determining a position and orientation that is normal to the movement vector and a field of view that includes the first tooth.

Clause 101. The method of clause 95, wherein determining a photo view includes selecting a photo view from one or more predetermined photo views.

Clause 102. The method of clause 101, wherein the predetermined photo views include a position and orientation for capturing the buccal and occlusal surfaces of each tooth.

Clause 103. The method of clause 102, further comprising consolidating the one or more photo views.

Clause 104. The method of clause 103, wherein consolidating the one or more photo views includes determining that at least two of the one or more photo views are of adjacent teeth and removing one of the at least two photo views from the determined photo views.

Clause 105. The method of clause 95, further comprising receiving an image stream from a camera; and comparing an image in the image stream to the one or more photo views.

Clause 106. The method of clause 105, further comprising determining that the image in the image stream does not match the one or more photo views; and providing guidance to move the camera so that an image in the more closely matches the one or more photo views.

Clause 107. The method of clause 105, further comprising determining that the image in the image stream matches the one or more photo views; and providing guidance capturing image.

Clause 108. The method of clause 107, wherein determining that the image in the image stream matches the one or more photo views includes determining that the field of view the image includes at least a set of teeth in the field of view of the one or more photo views.

Clause 109. The method of clause 107, wherein determining that the image in the image stream matches the one or more photo views is taken and orientation within 10° of the orientation of the one or more photo views.

Clause 110. The method of clause 105, further comprising determining that the image in the image stream matches the one or more photo views; and capturing the image based on the determination that the image in the image stream sufficiently matches the one or more photo views.

Clause 111. The method of clause 95, wherein determining the movement of the first one or more teeth includes determining that the first one or more teeth are moving during the treatment stage.

Clause 112. The method of clause 111, wherein the photo views include one or more buccal views and one or more occlusal views that include the first one or more teeth that are moving during the treatment stage.

Clause 113. The method of clause 112, wherein the one or more buccal views include a buccal view centered along the patient's midline and one or more buccal views 15°, 30°, 45°, 60°, 75°, or 90° offset to the left and right of the patient's midline.

Clause 114. A system comprising: a camera; at least one physical processor; and physical memory comprising computer-executable instructions that, when executed by the physical processor, cause the physical processor to: perform any of the method of clauses 95-113.

Clause 115. A non-transitory computer-readable medium comprising one or more computer-executable instructions that, when executed by at least one processor of a computing device, cause the computing device to: perform any of the methods of clauses 95-113.

Clause 116. A method for photo-based orthodontic treatment, the method comprising: receiving image data of a patient's dentition and an orthodontic appliance; identifying, from the image data, the orthodontic appliance; calculating a misalignment height of a misalignment of the orthodontic appliance with respect to the patient's dentition; determining whether the misalignment height satisfies a misalignment threshold; and in response to satisfying the misalignment threshold, providing a notification.

Clause 117. The method of clause 116, wherein identifying the orthodontic appliance further comprises: performing semantic segmentation to classify each pixel of the image data into one of a plurality of classes.

Clause 118. The method of clause 117, further comprising training a neural network to perform the semantic segmentation by: inputting an image data set for semantic segmentation by the neural network; computing an error between an output of the neural network and a mask data set corresponding to the image data set; and adjusting parameters of the neural network to reduce the error.

Clause 119. The method of clause 117, wherein performing the semantic segmentation further comprises, for each pixel: determining a probability of the pixel matching each of the plurality of classes; and classifying the pixel into the one of the plurality of classes based on a corresponding highest probability value.

Clause 120. The method of clause 117, wherein the plurality of classes includes a tooth class indicating the patient's teeth, a gap class indicating a gap between the orthodontic appliance and a corresponding gingival edge, and a space class indicating a space between an incisal edge of the orthodontic appliance and an incisal edge of a corresponding tooth, and wherein the gap class and the space class correspond to the misalignment.

Clause 121. The method of clause 116, wherein the misalignment height is calculated from a pixel height of the misalignment.

Clause 122. The method of clause 121, wherein calculating the misalignment height further comprises: determining a pixel height of an incisor identified in the image data; obtaining an incisor measurement in a standard unit of measurement; determining, using the pixel height of the incisor and the incisor measurement, a conversion factor between pixels and the standard unit of measurement; and converting, using the conversion factor, the misalignment height from pixels to the standard unit of measurement.

Clause 123. The method of clause 122, wherein the incisor measurement is obtained from a treatment plan for the patient.

Clause 124. The method of clause 122, wherein the standard unit of measurement is millimeters.

Clause 125. The method of clause 116, wherein the misalignment height is calculated from aggregating a plurality of identified misalignments.

Clause 126. The method of clause 125, wherein calculating the misalignment height further comprises determining an 80th percentile of the plurality of identified misalignments.

Clause 127. The method of clause 116, wherein calculating the misalignment height further comprises subtracting a thickness offset to simulate a material thickness of the orthodontic appliance.

Clause 128. The method of clause 127, wherein the thickness offset is obtained from a treatment plan for the patient.

Clause 129. The method of clause 116, further comprising tracking the misalignment height over time using image data over time.

Clause 130. The method of clause 129, further comprising: identifying a misalignment trend from the tracked misalignment height; determining whether the misalignment trend satisfies a misalignment trend threshold; and in response to satisfying the misalignment trend threshold, providing a notification.

Clause 131. The method of clause 116, further comprising providing a visual overlay of the misalignment.

Clause 132. The method of clause 116, wherein the misalignment threshold comprises a plurality of misalignment thresholds.

Clause 133. The method of clause 132, further comprising providing a visual overlay of the misalignment, wherein each range between each of the plurality of misalignment thresholds corresponds to a unique color.

Clause 134. The method of clause 116, wherein identifying the orthodontic appliance further comprises: applying one or more filters to the image data to determine a tooth edge and an orthodontic appliance edge.

Clause 135. The method of clause 116, wherein identifying the orthodontic appliance further comprises: evaluating a color value of each pixel to identify a tooth portion without the orthodontic appliance and a tooth portion with the orthodontic appliance.

Clause 136. A system comprising: a camera; at least one physical processor; and physical memory comprising computer-executable instructions that, when executed by the physical processor, cause the physical processor to: perform any of the method of clauses 116-135.

Clause 137. A non-transitory computer-readable medium comprising one or more computer-executable instructions that, when executed by at least one processor of a computing device, cause the computing device to: perform any of the methods of clauses 116-135.

Clause 138. A method for capturing image data of a body part according to clinical requirements, the method comprising: receiving an image data stream from a camera; determining, using an artificial intelligence scheme, one or more binary classifications and one or more categorical classifications from the image data stream; comparing the one or more binary classifications and the one or more categorical classifications to a set of requirements; and providing feedback based on the comparison.

Clause 139. The method of clause 138, wherein the one or more binary classifications comprise at least one of: whether a particular tooth is visible; whether an upper jaw is visible; whether a lower jaw is visible; whether an appliance is visible; whether a focal distance threshold, corresponding to whether an entirety of the body part is visible, is satisfied; whether upper and lower teeth contact; whether a lighting threshold is satisfied; whether a localized calculus is present; and whether a gingiva recession is present.

Clause 140. The method of clause 138, wherein the one or more binary classifications are determined using binary cross-entropy.

Clause 141. The method of clause 138, wherein the one or more categorical classifications comprise at least one of: anterior view; left buccal view; and right buccal view.

Clause 142. The method of clause 138, wherein the one or more categorical classifications comprise one or more sets of mutually exclusive categories.

Clause 143. The method of clause 138, wherein the feedback includes a guidance prompt when at least one of the set of requirements is not satisfied.

Clause 144. The method of clause 143, wherein the guidance prompt includes at least one of: an instruction to adjust a camera view of the camera to include a particular body part in the camera view; an instruction to insert a particular appliance; an instruction to remove a particular appliance; an instruction to move a particular body part; and an instruction to adjust one or more camera settings.

Clause 145. The method of clause 143, wherein the guidance prompt includes a visual prompt.

Clause 146. The method of clause 143, wherein the guidance prompt includes an audible prompt.

Clause 147. The method of clause 143, wherein the guidance prompt includes a haptic prompt.

Clause 148. The method of clause 138, wherein the feedback includes automatically adjusting one or more camera settings when at least one of the set of requirements is not satisfied.

Clause 149. The method of clause 138, wherein the feedback includes automatically capturing image data of the body part when the set of requirements is satisfied.

Clause 150. The method of clause 138, wherein the feedback includes preventing capture of image data of the body part when at least one of the set of requirements is not satisfied.

Clause 151. The method of clause 138, wherein the feedback includes sending a notification.

Clause 152. The method of clause 138, further comprising determining the set of requirements based on a patient dentition and a current state of treatment plan.

Clause 153. The method of clause 152, wherein the set of requirements include at least one of: visibility of a particular body part; visibility of a particular appliance; and type of view captured.

Clause 154. The method of clause 153, wherein the particular body part corresponds to a tooth of interest identified from the current state of treatment plan.

Clause 155. The method of clause 154, wherein the particular body part further corresponds to one or more teeth near the tooth of interest.

Clause 156. A system comprising: a camera; at least one physical processor; and physical memory comprising computer-executable instructions that, when executed by the physical processor, cause the physical processor to: perform any of the methods of clauses 138-155.

Clause 157. A non-transitory computer-readable medium comprising one or more computer-executable instructions that, when executed by at least one processor of a computing device, cause the computing device to: perform any of the methods of clauses 138-155.

Clause 158. A method for determining deviations of teeth from a captured image data of dentition, the method comprising: receiving one or more two-dimensional images of a patient's teeth; receiving a three-dimensional model of a patient's teeth; registering the patient's teeth in the three-dimensional model to the patient's teeth in the one or more two-dimensional images; projecting the registered teeth in the three-dimensional model onto each of the one or more two-dimensional images; and generating an error image based on the difference in the positions of the projected teeth of the three-dimensional model and the corresponding teeth of the one or more two-dimensional images.

Clause 159. The method of clause 158, wherein: projecting the registered teeth includes projecting the registered teeth in the three-dimensional model onto the image plane of each of the one or more two-dimensional images.

Clause 160. The method of clause 158, wherein: receiving the two-dimensional image of a patient's teeth includes receiving images of the patient's teeth from a plurality of perspectives.

Clause 161. The method of clause 159, wherein: the plurality of perspectives includes at least two of an upper occlusal perspective, a lower occlusal perspective, an anterior perspective, a right buccal perspective, and a left buccal perspective.

Clause 162. The method of clause 158, wherein: registering the patient's teeth in the three-dimensional model to the patient's teeth in the one or more two-dimensional images includes registering the patient's teeth in the three-dimensional model to the patient's teeth in the plurality of perspectives in the one or more two-dimensional images.

Clause 163. The method of clause 158, wherein: receiving one or more two-dimensional images of a patient's teeth comprises capturing the one or more image of the patient's teeth with a camera.

Clause 164. The method of clause 158, further comprising: generating an error image based on the projection, the error image including data representative of the difference between a position of a tooth in the three-dimensional model and a position of the tooth in the two-dimensional image.

Clause 165. The method of clause 164, wherein the three-dimensional model is a three-dimensional model of the patient's teeth in stage a treatment plan.

Clause 166. The method of clause 165, wherein the two-dimensional image of the patient's teeth corresponds to the patient's treatment being in the stage of the treatment.

Clause 167. The method of clause 164, wherein the error image includes an first edge corresponding to an edge of a first of the patient's teeth in the two-dimensional image from a first perspective and a second edge corresponds to an edge of the projection of the first of the patient's teeth in the three-dimensional image from the first perspective.

Clause 168. The method of clause 164, further comprising: generating an image mask based on the error data.

Clause 169. The method of clause 164, further comprising: applying the image mask to the two-dimensional image.

Clause 170. The method of clause 164, further comprising: adjusting one or more a color and a brightness of the masked portion of the two-dimensional image.

Clause 171. The method of clause 164, wherein the error image includes an outline of the teeth of the projection of the three-dimensional image overlaid onto the two-dimensional image.

Clause 172. The method of clause 164, wherein the error image includes an overlay of the projected three-dimensional model over the two-dimensional image.

Clause 173. The method of clause 167, further comprising: determine a distance between the first edge and the second edge in the error image.

Clause 174. The method of clause 173, wherein: the distance is determined based on the number of pixels spanning the distance between the first edge and the second edge.

Clause 175. The method of clause 174, further comprising: determining a real-world distance based on the number of pixels and a real-world size of the pixels.

Clause 176. A system comprising: a camera; at least one physical processor; and physical memory comprising computer-executable instructions that, when executed by the physical processor, cause the physical processor to: perform any of the methods of clauses 158-175.

Clause 177. A non-transitory computer-readable medium comprising one or more computer-executable instructions that, when executed by at least one processor of a computing device, cause the computing device to: perform any of the methods of clauses 158-175.

Clause 178. A method of generating and providing guidance, the method comprising: receiving patient dentition measurement information; receiving patient treatment plan information; receiving guidance information; generating patient guidance by applying the guidance information based on the measurement information and the treatment plan information.

Clause 179. The method of clause 178, further comprising: deconflicting the guidance information.

Clause 180. The method of clause 179, further comprising: transmitting the guidance information to a patient.

Clause 181. The method of clause 178, wherein the patient dentition measurement information includes a distance between a current position of a tooth and an expected position of the tooth.

Clause 182. The method of clause 181, wherein the expected position of the tooth is based on a position of the tooth accordingly to an orthodontic treatment plan.

Clause 183. The method of clause 181, wherein the distance is determined from a two-dimension image of the patient's teeth in the current position and a three-dimensional model of the patient's teeth in the expected position.

Clause 184. The method of clause 183, wherein the distance is based on a projection of the patient's teeth in the three-dimensional model onto one or more two-dimensional images of the patient's teeth.

Clause 185. The method of clause 178, wherein the guidance information includes a guidance template and case-by-case guidance.

Clause 186. The method of clause 185, wherein deconflicting the guidance information includes removing redundant guidance.

Clause 187. The method of clause 185, wherein deconflicting the guidance information includes removing consolidating two or more pieces of guidance into a single piece of guidance.

Clause 188. The method of clause 178, wherein the guidance includes one or more of modified treatment, a notification, or treatment instructions.

Clause 189. The method of clause 188, wherein modified treatment includes one or more of the use of a chewie, changing to a different dental appliance, and wearing a dental appliance for longer than initial instructed, based on the treatment plan.

Clause 190. The method of clause 178, wherein the guidance information includes, tooth deviation thresholds that when met cause a guidance to be generated.

Clause 191. The method of clause 190, wherein the threshold is based on deviation measured at a single stage of treatment.

Clause 192. The method of clause 190, wherein the threshold is based on deviation measured over multiple stages of treatment.

Clause 193. The method of clause 184, wherein the guidance template includes a set of generic thresholds used by a doctor.

Clause 194. The method of clause 185, wherein the case-by-case guidance includes thresholds specific to a particular treatment.

Clause 195. The method of clause 178, wherein generating patient guidance is based on measurements from previous stages of treatment.

Clause 196. A system comprising: a camera; at least one physical processor; and physical memory comprising computer-executable instructions that, when executed by the physical processor, cause the physical processor to: perform any of the methods of clauses 178-195.

Clause 197. A non-transitory computer-readable medium comprising one or more computer-executable instructions that, when executed by at least one processor of a computing device, cause the computing device to: perform any of the methods of clauses 178-195.

Clause 198. A method for photo-based orthodontic treatment, the method comprising: receiving one or more photos of a patient's dentition; receiving a treatment plan for the patient; determining, based on the treatment plan and the one or more photos, that a current position of the patient's teeth deviate from an expected position of the patient's teeth; and generating an updated treatment plan to move the patient's teeth towards a final position of the patient's teeth, based on the positions of the patient's teeth in the photos.

Clause 199. The method of clause 198, wherein: the position of the current position of the patient's teeth is based on the position of the teeth in the one or more photos.

Clause 200. The method of clause 198, wherein: the expected position of the patient's teeth is based on a position of the patient's teeth in a stage of the treatment plan.

Clause 201. The method of clause 198, wherein: the final position is different than the final position of the patient's teeth is the same as the final position in the treatment plan.

Clause 202. The method of clause 198, wherein: the final position is different than the final position of the patient's teeth is different than the final position in the treatment plan.

Clause 203. The method of clause 198, wherein: the one or more photos are two-dimensional images of the patient's teeth are from one or more perspectives.

Clause 204. The method of clause 198, wherein the measuring includes: determining a distance between a position of the patient's teeth in the one or more photos of the patient's teeth in the current position and a three-dimensional model of the patient's teeth in the expected position.

Clause 205. The method of clause 204, wherein the distance is based on a projection of the patient's teeth in the three-dimensional model onto the one or more photos of the patient's teeth.

Clause 206. The method of clause 198, further comprising: optimizing one or more three-dimensional parameters of the three-dimensional model of the patient's teeth to move the teeth in the three-dimensional model into the current position according to the photos of the patient's teeth.

Clause 207. The method of clause 206, wherein: the three-dimensional model is a segment dental mesh model of the patient's teeth.

Clause 208. The method of clause 206, wherein: the segmented three-dimensional model is a segmented dental mesh model of the patient's teeth is based on an intra-oral three-dimensional scan of the patient's teeth.

Clause 209. The method of clause 208, further comprising: generating an updated segmented segment dental mesh model of the patient's teeth based on the one or more optimized three-dimensional parameters.

Clause 210. The method of clause 208, wherein the generating of an updated treatment plan uses the updated segmented segment dental mesh model as an initial position of the patient's teeth.

Clause 211. The method of clause 210, wherein the updated treatment plan includes a plurality of intermediate tooth position to move the patient's teeth from the initial position towards the final position.

Clause 212. The method of clause 211, further comprising: fabricating a plurality of dental aligners based on the intermediate tooth positions to move the teeth towards the final position.

Clause 213. The method of clause 203, wherein: the one or more perspectives includes one or more of an upper occlusal perspective, a lower occlusal perspective, an anterior perspective, a right buccal perspective, and a left buccal perspective.

Clause 214. The method of clause 204, wherein: generating the updated treatment plan occurs if the distance for one or more teeth is greater than 0.1 mm.

Clause 215. The method of clause 206, wherein: the optimizing includes using one or more of a differential rendering and an expectation-maximization process.

Clause 216. A system comprising: a camera; at least one physical processor; and physical memory comprising computer-executable instructions that, when executed by the physical processor, cause the physical processor to: perform any of the methods of clauses 198-215.

Clause 217. A non-transitory computer-readable medium comprising one or more computer-executable instructions that, when executed by at least one processor of a computing device, cause the computing device to: perform any of the methods of clauses 198-215.

Embodiments of the present disclosure have been shown and described as set forth herein and are provided by way of example only. One of ordinary skill in the art will recognize numerous adaptations, changes, variations and substitutions without departing from the scope of the present disclosure. Several alternatives and combinations of the embodiments disclosed herein may be utilized without departing from the scope of the present disclosure and the inventions disclosed herein. Therefore, the scope of the presently disclosed inventions shall be defined solely by the scope of the appended claims and the equivalents thereof.

What is claimed is:

1. A method of dental treatment comprising:
identifying a stage of a treatment plan administered to a person's dentition;
receiving a two-dimensional photo of the person's dentition corresponding to the stage of the treatment plan;
gathering a three-dimensional (3D) model of the person's dentition corresponding to the stage of the treatment plan;
projecting attributes of the 3D model of the person's dentition onto an image plane to get a projected representation of the person's dentition at the stage of the treatment plan;
comparing a position of one or more teeth of the person's dentition in the two-dimensional photo to the projected representation of the person's dentition to derive a two-dimensional error image representing the comparison; and
analyzing the two-dimensional error image for discrepancies, wherein analyzing includes determining a distance between corresponding edges in the error image, and wherein the discrepancies represent one or more deviations of the person's dentition from the stage of the treatment plan.

2. The method of claim 1, wherein the deviations comprise one or more pixel differences of the person's dentition.

3. The method of claim 1, wherein:
the deviations comprise one or more pixel differences per tooth of the person's dentition.

4. The method of claim 3, further comprising:
approximating real-world distances between one or more of the discrepancies based on the one or more pixel differences per tooth.

5. The method of claim 1, further comprising displaying a digital assessment corresponding to one or more of the deviations.

6. The method of claim 1, wherein the method further comprises:
displaying a digital assessment corresponding to one or more of the deviations;
receiving one or more instructions to interact with the digital assessment; and
modifying the display of the digital assessment using the instructions to interact with the digital assessment.

7. The method of claim 1, wherein:
the method further comprises displaying one or more annotated photos of the person's dentition; and
the one or more annotated photos comprise one or more overlays showing the one or more of the deviations relative to the photos of the person's dentition.

8. The method of claim 1, wherein:
the method further comprises displaying one or more annotated photos of the person's dentition;
the one or more annotated photos comprise or more overlays showing the one or more of the deviations relative to the photos of the person's dentition;
the method further comprises receiving one or more instructions to interact with the one or more annotated photos; and
the method further comprises modifying a display of the one or more annotated photos in response to the one or more instructions to interact with the one or more annotated photos.

9. The method of claim 1, wherein the method further comprises:
displaying the 3D model of the person's dentition; and
displaying, simultaneously with the 3D model, a digital assessment corresponding to one or more of the deviations over the photos of the person's dentition.

10. The method of claim 1, wherein the method further comprises:
displaying the 3D model of the person's dentition; and
displaying, simultaneously with the 3D model, one or more annotated photos of the person's dentition, wherein the one or more annotated photos comprise or more overlays showing the one or more of the deviations relative to the photos of the person's dentition.

11. The method of claim 1, wherein the method further comprises:
displaying the 3D model of the person's dentition;
displaying, simultaneously with the 3D model, one or more annotated photos of the person's dentition, wherein the one or more annotated photos comprise or more overlays showing the one or more of the deviations relative to the photos of the person's dentition;
receiving instructions to interact with the 3D model or the one or more annotated photos of the person's dentition; and modifying a display of the 3D model and the one or more annotated photos while locking the 3D model and the one or more annotated photos to a common orientation.

12. The method of claim 1, wherein the method further comprises:
displaying one or more annotated photos of the person's dentition; and
displaying one or more staging elements configured to represent stages of the person's dentition over the course of the treatment plan.

13. The method of claim 1, wherein:
the method further comprises displaying one or more annotated photos of the person's dentition;
the method further comprises displaying one or more staging elements configured to represent stages of the person's dentition over the course of the treatment plan; and
the one or more staging elements show each jaw of the person's dentition relative to stages of the treatment plan.

14. The method of claim 1, wherein the method further comprises:
displaying a digital assessment corresponding to one or more of the deviations;
providing one or more digital diagnosis tools associated with the digital assessment; and
receiving a diagnosis from a doctor using the one or more digital diagnosis tools.

15. The method of claim 1, further comprising:
training a neural network to recognize machine-learned differences between projected representations of a first training set of 3D models and a second training set of training images; and
using the machine-learned differences to compare the photos to the projected representation of the 3D model.

16. The method of claim 1, further comprising:
providing intelligent guidance to a person to take the photos of the person's dentition; and
capturing the photos using the intelligent guidance.

17. The method of claim 1, wherein the photos do not comprise a three-dimensional (3D) mesh of the one or more teeth of the person's dentition.

18. The method of claim 1, wherein the photos do not comprise height-map data.

19. The method of claim 1, further comprising modifying the treatment plan using the discrepancies.

20. The method of claim 1, wherein the photos comprise a plurality of photos, each photo of the plurality of photos having a different orientation with respect to the person's dentition.

21. The method of claim 1, wherein the photos comprise a plurality of photos, a first photo of the plurality of photos having an anterior orientation, a second photo of the plurality of photos having a right buccal orientation, and a third photo of the plurality of photos having a left buccal orientation.

22. A system comprising:
one or more processors; and
memory storing computer program instructions that, when executed by the one or more processors, cause the system to execute a computer-implemented method comprising:
identifying a stage of a treatment plan administered to a person's dentition;
receiving a two-dimensional photo of the person's dentition corresponding to the stage of the treatment plan;
gathering a three-dimensional (3D) model of the person's dentition corresponding to the stage of the treatment plan;
projecting attributes of the 3D model of the person's dentition onto an image plane to get a projected representation of the person's dentition at the stage of the treatment plan;
comparing a position of one or more teeth of the person's dentition in the two-dimensional photo to the projected representation of the person's dentition to derive two-dimensional error image representing the comparison; and
analyzing the two-dimensional error image for discrepancies, wherein analyzing includes determining a distance between corresponding edges in the error image, and wherein the discrepancies represent one or more deviations of the person's dentition from the stage of the treatment plan.

23. The method of claim 1, wherein the distance is a pixel distance.

24. The method of claim 23, further comprising:
determining that a deviation of a tooth from an expected position exceeds a threshold distance based on the pixel distance.

* * * * *